US006996473B2

(12) United States Patent
Grass et al.

(10) Patent No.: US 6,996,473 B2
(45) Date of Patent: Feb. 7, 2006

(54) METHOD FOR SCREENING AND PRODUCING COMPOUND LIBRARIES

(75) Inventors: George M. Grass, Tahoe City, CA (US); Glen D. Leesman, Hamilton, MT (US); Daniel A. Norris, San Diego, CA (US); Patrick J. Sinko, Lebanon, NJ (US); John E. Wehrli, Mountain View, CA (US)

(73) Assignee: Lion Bioscience AG, Heidelberg (DE)

( * ) Notice: Subject to any disclaimer, the term of this patent is extended or adjusted under 35 U.S.C. 154(b) by 297 days.

(21) Appl. No.: 09/989,533

(22) Filed: Nov. 21, 2001

(65) Prior Publication Data

US 2002/0061540 A1 May 23, 2002

Related U.S. Application Data

(62) Division of application No. 09/320,069, filed on May 26, 1999, now abandoned.
(60) Provisional application No. 60/109,234, filed on Nov. 18, 1998, provisional application No. 60/109,232, filed on Nov. 18, 1998, provisional application No. 60/100,290, filed on Sep. 14, 1998, and provisional application No. 60/100,224, filed on Sep. 14, 1998.

(51) Int. Cl.
*G06N 3/00* (2006.01)
*G06N 7/60* (2006.01)
*G06F 9/455* (2006.01)

(52) U.S. Cl. .............................. 702/19; 703/2; 703/11
(58) Field of Classification Search ................... 702/19, 702/30; 703/2, 11, 3
See application file for complete search history.

(56) References Cited

U.S. PATENT DOCUMENTS

| | | | |
|---|---|---|---|
| 4,335,438 A | 6/1982 | Smolen | 364/497 |
| 4,411,989 A | 10/1983 | Grow | 435/20 |
| 4,775,794 A | 10/1988 | Behmann | 250/373 |
| 4,952,061 A | 8/1990 | Edgar | 356/407 |
| 4,975,581 A | 12/1990 | Robinson et al. | 250/339 |
| 5,331,573 A | 7/1994 | Balaji et al. | 364/500 |
| 5,387,421 A | 2/1995 | Amidon et al. | 424/472 |
| 5,569,452 A | 10/1996 | Amidon et al. | 424/78.1 |
| 5,579,250 A | 11/1996 | Balaji et al. | 364/496 |
| 5,625,579 A | 4/1997 | Hinsberg, III et al. | 364/578 |
| 5,657,255 A | 8/1997 | Fink et al. | 364/578 |
| 5,699,268 A | 12/1997 | Schmidt | 364/496 |
| 5,703,792 A | 12/1997 | Chapman | 364/496 |
| 5,705,335 A | 1/1998 | Hendry | 435/6 |
| 5,770,384 A | 6/1998 | Androphy et al. | |
| 5,789,160 A | 8/1998 | Eaton et al. | |
| 5,807,879 A | 9/1998 | Rosebrough | 514/387 |
| 5,808,918 A | 9/1998 | Fink et al. | 364/578 |
| 5,854,992 A | 12/1998 | Shakhnovich et al. | 702/27 |
| 5,880,972 A | 3/1999 | Horlbeck | 364/496 |
| 5,914,891 A | 6/1999 | McAdams et al. | 364/578 |
| 5,956,501 A | 9/1999 | Brown | 395/500.32 |
| 5,989,918 A | 11/1999 | Dietz et al. | 436/63 |
| 6,150,416 A | 11/2000 | Kick et al. | 514/616 |

FOREIGN PATENT DOCUMENTS

| | | |
|---|---|---|
| EP | 0 818 744 A2 | 1/1998 |
| EP | 0 918 296 A1 | 5/1999 |
| WO | WO 94/23705 | 10/1994 |
| WO | WO 96/13721 | 5/1996 |
| WO | WO 97/16717 | 5/1997 |
| WO | WO 97/20952 | 6/1997 |
| WO | WO 97/22000 | 6/1997 |
| WO | WO 97/29091 | 8/1997 |
| WO | WO 97/49987 | 12/1997 |
| WO | WO 98/00231 | 1/1998 |

OTHER PUBLICATIONS

Dowty et al. Improved absorption prediction of in vivo peroral absorption from in vitro intestinal permeability using an internal standard to control for intra– and inter–rat variability. Pharmaceutical Research (Dec. 1997) vol. 14 (12), pp. 1792–1797.*
Fecik et al. The search for orally active medications through combinatorial chemistry. Medicinal Research Reviews (May 1998) vol. 18 (3), pp. 149–185.*
Artursson et al., "Caco–2 Monolayers in Experimental and Theoretical Predictions of Drug Transport", Advanced durg Delivery Reviews (1996) vol. 22, pp 67–84.
Audus et al., "The Use of Cultured Epitheelial and Endothelial Cells for Drug Transport and Metabolism Studies", Pharmaceutical Research (1990) vol. 7, No. 5, pp 435–451.
Bailey et al., "The Use of the Intestinal Epithelial Cell Culture Model, Caco–2 in Pharmaceutical Development", Advanced Drug Delivery Reviews (1996) vol. 22 pp. 85–103.
de Boer et al., "Reconstitution of the Blood–Brain Barrier in Cell Culture for Studies for Drug Transport and Metabolism", Advanced Drug Deliver Reviews (1996) vol. 22, pp. 251–264.
Friedberg et al., "Recombinant DNA Technology as an Investigative Tool in Drug Metabolism Research", Advanced Drug Delivery Reviews (1996) vol.22, pp. 187–213.

(Continued)

Primary Examiner—Marjorie A. Moran
(74) Attorney, Agent, or Firm—Arent Fox PLLC

(57) ABSTRACT

A secondary compound library produced by a method of screening a compound library or portion thereof by absorption is provided. The method includes a step (i) that screens a primary compound library or portion thereof having a plurality of test samples containing isolated compounds or isolated mixtures of compounds per test sample by generating an in vivo absorption profile for each of the test samples from initial dose data and from in vitro bioavailability data comprising permeability and solubility data for each of the test samples, wherein the absorption profile includes at least one of rate of absorption, extent of absorption, and concentration of a test sample. Step (ii) produces a secondary compound library that includes at least one compound from the primary compound library having a desired absorption profile.

9 Claims, 36 Drawing Sheets

OTHER PUBLICATIONS

Grass et al., "Mechanisms of Corneal Drug Penetration III: Modeling of Molecular Transport", *Journal of Pharmaceutical Sciences*, (1988) vol. 77, No. 1, pp. 24–26.

Grass et al., "In Vitro Measurement of Gastrointestinal Tissue Permeability Using a New Diffusion Cell", *Pharmaceutical Research* (1988) vol. 5, No. 6, pp. 372–376.

Hidalgo et al., "Characterization of the Unstirred Water Layer in Caco–2 Cell Monolayers Using a Novel Diffusion Apparatus", *Pharmaceutical Research* (1991) vol. 8, No. 2, pp. 222–227.

Hidalgo et al., "Letter to the Editor: A New Side–by–Side Diffusion Cell for Studying Transport Across Epithelial Cell Monolayers", *In Vivo Cell. Dev. Biol.* (1992) vol. 28A, pp. 578–580.

Hidalgo et al., "Carrier–Mediated Transport and Efflux Mechanisms in Caco–2 Cells", *Advanced Drug Delivery Reviews* (*1996*) vol. 22, pp. 53–66.

Hu et al., "Membrane Permeability Parameters for Some Amino Acids and β–Lactam Antibiotics: Application of the Boundary Layer Approach", *J. Theor. Biol.* (1988) vol. 131, pp. 107–114.

Jezyk et al., "Permeability Characteristics of Various Intestinal Regions of Rabbit, Dog, and Monkey", *Pharmaceutical Research* (1992) vol. 9, No. 12, pp. 1580–1586.

Kou et al., "Calculation of the Aqueous Diffusion Layer Resistance for Absorption in a Tube: Application to Intestinal Membrane Permeability Determination", *Pharmaceutical Research* (1991) vol. 8, No. 3, pp. 298–305.

Kuhfeld et al., "In Vitro Measurement of Drug Transport Using a New Diffusion Chambers Compatible with Millicell Culture Supports: Performance with Caco–2 Monolayers", *International Journal of Pharmaceutics* (1996) vol. 133, pp. 47–58.

LeCluyse et al., "Strategies for Restoration and Maintenance of Normal Hepatic Structure and Function in Long–Term Cultures of Rat Hepatocytes", *Advanced Drug Delivery Reviews* (*1996*) *vol. 22, pp. 133–186.*

Mathias et al., "Respiratory Epithelial Cell Culture Models for Evaluation of Ion and Drug Transport", *Advanced Drug Delivery Reviews* (1996) vol. 22, pp. 215–249.

Maurel, P., "The Use of Adult Human Hepatocytes in Primary Culture and other In Vitro Systems to Investigate Drug Metabolism in Man", *Advanced Drug Delivery Reviews* (1996) vol. 22, pp. 105–132.

Pidgeon et al., "IAM Chromatography: An In Vitro Screen for Predicting Drug Membrane Permeability", *J. Med. Chem.* (1995) vol. 38, pp. 590–594.

Quaroni et al., "Development of Intestinal Cell Culture Models for Drug Transport and Metabolism Studies", *Advanced Drug Delivery Reviews* (1996) vol. 22, pp 3–52.

Rubas et al., "Comparison of the Permeability Characteristics of a Human Colonic Epithelial (Caco–2) Cell Line to Colon of Rabbit, Monkey, and Dog Intestine and Human Drug Absorption", *Pharmaceutical Research* (1993) vol. 10, No. 1, pp. 113–118.

Abstract from *Pharmaceutical Research* (1992) vol. 9, No. 10—PDD 7046, Lennernas et al., "Solvent Drag and Intestinal Drug Absorption Studied by Human Intestinal Perfusion" and PDD 7048, Karlsson et al., "A New Diffusion Chamber System for the Determination of Drug Permeability Coefficients Across the Human Intestinal Epithelium that are Independent of the Unstirred Water Layer"—page S–180.

Abstract from *Pharmaceutical Research* (1996) vol. 13, No. 9—PDD 7039, McCarthy et al., "Automated Permeability Analysis of Mixtures Across Caco–2 Cell Monlayers"—p. S–242.

Abstract from *Pharmaceutical Research* (1996) vol. 11, No. 10—APQ 1113, Kuhfeld et al., "An Automated In Vitro Permeability Screen Using Robotics", p. S–39.

Abstract from *Pharmaceutical Research* (1995) vol. 12, No. 9—BIOTEC 2064, Augustijns et al., "Permeability Screen for Synthetic Peptide Combinatorial Libraries Using Caco–2 Cell Monolayers and LC/MS/MS", p. S–94.

Aarons et al., "Computer–assisted Learning Lessions in Drug Disposition and Pharmacokinetics", *Journal of Pharmacological Methods* (1988) vol. 20, pp. 109–123.

Allen, G., "MODFIT: A Pharmacokinetics Computer Program", *Biopharmaceutics & Drug Disposition* (1990) vol. 11, pp. 477–498.

Amidon et al., "Model–Independent Prediction Methods in Pharmacokinetics: Theoretical Considerations", *Mathematical Biosciences* (1975) vol. 25, pp. 259–272.

Amidon et al., "A Theoretical Basis for a Biopharmaceutic Drug Classification: The Correlation of In Vivo Drug Product Dissolution and In Vivo Biavailability", *Pharmaceutical Research* (1995) vol. 12, No. 3, pp. 413–420.

Barbalas et al., "Quantitative Selected Ion Monitoring Processing System: Software and Hardware for the Automated Collection and Analysis of Selected Ion Monintoring Data Acquired for Use in Pharmacokinetic Studies", *Journal of Pharmaceutical Sciences* (1988) vol. 77, No. 8 , pp. 679–687.

Barvais et al., "The Pharmacokinetics of Intravenous Anesthetic Drugs Given by Infusion: SPINA\* —a Software Program", *European Journal of Anesthesiology* (1989) vol. 6, pp. 435–447.

Beckett et al., "A Model for Steroid Transport Across Biological Membranes", *J. Pharm Pharmac.*, (1975) vol. 27, pp. 226–234.

Berger et al., "Combining Statistical, Rule–Based, and Physiologic Model–Based Methods to Assist in the Management of Diabetes Mellitus", *Computers and Biomedical Research* (1990) vol. 23, pp. 346–357.

Blakey et al., "Quantitative Structure–Pharmacokinetics Relationships: I. Development of a Whole–Body Physiologically Based Model to Characterize Changes in Pharmacokinetics Across a Homologous Series of Barbiturates in the Rat", *Journal of Pharmacokinetics and Biopharmaceutics*, (1997) vol. 25, No. 3, pp. 277–312.

Bois et al., "Bioequivalence: Performed of Several Measures of Extent of Absorption", *Pharmaceutical Research* (1994) vol. 11, No. 5, pp. 715–722.

Bradshaw, J., "Prediction of Metabolism, Degradation and Toxicity of Xenobiotics", *Pesticide Sci.* (1992) vol. 34, No. 2, p. 185.

Campbell, D.B., "Extrapolation from Animals to Man: The Integration of Pharmacokinetics and Pharmacodynamics" in *Cellular and Molecular Mechanisms of Drugs of Abuse* (1996) Edited by S. F. Ali and Y. Takahashi, pp. 116–135.

Cardot et al., "PKC, A New Pharmacokinetic Software Using SAS", *European Journal of Pharmaceutics and Biopharmaceutics* (1997) vol. 43, pp. 197–199.

Chan et al., "Physiochemical and Drug–delivery Considerations for Oral Drug Bioavailability", *DDT* (1996) vol. 1, No. 11, pp. 461–473.

Chiou, W.L., "Determination of Drug Permeability in a Flat or Distended Stirred Intestine", *International Journal of Clinical Pharmacology and Therapeutics* (1994) vol. 32, No. 9, pp. 474–482.

Combrink et al., "A Comparison of the Standard Approach and the NONMEM Approach in the Estimation of Bioavailability in Man", *J. Pharm Pharmacol.* (1997) vol. 49, pp. 731–733.

Conolly et al., "Biologically Based Pharmacodynamic Models: Tools for Toxicological Research and Risk Assessment", *Ann. Rev. Pharmacol. Toxicol.* (1991) vol. 31, pp. 503–523.

Dijkstra et al., "Simulation of Nutrient Digestion, Absorption and Outflow in the Rumen: Model Description", *American Institute of Nutrition* (1992) pp. 2239–2256.

Dong, M.H., "Microcomputer Programs for Physiologically–based Pharmacokinetic (PB–PK) Modeling", *Computer Methods and Programs in Biomedicine* (1994) vol. 45, pp. 213–221.

Firmer et al., "Simulation of Gastrointestinal Drug Absorption I. Longitudinal Transport in the Small Intestine", *International Journal of Pharmaceutics* (1988) vol. 48, pp. 231–246.

Franck et al., "KINI: A One Compartment Intravenous Pharmacokinetic Analysis Program", *Computer Methods and Programs in Biomedicine* (1994) vol. 42, pp. 157–165.

Gex–Fabry et al., "Considerations on Data Analysis Using Computer Methods and Currently Available Software for Personal Computers" in *Handbook on Experimental Pharmacology* (1994) vol. 110, pp. 507–527 (Chapter 13).

Grass et al., "A Model to Predict Aqueous Humor and Plasma Pharmacokinetics of Ocularly Applied Drugs", *Investigative Ophthalmology & Visual Science* (1993) vol. 34, No. 7, pp. 2251–2259.

Grass et al., "Evaluation of the Performance of Controlled Release Dosage Forms of Ticlopidine Using In Vitro Intestinal Permeability and Computer Simulations", *Journal of Drug Targeting* (1994) vol. 2, pp. 23–33.

Grass, G.M., "Simulation Models to Predict Oral Drug Absorption from In Vitro Data", *Advanced Drug Delivery Reviews* (1997) vol. 23, pp. 199–219.

Gomeni et al., IGPHARM: Interactive Graphic Package for Pharmacokinetic Analysis, *Computers and Biomedical Research* (1978) vol. 11, pp. 345–361.

Gomeni, R., "Pharm–an Interactive Graphic Program for Individual and Population Pharmacokinetic Parameter Estimation", *Comput. Bio. Med.* (1994) vol. 14, No. 1, pp 25–34.

Hampton et al., "Comparison of MS–DOS and Macintosh Pharmacokinetic Analysis Programs Using a Two–Compartment, Two–Infusion Dosing Scheme", *Clinical Pharmacy* (1991) vol. 10, pp. 206–209.

Hayashi et al., "Pharmacokinetic Analysis of Cimetidine Plasma Concentration Data in Dogs Using a Two Phase Absorption Model", *Pharmaceutical Research* (1994) vol. 11, No. 10, p. S–420.

Hoang, K.T., "Physiologically Based Pharmacokinetic Models: Mathematical Fundamentals and Simulation Implementations", *Toxicology Letters* (1995) vol. 79, pp. 99–106.

Idkaldek et al., "Determination of the Population Pharmacokinetic Parameters of Sustained–Release and Enteric–Coated Oral Formulations, and the Suppository Formulation of Diclofenac Sodium by Simulatenous Data Fitting Using NONMEM", *Biopharmaceutics & Drug Disposition* (1998) vol. 19, pp. 169–174.

Jelliffe, R.W., "The USC*PACK PC Programs for Population Pharmacokinetic Modeling, Modeling of Large Kinetic/Dynamic Systems, and Adaptive Control of Drug Dosage Regimens" Symposium on *Computer Applications in Medical Care: A Conference of the American Medical Informatics Association* (1991) pp. 922–923.

Kalmaz, E.E., "Computer Modeling and Parameter Estimation for Pharmacokinetics and Toxicity Studies", *Journal of American College of Toxicology* (1996) vol. 5, No. 6, p. 607.

Keller et al., "Standardized Structure and Modular Design of a Pharmacokinetic Database", *Computer Methods and Programs in Biomedicine* (1988) vol. 55, pp. 107–115.

Kirkup et al., "A Demonstration of Pharmacokinetics and Physiological Modelling Using a Microcomputer for Data Capture and Analysis", *Computer Applications in the Biosciences* (1986) vol. 2, No. 4, pp. 277–282.

Kwon et al., "Theoretical Considerations on Two Equations for Estimating the Extent of Absorption After Oral Administration of Drugs", *Pharmaceutical Research* (1986) vol. 13, No. 4, pp. 566–569.

Langguth et al., "Variable Gastric Emptying and Discontinuities in Drug Absorption Profiles: Dependence of Rates and Extent of Cimetidine Absorption on Motility Phase and PH", *Biopharmaceutics & Drug Disposition* (1994) vol. 15, pp. 719–746.

Leader et al., "Integrating Pharmacokinetics into Point–of–Care Information Systems", *Clinical Pharmacokinetics* (1996) vol. 31, No. 3, pp. 165–173.

Lu et al., "An Interactive Program for Pharmacokinetic Modeling", *Journal of Pharmaceutical Sciences* (1993) vol. 82, No. 5, pp. 537–542.

Luner et al., "Description and Simulation of a Multiple Mixing Tank Model to Predict the Effect of Bile Sequestrants on Bile Salt Excretion", *Journal of Pharmaceutical Sciences* (1993) vol. 82, No. 3, pp. 311–318.

Mazumdar et al., "A Mathematical Study of Simple Exponential Modelling in Biochemical Processes", *Australasian Physical & Engineering Sciences in Medicine* (1991) vol. 14, No. 4, pp. 226–233.

Metzler et al., "Package of Computer Programs for Pharmacokinetic Modeling", *Biometrics, Journal of the Biometric Society* (1974) vol. 30, No. 3, pp. 562–563.

Metzler, C.M. "Commentary to 'Linear and Nonlinear System Approaches in Pharmacokinetics, How Much Do They Have To Offer?II. The Response Mapping Operator (RMO) Approach", *J. Pharmacokin. Biopharm,* (1988) vol. 16, pp. 543–571.

Murata et al., "Pharmacokinetic Analysis of Single or Multiple–Dose Plasma Drug Concentration Data with a Microcomputer Using Multi–Fraction Absorption Models", *Journal of Pharmaceutical Sciences* (1989) vol. 78, No. 2, pp. 154–159.

Nakai et al., "Evaluation of the Efficiency of Targeting of Antitumor Drugs: Simulation Analysis Based on Pharmacokinetic/Pharmacodynamic Considerations", *J. Drug Targeting* (1996) vol. 8, pp. 448–453.

Nikiforidis et al., "Individualization of Theophylline Infusion Rate on the Basis of a Nonlinear Compartmental Pharmacokinetic Model", *European Journal of Drug Metabolism and Pharmacokinetics* (1997) vol. 22, No. 3, pp. 265–276.

Nogami et al., "Pharmacokinetic Analysis on the Disappearance of Ethoxybenzamide from Plasma. Statistical Treatment of Data of Two Compartmental Model by a Digital Computer", *Chem. Pharm. Bull.* (1969) vol. 17, No. 10, pp. 2097–2104.

Oh et al., "Estimating the Fraction Dose Absorbed from Suspensions of Poorly Soluble Compounds in Humans: A Mathematical Model", *Pharmaceutical Research* (1993) vol. 10, No. 2, pp. 264–270.

Pearce et al., "A Hybrid Computer System for Pharmacokinetic Modeling I. Software Considerations", *Proceedings of the 1981 Summer Computer Simulation Conference* (1981) pp. 117–121.

Pearce et al., "PKDEMO—a Pharmacokinetic Demonstration Simulation Program", *Simulation* (1991) vol. 56, No. 1, pp. 27–30.

Powers et al., "Automated Processing of Data from Pharmacokinetic Investigations", *Computers and Biomedical Research* (1976) vol. 9, pp. 543–548.

Primozic, S., "Pharmacokinetic Modeling and Simulation", *Acta Pharm. Jugosl.* (1990) vol. 40, p. 209.

Ramsay et al., "Pharmacokinetic Simulations Using STELLA: Prediction of In Vivo Performance of Oral Dosage Forms", *Eur. J. Pharm. Biopharm.* (1991) vol. 37, No. 3, pp. 192–197.

Scaf, A.H.J., "Pharmacokinetic Analysis with Rugfit: An Interactive Pharmacokinetic Computer Program", *Biographamaceutics & Drug Disposition* (*1988*) vol. 9, pp. 415–446.

Staats et al., "Gastrointestinal Absorption of Xenobiotics in Physiologically Based Pharmacokinetic Models", *Drug Metabolism and Disposition* (1991) vol. 19, No. 1, pp 144–148.

Stigsby et al., "A Computer Model Simulating the Intestinal Absorption of Bile Acids", *Gastroenterology* (1983) pp. 802–807.

Tanswell et al., "TopFit: A PC–Based Pharmacokinetic/Pharmacodynamic Data Analysis Program", *International Journal of Clinical Pharmacology: Therapy and Toxicology* (1993) vol. 31, No. 10, pp. 514–520.

Taylor et al., "The Development of a Nonequilibrium Model for Computer Simulation of Multicomponent Distillation and Absorption Operations", *Distillation and Absorption* (1987) pp. B321–334.

Thomaseth, K., "PANSYM: A Symbolic Equation Generator for Mathematical Modelling, Analysis and control of Metabolic and Pharmacokinetic Systems", *Computer Methods and Programs in Biomedicine* (1994) vol. 42, No. 2, pp. 73–146.

Timcenko et al., "Estimation of Pharmacokinetic Model Parameters", *JAMA Proceedings* (1995) pp. 47–51.

Veng Pedersen, P., "Curve Fitting and Modeling in Pharmacokinetics and Some Practical Experiences with NONLIN and a New Program FUNFIT", *Journal of Pharmacokinetics and Biopharmaceutics* (1977) vol. 5, No. 5, pp. 513–531.

Veng Pedersen et al., "Perspectives in Pharmacokinetics: Linear and Nonlinear System Approaches in Pharmacokinetics: How Much Do They Have to Offer? II. The Response Mapping Operator (RMO) Approach", *Journal of Pharmacokinetics and Biopharmaceutics* (1988) vol. 16, No. 5, pp. 543–571.

Veng Pedersen, P., "Mathematical and Computational Tools of Linear and Non–linear System Analysis in Pharmacokinetics", *Acta Pharm. Jogosl.* (1990) vol. 40, pp. 211–224.

Verotta et al., "Simultaneous Modeling of Pharmacokinetics and Pharmacodynamics: An Improved Algorithm", *Computer Applications in the Biosciences*, (1987) vol. 3, No. 4, pp. 345–349.

Waters et al., "Use of Computerized Data Listings and Activity Profiles of Genetic and Related Effects in the Review of 195 Compounds", *Mutation Research* (1988) vol. 205 pp. 295–312.

Yu et al., "DeMons—A New Deconvolution Method for Estimating Drug Absorbed at Different Time Intervals and/or Drug Disposition Model Parameters Using a Monotonic Cubic Spline", *Biopharmaceutics & Drug Disposition* (1997) vol. 18, No. 6, pp. 475–487.

Zhang et al., "A Computer Model for Oral Transmucosal (OT) Bioavailability Prediction", *Pharmaceutical Research* (1997) vol. 14, No. 10, p. SA–662.

Zhou et al., "Methodology for Using Oral Dose Pharmacokinetic Data to Select Drugs for Prolonged Release Formulations and Validation of the Method Using Simulated Data", *Biopharmaceutics & Drug Disposition* (1995) vol. 16, pp. 319–331.

Abstracts from *Pharmaceutical Research* (1995) vol. 12, No. 9, p. S–367—PPDM8162, Yu et al., "Saturable Small Intestinal Drug Absorption in Humans: Modeling and Interpretation of Cefatrizine Data" and PPDM 8164, Heatherington et al., "A Pharmacokinetic–Pharmacodynamic Model to Predict Effect of Formulation of Lomustine on Medullat Blastoma Cells in the CSFG:A SAAM II Simulation".

Abstracts from *Pharmaceutical Research* (1992) vol. 9, No. 10, p. S–170—PDD 7005, Crison et al., "The Effect of Particle Size Distribution on Drug Dissolution: A Mathematical Model for Predicting Dissolution and Absorption of Suspensions in the Small Intestine" and PDD 7006, Kurihara–Bergstrom et al., "Transdermal Delivery of Buprenorphine in Man".

Carell et al., Abstract of "WO 95/19359," Jul. 20, 1995, Derwent Database.

Rossum et al., "Pharmacokinetics: A Dynamic Systems Approach," *Drug Metabolism and Distribution*, Edited by Lamble, Amsterdam: Elsiver Press, pp. 159–167, 1983.

Harvey, "Drug Absorption, Action and Disposition," Remington's Pharmaceutical Sciences, Easton Pennylsvania: Mack Publishing Co., Chap. 35 pp. 697–724, 1990.

Harvey et al., "Basic Pharmacokinetics," Remington's Pharmaceutical Sciences, Easton Pennsylvania: Mack Publishing Co., Chap. 36, pp. 725–745, 1990.

Rollins, "Clinical Pharmacokinetics," Remington's Pharmaceutical Sciences, Easton Pennsylvania: Mack Publishing Co., Chap. 37, pp. 746–756, 1990.

West Database Search Report for U.S. Appl. No. 5,770,384 (Androphy et al.).

West Database Search Report for U.S. Appl. No. 5,789,160 (Eaton et al.).

Seydel, J.K. et al., "Quantitative Structure–Pharmacokinetic Relationships and Drug Design", *Pharma. Ther.* (1982), vol. 15, pp. 131–181.

Enslein, Kurt, "The Future of Toxicity Prediction with QSAR", *In Vitro Toxicology A Journal of Molecular and Cellular Toxicology*, (1993) vol. 6, No. 3 pp. 162–169.

Notification of Transmittal of the International Search Report or the Declaration, Nov. 1, 2000, International Application No. PCT/US99/21001.

Written Opinion, Feb. 26, 2001, PCT/US99/21001.

Notification of Transmittal of International Preliminary Examination Report, Dec. 14, 2000, International Application No. PCT/US99/21151.

Written Opinion, Jul. 7, 2000, International Application No. PCT/US99/21151.

Notification of Transmittal of the International Search Report or the Declaration, Feb. 4, 2000, International Application No. PCT/US99/21151.

Abstract: Agrafiotis D. K.; Myslik J. C.; Salemme F. R., "Advances in diversity profiling and combinational series design", Accession No. 1999254287, 1999.

Abstract: Cho S J; Zheng W; Trophsha A, "Focus–2D: a new approach to the design of targeted combinatorial chemical libraries", 1998, Accession No. 1998362517.

Abstract: Klebe, Gerhard, "Recent developments in structure–based drug design", 2000, Accession No. 2000:377851 BIOSIS.

Abstract: Konings D A M; Wyatt J R; Ecker D J; Freier S M, "Strategies for rapid deconvolution of combinatorial libraries: Comparative evaluation using a model system", 1997, Accession No. 1998:59476.

Abstract: Muller, G., "Toward 3D structures of G protein-coupled receptors; a multidisciplinary approach", 2000, Accession No. 2000456233.

Abstract: Olson A J: Goodsell D S, "Automated docking and the search for HIV protease inhibitors", 1998, Accession No. 1998182948.

Abstract: Parks C A; Crippen G M; Topliss J G, "The measurement of molecular diversity by receptor site interaction simulation"; 1998 Accession No. 1099051971.

Abstract: Sadowski, Jens; Wagener, Markus; Gasteiger, Johann, "Assessing similarity and diversity of combinatorial libraries by spatial autocorrelation functions and neural networks", 1996, Accession No. 1996:48099.

Abstract: Stahura F L; Xue L; Godden J W; Bajorath J., "Molecular scaffold–based design and comparison of combinatorial libraries focused on the ATP–binding site of protein kinases." 1999 Accession No. 2000126742.

Abstract: Zheng W F; Cho, S. J.; Trophas A, "Rational design of a targeted combinatorial chemical library with opiatelike activity", 1998, Accession No. 1998:494993.

Abstract: Zheng W; Cho S J; Tropsha A, "Rational combinatorial library design. 1. Focus–2D: a new approach to the design of targeted combinatorial chemical libraries", 1998, Accession No. 1998199335.

Abstract: Zheng, Weifan; Cho, Sung Jin; Waller, Chris L.; Tropsha, Alexander, "Rational Combinatorial Library Design 3. Simulated Annealing Guided Evaluation (SAGE) of Molecular Diversity: A Novel Computational Tool for Universal Library Design and Database Mining", 1999, Accession No. 1999:354936.

Leahy et al., "Physiologic Based Pharmacokinetic Modelling and QSAR", *Bioactive Compound Design: Possibilities for Industrial Use*, 1996; pp. 147–151.

Seydel et al., "Drug–Membrane Interaction and Accumulation, Conformation Efficacy and Resistance", *Bioactive Compound Design: Possibilities for Industrial Use*; 1996; pp. 137–146.

Yang et al., "Pharmacokinetics", *Introduction to Biochemical Toxicology*, Edited by E. Hodgson and P.E. Levi, Appleton & Lange, Norwalk, CT, 1994; pp. 49–73.

Abstract: Holford, N.H.G. "Drugmodel", *Proceedings of the Fifth Annual Symposium on Computer Applications in Medical Care*, IEEE (1981); pp. 603–606.

Abstract: Hopfinger A. J.; Duca J.S., "Extraction of pharmacophore information from high–throughput screens", *Current Opinion in Biotechnology* (Feb. 2000), 11(1), 97–103, Ref:36 Journal Code: A92.ISSN:0958–1669.

Nicholas H.G. Holford, "DRUGMODEL", *Proceedings of the Fifth Annual Symposium on Computer Applications in Medical Care*, IEEE (1981); pp. 603–606.

* cited by examiner

| Symbol | Name | Time-Dependent Function |
|---|---|---|
| ☐ | Compartment | Equation or value for amount of substance stored. |
| ⊖→ | Flow Regulator | Rate equation for amount of substance transferred. |
| ○ | Converter | Equation or pre-defined value for (i) input into flow regulator; (ii) input into another converter; and/or (iii) storing value. |
| ∼↗ | Input Link | Directs input values. |

FIG. 13

Mass-Volume GI Tract Model

- GI Segment Compartments
  - Fluid Volume
  - Fluid Absorption
  - Insoluble Mass
  - Soluble Mass Absorption

- GI Segment Flow Regulators
  - Fluid Volume Absorption Rate
  - Fluid Volume Secretion Rate
  - Fluid Volume GI Transit Rate
  - Insoluble Mass GI Transit Rate
  - Soluble Mass Absorption Rate

- GI Segment Converters
  - Rate Constant
  - pH
  - Solubility
  - Surface Area
  - Permeability

FIG. 14

Mass-Volume GI Tract Model

- **GI Segment Compartments & *Flow Regulators***
  - Fluid Volume
    - *Fluid Volume Absorption Rate*
    - *Fluid Volume Secretion Rate*
    - *Fluid Volume GI Transit Rate*
  - Fluid Volume Absorption
    - *Fluid Volume Absorption Rate*
    - *Fluid Volume Secretion Rate*
  - Insoluble Mass
    - *Insoluble Mass GI Transit Rate*
    - *Soluble Mass Absorption Rate*
  - Soluble Mass Absorption
    - *Soluble Mass Absorption Rate*

FIG. 15

Mass-Volume GI Tract Model

- **GI Segment Flow Regulators & *Converters***
  - Fluid Volume Absorption Rate
    - *Fluid Volume Absorption Rate Constant*
  - Fluid Volume Secretion Rate
    - *Fluid Volume Secretion Rate Constant*
  - Fluid Volume GI Transit Rate
    - *Fluid Volume GI Transit Rate Constant*
  - Insoluble Mass GI Transit Rate
    - *Insoluble Mass GI Transit Rate Constant*
  - Soluble Mass Absorption Rate
    - *Fluid Volume*
    - *Insoluble Mass*
    - *Mass Solubility Profile*
      - *pH*
    - *Permeability*
    - *Surface Area*

FIG. 16

Mass-Volume GI Tract Model

- GI Segment Converters
  - Rate Constant
  - pH
  - Solubility
  - Surface Area
  - Permeability Gastrointestinal Transit pH Dependent Solubility and Dissolution Absorption GI Tract – Intestinal Model GI Tract-Intestinal Model (without converters, ghosts or connectors)

GI Tract-Intestinal Model

Parameters

Transit Time

Permeability Calculation

Solubility Calculation

Control Release Calculation

Concentration Calculation

Dissolution Calculation

FIG. 41

Physiological GI Tract Model

Database
- GI Segment Compartments
  - Fluid Absorption
  - Fluid Volume
  - Insoluble Mass
  - Soluble Mass
  - Soluble Mass Absorption
  - Dosage Form Mass

- GI Segment Flow Regulators
  - Fluid Absorption Rate
  - Fluid Volume Transit Rate
  - Insoluble Mass Transit Rate
  - Insoluble Mass Dissolution Rate
  - Soluble Mass Transit Rate
  - Soluble Mass Absorption Rate
  - Dosage Form Disintegration/Release Rate

- GI Segment Converters
  - Fluid Volume Absorption Rate Constant
  - GI Transit Rate Constant
  - Adjusted Dissolution Rate Constant
  - Dissolved Drug Concentration
  - Adjusted Surface Area
  - Adjusted Permeability

Rulebase
- GI Transit
- Dissolution
- Absorption
- Permeability Calculations
- Concentration Calculations
- Computational Error Corrections

FIG. 42

Physiological GI Tract Model

- **GI Segment Compartments & *Flow Regulators***
  - Fluid Absorption
    - *Fluid Absorption Rate*
  - Fluid Volume
    - *Fluid Volume Absorption Rate*
    - *Fluid Volume Transit Rate*
  - Insoluble Mass
    - *Insoluble Mass Transit Rate*
    - *Insoluble Mass Dissolution Rate*
  - Soluble Mass
    - *Insoluble Mass Dissolution Rate*
    - *Soluble Mass Transit Rate*
    - *Soluble Mass Absorption Rate*
  - Soluble Mass Absorption
    - *Soluble Mass Absorption Rate*

FIG. 43

Physiological GI Tract Model

- **GI Segments Flow Regulators & *Converters***
  - Fluid Absorption Rate
    - *Fluid Volume*
    - *Fluid Volume Absorption Rate Constant*
  - Fluid Volume Transit Rate
    - *Fluid Volume*
    - *Fluid Volume Transit Rate Constant*
  - Insoluble Mass Transit Rate
    - *Insoluble Mass*
    - *Insoluble Mass Transit Rate Constant*
  - Insoluble Mass Dissolution Rate
    - *Insoluble Mass*
    - *Dissolution Rate Constant*
  - Soluble Mass Transit Rate
    - *Soluble Mass*
    - *Soluble Mass Transit Rate Constant*
  - Soluble Mass Absorption Rate (Flux)
    - *Surface Area*
    - *Dissolved Mass Concentration*
    - *Permeability*

FIG. 44

Physiological GI Tract Model

- Converters
  - Permeability
    - Passive Absorption Adjustment Parameter
      - Efflux/Secretion Adjustment Parameter
      - Active Absorption Adjustment Parameter
      - Active or Carrier Mediated Absorptive Permeability
      - Km
      - Passive Permeability/Regional Correlation
        - Passive Permeability
        - Logic Function For Regional Correlation
          - Passive Permeability
          - Logic Function For Regional Correlation
      - Dissolved Mass Concentrations
  - Dissolved Mass Concentration
    - Fluid Volume
    - Solubility
      - pH
      - Solubility
  - Dissolution Rate Constant
    - Fluid Volume
    - Precipitation Rate Constant
    - Dissolution Rate Adjustment Parameter
    - Solubility
    - Insoluble Mass
    - Soluble Mass
  - Surface Area
    - Surface Area Adjustment Parameter
    - Transport Mechanism
  - Transit Rate
    - Transit Time Adjustment Parameter
    - User Adjusted Transit Time
  - Fluid Volume Absorption Rate Constant
    - Fluid Volume Adjustment Parameter Correlation of FDp Extent - GI Model and Pharmacokinetic data FDp predicted – GI Model Correlation of FDp rate of absorption – GI Model and Pharmacokinetic Data t50 – GI Model PO Pharmacokinetic Data
Compound α 1

---- Input From PK Fitting
—— Input From GI-Model
● Oral Data

PO Pharmacokinetic Data
Compound α 4

---- Input From PK Fitting
—— Input From GI-Model
● Oral Data

METHOD FOR SCREENING AND PRODUCING COMPOUND LIBRARIES

This is a Division of application Ser. No. 09/320,069 filed May 26, 1999 now abandoned. The disclosure of the prior application(s) is hereby incorporated by reference herein in its entirety.

CROSS REFERENCE TO RELATED APPLICATIONS

This application is related to the following U.S. Provisional Application Ser. Nos.: 60/100,290, filed Sep. 14, 1998; 60/109,232, filed Nov. 18, 1998; 60/100,224, filed Sep. 14, 1998; and 60/109,234, filed Nov. 18, 1998.

INTRODUCTION

TECHNICAL FIELD

The present invention relates to screening and production of compound libraries for drug development.

BACKGROUND

Conventional methods to identify leads for drug development involve primary screening of compound libraries for activity "hits," followed by secondary screening to reduce the number of primary hits to a congeneric series of optimal leads for drug development.

The compound libraries, such as synthetic (e.g., combinatorial) and natural product (e.g., biological preparations and extracts) libraries, vary in size and complexity, ranging from hundreds, thousands, to millions or more of related or diverse compounds. The smaller libraries usually are well defined and each of the compounds frequently are contained in a separate storage or test vessel (e.g., dry or liquid form of the compound residing in a well of a multi-well storage or test plate with other members of the library). Larger libraries often are deconvolution and chemical analyses are typically performed in parallel to isolate and characterize the compound(s) responsible for the observed activity. Information gleaned from the initial screening and testing process also is used for subsequent rounds of analog synthesis (analog/focused libraries) and convergent screening and testing of particular analogs (i.e., iterative process). Computer-implemented theoretical or virtual compound libraries also provide a repository from which activity hits are selected for known or predicted structure-activity relationships.

Primary activity screening of compound libraries is based on selection of compounds that directly or indirectly interact with a specific biological receptor(s) (i.e., receptor-dependent activity screening). Isolated receptors and cells expressing single or combinations of receptors chosen to mimic a particular biological system or disease state generally provide the context of an assay for receptor-dependent activity screening. For high-throughput screening of larger libraries, automated systems utilizing multi-well arrays representing isolated receptors or cells that express them are the standard.

The driving force behind receptor-dependent activity screening as the primary approach for sifting through compound libraries is simple. Drugs (pharmacological/toxicological agent) elicit a pharmacological response through interaction with one or more biological receptors (drug/receptor-specific interaction). Thus, compounds that interact with a particular receptor or combination of receptors are presumed to be the most promising candidates for exhibiting some mutual activity in vivo and thus targets for secondary screening.

Compounds identified from a primary screen are then subjected to successively more focused and quantitative rounds of screening and validation to eliminate false positives and identify those exhibiting optimal biological activity against a target receptor(s) in an in vivo setting. This typically involves a combination of physiochemical and biological testing, including structural characterization and biological studies using cells, tissues and animals. Compounds with the most promising biological activity are selected as leads for drug development.

Drug development involves scale up and detailed toxicity, pharmacodynamic and pharmacokinetic studies that are performed to characterize pharmacological efficacy. These studies are conducted not only to gauge whether a test compound has activity in an in vivo setting, but also to examine bioavailability to assess possible route of administration, delivery formulations and the amount of a test compound necessary over time to produce a therapeutic effect with little or acceptable side effects. A variety of cell, tissue and animal model assays typically are employed for such studies. A handful of compounds (e.g., 5–10) that pass these tests are then tested in scaled up animal studies for further characterization. A lead drug compound with the most promising results in animal studies is then tested in humans in clinical trials.

Pharmacokinetic studies are conducted to characterize the time-dependent concentration of a test compound in the body, which collectively depends on absorption, distribution, metabolism and elimination (ADME) of the compound following administration. For instance, in order to reach the site of action, a lead drug compound that is administered to a subject must first be absorbed across epithelial barriers, usually by passive diffusion and/or active uptake, into the systemic circulation. In the case of intravascular administration, absorption is instantaneous and complete. However, all other routes of administration involve an absorption step with the potential that only a fraction of the administered compound may be absorbed into systemic circulation.

Systemic blood then delivers the compound to cells and tissues in the body, where the likely receptor/site of action resides, but various parallel processes compete for the compound. The compound may reversibly bind with proteins (albumin, al-acid glycoprotein) in plasma, or in some instances with tissue proteins. This is important since an unbound compound is typically the form taken up by cells and tissues. These processes determine distribution of the compound.

In a process referred to as excretion or elimination, organs such as the kidney, lung and liver are able to remove an unchanged lead drug compound from systemic circulation. Alternatively, the compound may be metabolized by enzymes frequently localized in all tissues, but mainly in the liver. Such metabolism produces metabolites that are chemically different from the administered compound and generally are more readily excreted from the body (reduced lipid solubility). Often the pharmacological/toxicological activity of a metabolite is reduced compared to that of the parent compound.

Thus while a lead or collection of lead drug compounds may continue to exhibit promising activity profiles early in the drug development process, most fail to make it as a drug product because of poor bioavailability discovered in animals, or worse poor bioavailability not discovered until human clinical trials (e.g., gancyclovir). This unacceptably high and expensive failure rate can be attributed in large part to the biased nature of activity-based screening to identify primary hits ultimately used as lead drug candidates. For instance, activity screening is pursued from the mindset that the greater and more specific the compound-receptor interaction/activity, the more potent a compound, and thus the smaller the dose required and consequent lower potential for toxic side-effects, as well as cheaper product produced and sold. However, a potent compound exhibiting poor bioavailability might require a higher dose than a less potent compound exhibiting superior bioavailability; this less potent compound also may exhibit reduced dose related toxicity. Therefore, the majority of activity levels do not result in drug products.

Receptor-dependent screening and testing also provides little to no information as to the probable route of administration for an activity hit. As an example, a test compound selected for activity may ultimately require intravenous administration, which is a less preferred route of administration. Here again a different less potent compound overlooked or discarded from an activity screen for lower potency may have been a good candidate for a preferred extravascular form of administration (e.g., oral). An oral form would be cheaper to administer even if administered at a higher dose to compensate for lower potency.

The dogmatic process of screening compound libraries first by receptor activity likewise reduces the value of the libraries themselves. Newly obtained or previously screened compounds having true therapeutic potential due to superior bioavailability properties are likely never to make it into the drug development pipeline if they fail to pass the primary activity screening process. Also valuable physical and chemical information from compounds otherwise possessing good bioavailability profiles that are discarded or overlooked for having less than some preferred activity level will be lost and unavailable for future development of structurally related activity leads or synthesis of new libraries.

Accordingly, a need exists for identifying compounds that exhibit desired pharmacokinetic properties before the drug development process, as well as guidance for future synthesis. The present invention provides an unprecedented and counterintuitive approach to address these and other needs.

RELEVANT LITERATURE

Barlow et al. (WO 9716717) disclose a robotic system for automated in vitro measurement of cell permeability. Pidgeon et al. (*J. Med. Chem.* (1995) 38:590–594) disclose immobilized artificial membranes for permeability assays. Minth et al., (*Eur. J. Cell. Biol.* (1992) 57:132–137) disclose apparatus for perfusion cell cultures and in vitro assays. Various pharmacokinetic models of oral drug absorption are disclosed in Grass, G. (*Advanced Drug Delivery Reviews* (1997) 23:199–219); Amidon et al., (*Pharm.* (1988) 5:651–651); Chiou, W. L., (*Int. J. Clin. Pharmacol. Ther.,* (1994) 32:474–482); Chiou, W. L., (*Biopharm. Drug Dispos.,* (1995) 16:71–75); Dressman et al., (*J. Pharm. Sci.,* (1985) 74:588–589); Lennernas et al., (*J Pharm. Pharmacol.,* (1997) 49:682–686); Levet-Trafit et al., (*Life Sciences.,* (1996) 58: PL359–63); Sinko et al., (*Pharm. Res.,* (1991) 8:979–988); and Soria et al.,. (*Biopharm. Drug Dispos.,* (1996) 17:817–818)). Grass et al., (Investigative Ophthamology & Vis. Sci. (1993) 34(7):2251–2259) disclosure simulation model to predict aqueous humor and plasma pharmacokinetics of oculatory applied drugs. Audus et al., (Pharm. Res. (1990) 7(5):435–451) reviews epithelial and endothelial cell models for drug transport and metabolism.

SUMMARY OF THE INVENTION

The present invention relates to a method of screening and producing compound libraries selected for absorption, and optionally, one or more additional properties. Novel libraries produced by the method of the invention also are provided. The method is readily adapted for high-throughput screening and production of compound libraries optimized for absorption. The method and libraries of the invention can be utilized for preparation of a medicament for use in the treatment of a mammal.

The method involves screening a first compound library or portion thereof which comprises a plurality of test samples containing isolated compounds and/or isolated mixtures of compounds per test sample. Screening is performed by: (i) generating an in vivo absorption profile for each test sample from initial dose or amount and in vitro bioavailability data comprising permeability and solubility data, and optionally dissolution rate and transfer mechanism data, where an absorption profile is characterized by one or more of concentration, rate and extent of transfer of a test sample across a physiological barrier from the site of administration to a selected sampling site of a mammalian system of interest; (ii) selecting compounds having a desired absorption profile; (iii) and producing a second compound library comprising the selected compounds; and (iv) optionally repeating steps (i) through (iii) one or more times, where a compound library selected for absorption is obtained.

The present invention also provides a method for generating an in vivo absorption profile. This method involves providing in vitro bioavailability data for a test sample of a compound library as input data to a computer-implemented pharmacokinetic tool (PK tool) of the invention. The PK tool includes as computer-readable components: (a) an input/output system suitable for data input and data output; (b) a simulation engine; and (c) a simulation model characterized by a multi-compartment physiological model of a mammalian system of interest comprising a barrier to absorption that is based on a selected route of administration. The input/output system, simulation engine and simulation model are capable of working together to carry out the steps of receiving as input data, initial dose of a test sample at the site of administration and in vitro bioavailability data including one or more of permeability, solubility, dissolution rate, and transfer mechanism data, and generating as output data a simulated in vivo absorption profile for each test sample that reflects rate, extent and/or total concentration of the test sample at a given a sampling site located on the other side of the barrier to the site of administration.

Subsequent rounds of screening according to the method of the invention provide new secondary compound libraries that are increasingly optimized for bioavailability. The libraries of the invention may be utilized to generate additional sub-libraries by screening. Accordingly, libraries produced by the method of the invention increase the chance of identifying compounds having desired in vivo pharmacological activity for a selected route of administration.

DEFINITIONS

Absorption: Process by which a compound transfers across a physiological barrier as a function of time and initial concentration. Amount or concentration of the compound on the external and/or internal side of the barrier is a function of transfer rate and extent, and may range from zero to unity.

Bioavailability: Fraction of an administered dose of a compound that reaches the sampling site and/or site of action. May range from zero to unity.

Compound: Chemical entity.

Compound Library: A collection of two or more isolated compounds, pools of compounds, or combinations thereof. Examples include natural, synthetic and synthetic combinatorial compound libraries. May include computer-readable compound files.

Computer Readable Medium: Medium for storing, retrieving and/or manipulating information using a computer. Includes optical, digital, magnetic mediums and the like; examples include portable computer diskette, CD-ROMs, hard drive on computer etc. Includes remote access mediums; examples include internet or intranet systems. Permits temporary or permanent data storage, access and manipulation.

Data: Experimentally collected and/or predicted variables. May include dependent and independent variables.

Dissolution: Process by which a compound becomes dissolved in a solvent.

Input/Output System: Provides a user interface between the user and a computer system.

Permeability: Ability of a physiological barrier to permit passage of a particular substance. Refers to the concentration-dependent or concentration-independent rate of transport (flux), and collectively reflects the effects of characteristics such as molecular size, charge, partition coefficient and stability of a compound on transport. Permeability is substance and barrier specific.

Physiologic Pharmacokinetic Model: Mathematical model describing movement and disposition of a compound in the body of a mammal or an anatomical part of the body based on pharmacokinetics and physiology.

Primary Compound Library: Compound library having compounds not yet screened and selected for (i) absorption, or (ii) absorption and one or more additional bioavailability properties.

Secondary Compound Library: Compound library derived from a primary compound library having compounds screened and selected for one or more particular properties.

Simulation Engine: Computer-implemented instrument that simulates behavior of a system using an approximate mathematical model of the system. Combines mathematical model with user input variables to simulate or predict how the system behaves. May include logic components, such as system control statements.

Solubility: Property of being soluble; relative capability of being dissolved.

Transport Mechanism: The mechanism by which a compound passes a physiological barrier of tissue or cells. Includes four basic categories of transport: passive paracellular, passive transcellular, carrier-mediated influx, and carrier-mediated efflux.

BRIEF DESCRIPTION OF DRAWINGS

FIG. 13 illustrates compartment, flow regulator and converter components for differential equations of the mass-volume GI tract simulation model of the invention.

FIG. 14 illustrates structural relationship among compartment and flow regulator components for differential equations of the mass-volume GI tract simulation model of the invention.

FIG. 15 illustrates structural relationship among flow regulator and converter components for differential equations of the mass-volume GI tract simulation model of the invention.

FIG. 16 illustrates converter components for differential equations of the mass-volume GI tract simulation model of the invention.

FIG. 41 illustrates database and rulebase compartment, flow regulator and converter components for differential equations of the integrated physiologic-based GI tract simulation model of the invention.

FIG. 42 illustrates structural relationship among compartment and flow regulator components for differential equations of the integrated physiologic-based GI tract simulation model of the invention.

FIG. 43 illustrates structural relationship among flow regulator and converter components for differential equations of the integrated physiologic-based GI tract simulation model of the invention.

FIG. 44 illustrates structural relationship among converter components for differential equations of the integrated physiologic-based GI tract simulation model of the invention.

DESCRIPTION OF SPECIFIC EMBODIMENTS

Figure 1:
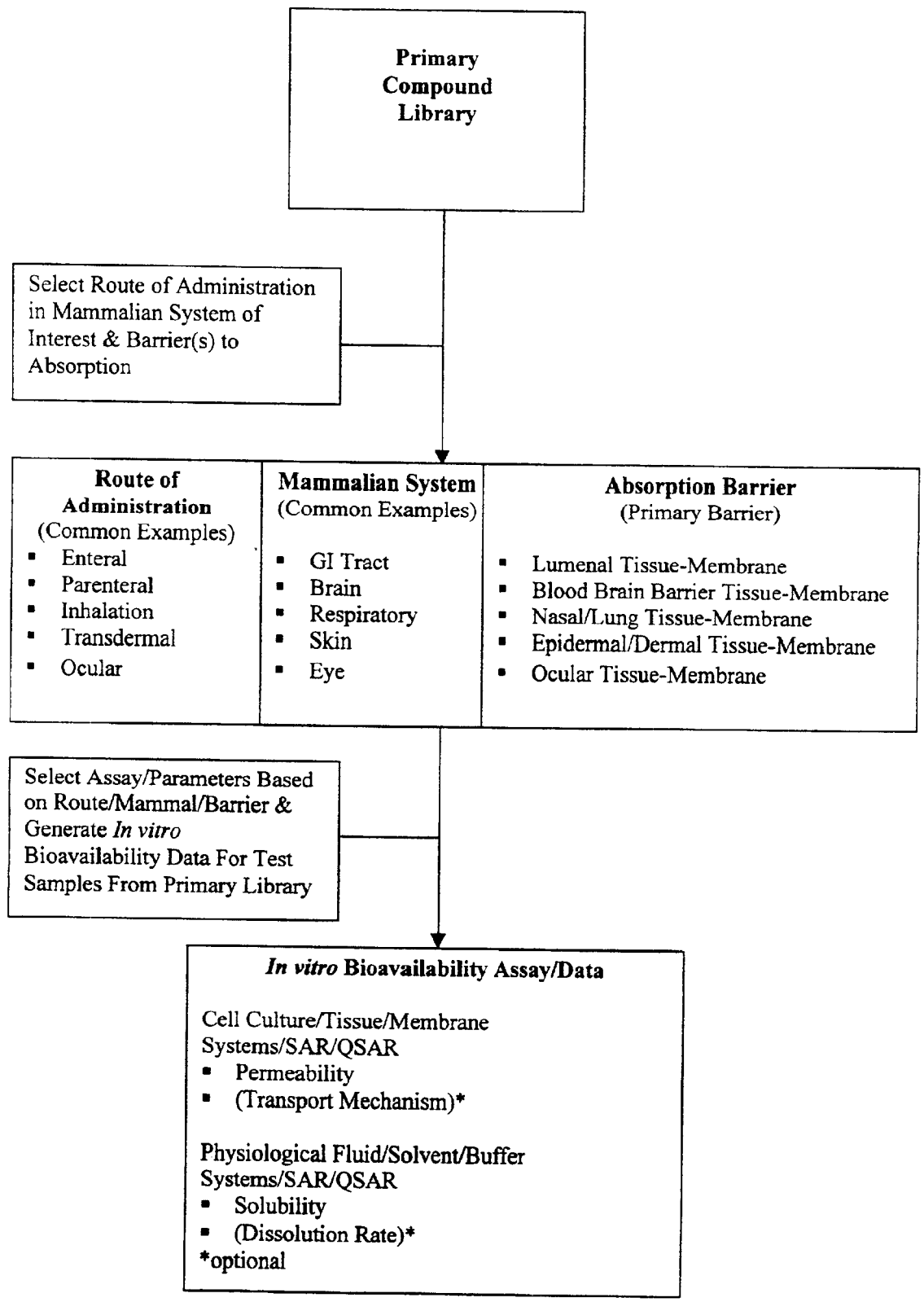
FIG. 1 shows schematic of method of the invention to generate in vitro bioavailability data for screening a primary compound library by absorption parameters.
Figure 2:
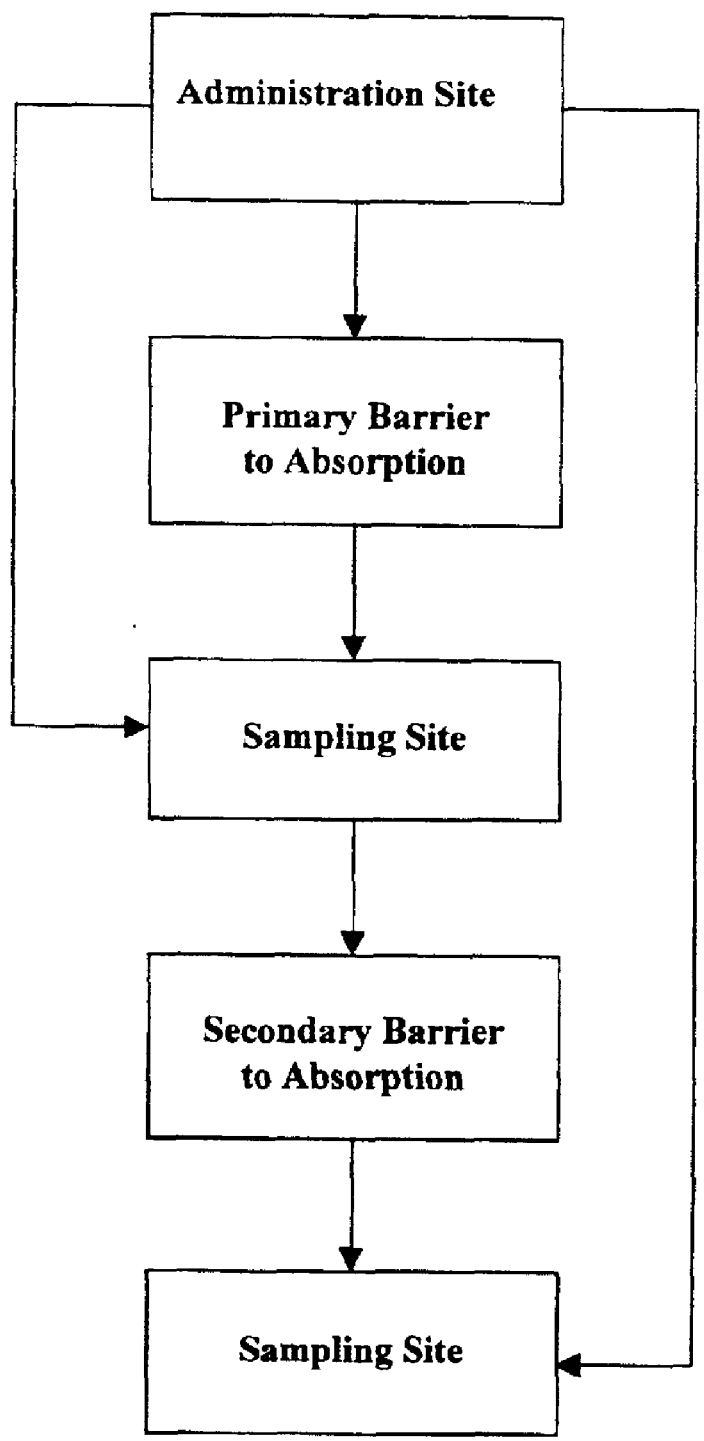
FIG. 2 shows schematic of method of the invention for selecting sampling site relative to administration site and barrier to absorption.
Figure 3:
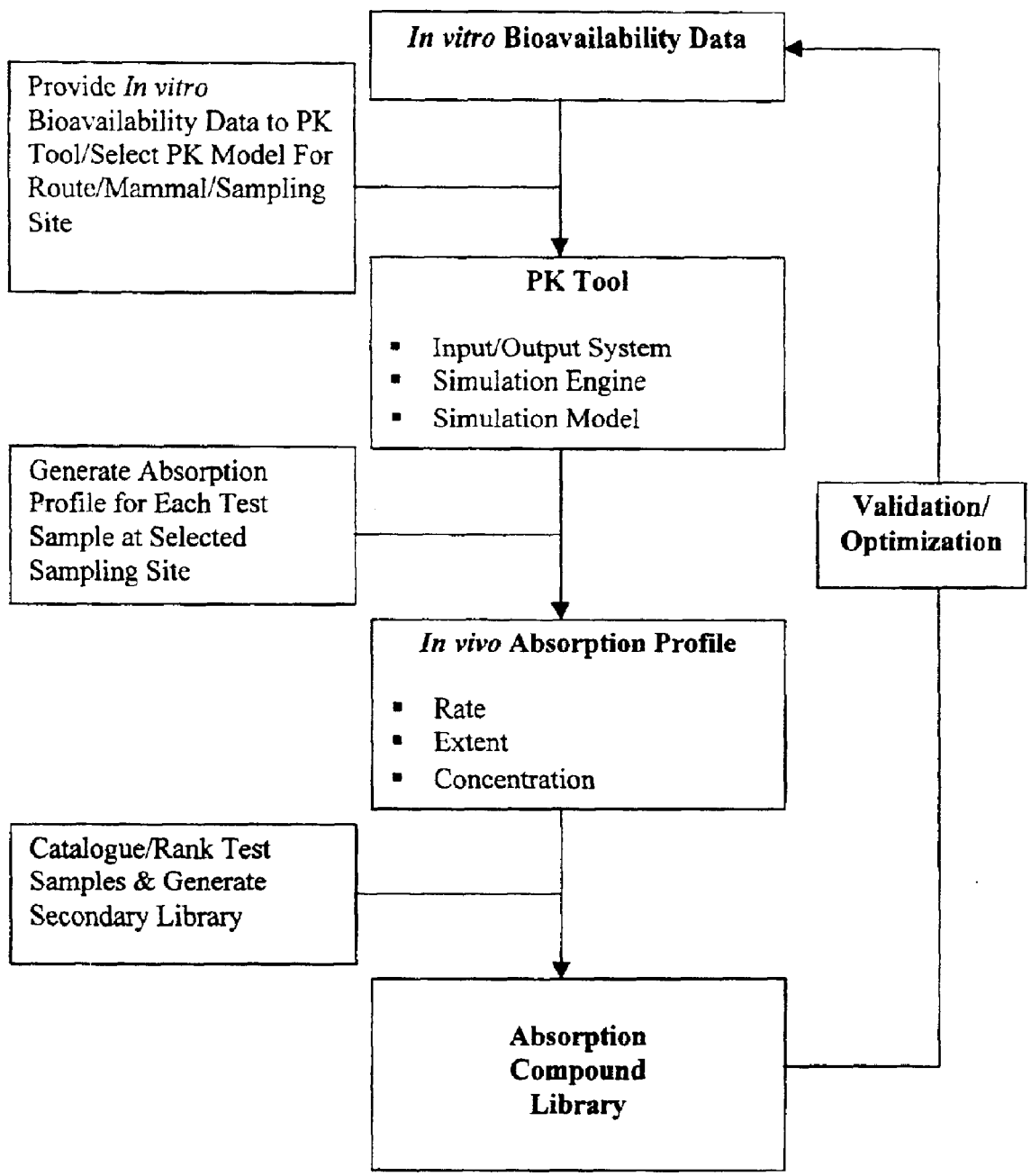
FIG. 3 shows schematic of method of the invention to generate an absorption compound library from in vitro bioavailability data.
Figure 4:
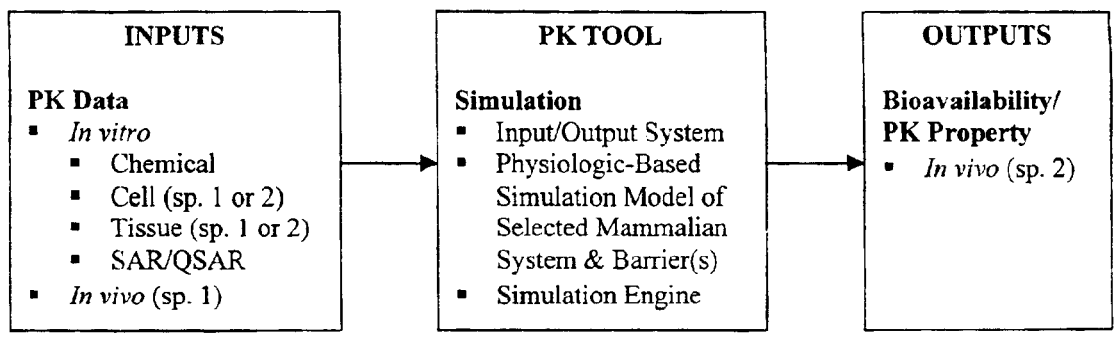
FIG. 4 is a high level INPUT/PROCESS/OUTPUT diagram of the PK tool of the invention.
Figure 5:
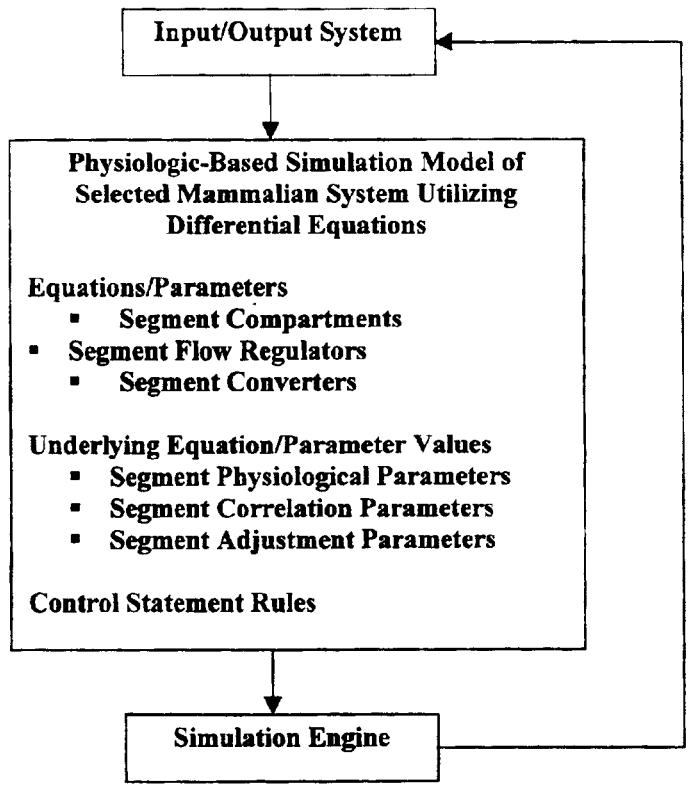
FIG. 5 is a high level flow chart and structure chart of the PK tool and method of the invention.
Figures 6, 7:
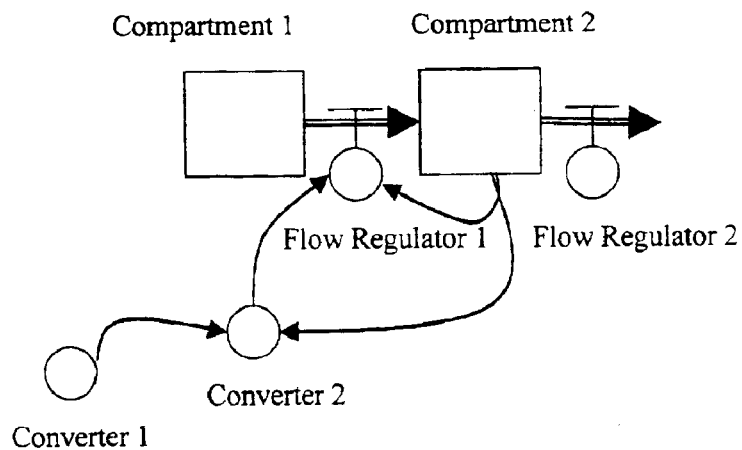
FIG. 6 is a graphical diagram illustrating generic compartment-flow simulation model and exemplary symbolic relationships among compartments, flow regulators, converters and input links.
FIG. 7 is a key for FIG. 6.
Figure 8:
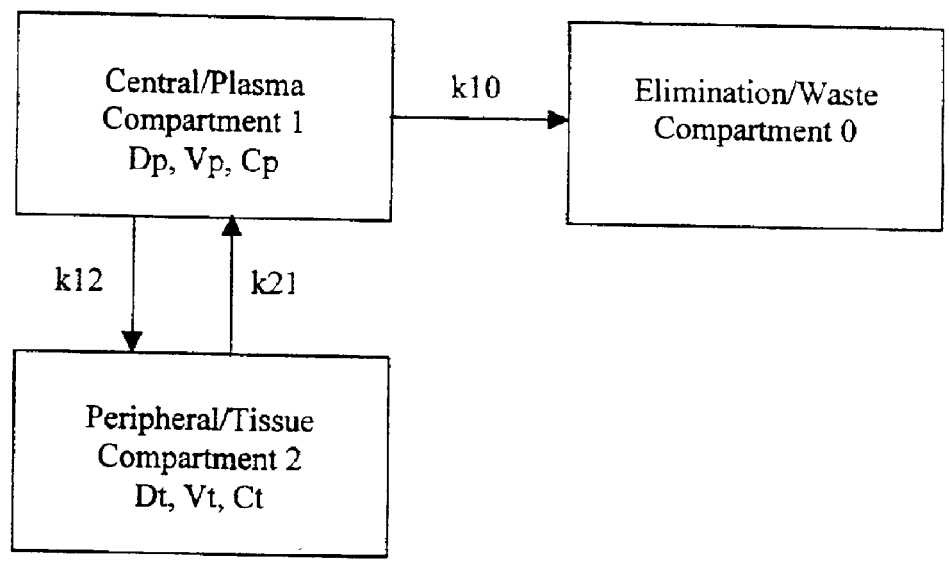
FIG. 8 is a graphical diagram illustrating generic pharmacokinetic first-order two-compartment open plasma model for intravenous injection. D is total drug, V is apparent volume of distribution, and C is drug concentration for either plasma (p) or tissue (t). k12 and k21 represent first-order rate transfer constants for movement of drug from compartment 1 to compartment 2 (k12) and from compartment 2 to compartment 1 (k21). k10 represents first-order rate transfer constant for movement (elimination) of drug from compartment 1 to compartment 0.

The present invention relates to a method for screening compound libraries by absorption, or absorption and one or more additional properties. The invention also relates to compound libraries produced by the method of the invention.

The method of the invention involves screening a first compound library or portion thereof by absorption, where the compound library or portion thereof includes a plurality of test samples containing isolated compounds and/or isolated mixtures of compounds per test sample. Screening of the first compound library or portion thereof is performed by: (1) generating an in vivo absorption profile from in vitro bioavailability data for each test sample, where the absorption profile is based on a selected route of administration and sampling site of a mammalian system of interest; and (2) selecting test samples having a desired absorption profile compared to others.

The in vivo absorption profile is characterized by absorption rate, extent of absorption, and/or concentration of a test sample relative to a selected site of administration and a selected sampling site of the mammalian system of interest, i.e., rate and/or extent of transfer of a test sample from an external site (e.g., apical) across a physiological barrier (e.g., epithelium) to an internal site (e.g., basolateral) of that barrier. Transfer rate and/or extent are generated from initial dose data (e.g., amount) for the test sample and in vitro derived bioavailability data including permeability and solubility data, and optionally dissolution rate and transport mechanism data (i.e., passive paracellular, passive transcellular, carrier-mediated influx, carrier-mediated efflux) for the test sample. Solubility and dissolution rate are interrelated and effect the ability of the compound to be solubilized at a rate sufficient for absorption to occur across a particular membrane. Permeability refers to the concentration-dependent or concentration-independent rate of transport (flux), and collectively reflects the effect of molecular size, charge, partition coefficient and stability of a compound on absorption for a particular physiological barrier, where the physiological barrier(s) depends on the selected route of administration. Molecular size, charge and partition coefficient determines in large part whether a compound is transported via a paracellular or transcellular mechanism. Stability is a general feature that relates to whether the compound remains intact long enough to be absorbed. Together, in vitro derived solubility and permeability data, and optionally dissolution rate and transport mechanism data, are primary bioavailability factors utilized to prepare an absorption profile for a test sample of interest.

An in vivo absorption profile may be generated by any number of pharmacokinetic techniques. The preferred method for generating an in vivo absorption profile is by providing initial dose and in vitro bioavailability data for each test sample as input data to a computer-implemented pharmacokinetic tool (PK tool) of the invention as described herein. The PK tool then generates as output a simulated in vivo absorption profile. This aspect of the invention provides a rapid and accurate way to predict in vivo absorption of a library of compounds from in vitro data, or absorption in one type of mammal (e.g., rabbit) to a different type of mammal (e.g., human). This is important since in vitro absorption data cannot be used directly to predict absorption in vivo, nor can in vivo data from one type of mammal be used directly to predict absorption in a second different type of mammal. Moreover, when a diverse set of compounds reside within a library to be screened, then conventional methods of utilizing in vitro data to predict in vivo absorption, or in vivo absorption data from one type of mammal to the next will have an unacceptably high failure rate, i.e., false positives and false negatives relative to absorption. The PK tool of the invention also is readily adaptable for both high-throughput and high-resolution screening formats, and provides information necessary for ranking compounds by bioavailability parameters comprising absorption where statistical correlation and other prediction schemes fail.

The PK tool includes as computer-readable components, an input/output system, a simulation model, and a simulation engine. The input/output system may be any computer-implemented system suitable for data input and data output and operable interaction with the simulation engine and simulation model. The simulation engine includes a differential equation solver, and optionally a system control statement module. This includes various computer-readable algorithms for numerical iteration of mathematical equations over interval dt and for processing rules, scenarios, pattern matching and the like that direct the simulation. The simulation model corresponds to a physiologic-based multi-compartment model of a mammalian system of interest, where the mammalian system represents a barrier to absorption that is based on a selected route of administration, i.e., the location at which the compound is introduced to a mammal. More particularly, the physiologic-based simulation model of the PK tool of the invention is a mathematical model comprising as operably linked components: (i) differential equations for calculating rate, extent and concentration of a test sample for one or more physiological segments of the mammal system of interest; and (ii) initial parameter values for the differential equations corresponding to physiological parameters, and optionally one or more regression analysis derived adjustment parameters, and optionally one or more regional correlation parameters, for one or more physiological segments of the mammal system of interest; and optionally (iii) control statement rules for one or more of absorption, permeability, solubility, dissolution, concentration, and mathematical error correction, for one or more physiological segments of the mammal system of interest.

The differential equations of a selected simulation model of a mammalian system of interest describe the rate processes of absorption, and optionally other events, of that model, which in turn describe drug concentrations in the system as a function of time. (See, e.g., Shargel et al., *Applied Biopharmaceutics and Pharmacokinetics,* Appelton & Lange, East Norwalk, Conn., 1993).

The initial parameter values of a given simulation model can be generated de novo or obtained from existing sources including the literature. A simulation model of the invention preferably includes selectively optimized regression analysis derived adjustment parameters that modify other parameters and the underlying equations of the model. The adjustment parameters facilitate accurate correlation of in vitro data derived from a particular type of assay (e.g., Caco-2 cells, segment-specific rabbit intestinal tissue sections etc.) to in vivo absorption for a mammalian system of interest (e.g., segment-specific portions of the human GI tract) for diverse test sample data sets. The adjustment parameters are obtainable using standard regression-based curve-fitting algorithms that simultaneously estimate the change required in a value assigned to an initial absorption parameter of the model in order to change an output variable. The adjustment parameters are provided to a given simulation model as constants or ranges of constants that modify the underlying equations of the model.

For a simulation model representing two or more anatomical segments of a given mammalian system, the model will preferably include regional correlation parameters. The regional correlation parameters permit estimation of a selected parameter value for a first segment of the mammalian system from correlation using a value of the selected parameter for a second segment of the mammalian system. The regional correlation parameters represent a collection of empirically derived values or adjustment parameter values for various segments of the mammalian system of interest, for example, permeability values. The regional (i.e., segmental) correlation is performed by logic function of the model, which when activated utilizes a polynomial-based algorithm to estimate the parameter value for the second segment from (1) the corresponding regional correlation parameters, and (2) a user provided input value for the same parameter, but for a different segment. The regional correlation logic function of the model is activated when a user does not supply an input value for a particular parameter. For example, when a user of the PK tool supplies a single permeability value as input into a GI tract simulation model of the invention, such as a permeability value derived from Caco-2 cells that corresponds to colon, then regional permeability correlation is performed by the PK tool to estimate permeability in the other GI track segments, such as duodenum, jejunum, and ileum.

The control statement rules include various logic elements utilized for providing guidance as to how a given simulation is to proceed. For instance, a control statement rule would include "IF . . . THEN" production rules. An example of a production rule would be "IF solubility of compound is zero THEN absorption is zero." The production rules are based on rules of thumb (heuristics) and the like, and may be generated by correlation of parameters and simulation runs. Rules can be added, modified or removed to change how a simulation model responds to incoming data.

The input/output system, simulation engine and simulation model of the PK tool are capable of working together to carry out the steps of (1) receiving as input data, the initial amount of a test sample at the site of administration and in vitro bioavailability data including one or more of permeability and solubility data, and optionally dissolution rate and transfer mechanism data; and (2) applying the simulation engine and the simulation model to generate as output data a simulated in vivo absorption profile for each test sample that reflects rate, extent and/or concentration of the test sample at a given a sampling site for a selected route of administration in a mammalian system of interest. This includes uni- and multi-dimensional output profiles that collectively reflect parameters of absorption, which can be directly or indirectly utilized for characterizing in vivo absorption.

The in vitro data corresponding to test samples of the library can be empirically derived from experimental assays (e.g., physiochemical, cell or tissue assays) or theoretical data predicted from one or more other bioavailability parameters derived from the assays (e.g., calculated estimation) and/or predicted from molecular structure information (e.g., structure-property) where structural information is available. The preferred data for high-throughput screening is empirically derived cell culture-based in vitro data. Preferred data for high-resolution screening is empirically derived tissue-based in vitro data. In vivo derived mammal (animal, human) data may be employed for model development, training and/or validation purposes, as well as for predicting absorption in a first species of mammal from in vivo data derived from a second species of mammal.

Test samples of the first library can have known or unknown biological activity, and may be derived from compound libraries including natural and/or synthetic compounds and pools, as well as compound files. Libraries for high-throughput screening may range up to the maximal library size, and are preferably screened in blocks. The number of compounds or compound pools per block is determined by the user, and typically range from 1,000 to 100,000 compounds per block. Preferred libraries for high-resolution screening range from 1,000 to 10,000 compounds, more preferably from 100 to 5000 compounds, and even more preferably 50 to 1000 compounds. Of course the actual number of compounds per library and screening can vary depending on the intended end use, and may employ a combination of high-throughput and high-resolution screening approaches.

The selected routes of administration include enteral (e.g., buccal or sublingual, oral (PO), rectal (PR)), parenteral (e.g., intravascular, intravenous bolus, intravenous infusion, intramuscular, subcutaneous injection), inhalation and transdermal (percutaneous). The preferred route of administration according to the method of the invention is oral administration. The selected route of administration determines the type and/or source of assay or structure-property parameters employed for obtaining a set of in vitro bioavailability data utilized for generating a simulated in vivo absorption profile. That is, artificial, cell or tissue preparations and the like derived from or representative of a physiological barrier to absorption for a selected route of administration are chosen to generate the relevant in vitro bioavailability data for use as input into the PK tool. For instance, in vitro bioavailability data for simulating fate of a test sample following oral administration can be based on cell culture and/or tissue assays that employ biological preparations derived from or representative of the gastrointestinal tract of a mammal of interest, e.g., gastrointestinal epithelial cell preparations for permeability and transfer mechanism data, and physiological/anatomical fluid and admixing conditions corresponding to the relevant portions of the gastrointestinal tract for solubility and dissolution rate assays. Assays for collecting in vitro bioavailability data for specialized physiological barriers such as the blood brain barrier may initially assume intravascular delivery and thus instantaneous absorption as a first step. In this situation an assay is selected to generate in vitro bioavailability data relative to the blood brain barrier, which include for instance cell culture and/or tissue assays that employ biological preparations derived from or representative of the interface between systemic blood and the endothelial cells of the microvessels of the brain for a mammal of interest, e.g., blood-brain-barrier microvessel endothelial cell preparations for permeability and transfer mechanism data, and physiological/anatomical fluid and admixing conditions corresponding to the relevant portions of the blood membrane barrier for solubility and dissolution rate assays. A series of assays may be employed to collect in vitro bioavailability data for two or more barriers to absorption. As an example, oral, hepatic, systemic and blood brain barrier assays may be utilized to obtain in vitro bioavailability data for screening compound libraries for orally delivered compounds that target brain tissue.

The sampling site relates to the point at which absorption parameters are evaluated for a test sample of interest. This is the site at which rate, extent and/or concentration of a test sample is determined relative to a selected site of administration, and is separated from the site of administration by at least one physiological barrier to absorption. For generating simulated absorption profiles, the sampling site preferably is separated from the site of administration by an individual primary barrier to absorption, which can be utilized to evaluate additional absorption events by secondary barriers to absorption so as to sequentially and collectively reflect the summation of absorption events at other sampling sites of interest. As an example, the sampling site selected for oral delivery may be the portal vein where the primary barrier to absorption is the gastrointestinal lumenal membrane, or systemic blood where a secondary barrier to systemic absorption is the liver after the test sample passes from the portal vein through the liver to systemic circulation. Thus the type of physiological barrier(s) residing between a site of administration and a sampling site reflects the type of assay(s) employed for generating the desired bioavailability data for use as input data into the PK tool of the invention.

As the selected route of administration determines the barrier(s) to absorption and the physiological parameters that affect absorption events following administration, it also determines the physiologic-based pharmacokinetic simulation model employed in the PK tool for generation of the simulated in vivo absorption profile. By way of example, if the proposed route of administration is oral, then a primary barrier to absorption is the lumenal membrane of the gastrointestinal tract, and a secondary event affecting systemic bioavailability is first pass metabolism by the liver. Thus, a given simulation model and its associated parameters for simulating the fate of a compound selected for oral delivery is chosen to represent this scenario. The model would include therefore relevant components of the gastrointestinal tract for administration and absorption (i.e., stomach, duodenum, jejunum, ileum, and colon) and a primary sampling site (i.e., portal vein) from which to evaluate a primary absorption event. In this instance a secondary barrier to absorption for oral delivery is the liver and a secondary sampling site is systemic blood/plasma. This basic approach to choosing a physiologic-based pharmacokinetic model also applies to models employed to simulate absorption by target organs and the like, where a physiological barrier to absorption is the tissue and/or membrane separating systemic blood from the target organ, such as the blood brain barrier. In this situation if oral delivery is selected as the preferred route of administration for a compound targeting brain tissue, then a gastrointestinal tract model and blood brain barrier model may be implemented separately and/or combined through a complementary plasma component of the models for screening purposes.

The physiological models are selected from a repository of delivery route-specific models stored in a memory, a database, or created de novo. Physiological models of the invention include those corresponding to common routes of administration or barriers to absorption, such as oral (GI tract), ocular (eye), transdermal (skin), rectal, intravenous, rectal, subcutaneous, respiratory (nasal, lung), blood brain barrier and the like. For constructing a model de novo, the basic approach is to identify and isolate a primary barrier to a specific absorption event from secondary events so that each barrier to absorption can be tested and validated in isolation. This involves selecting a site of administration that is separated from a sampling site by a primary physiological barrier to absorption and then building a developmental physiological model that incorporates rate process relations and limitations to describe the isolated absorption event. If desired, the secondary events can be added sequentially so that each additional layer of complexity to the model can be tested and validated in isolation from other components of the initial model.

Test samples selected for their predicted/simulated in vivo absorption profile from the first library can then be utilized to generate a secondary compound library, which may be physically separate from the originating (first) compound library. The secondary library also may be defined by simply cataloging test samples in the originating library by a descriptor(s) related to their respective absorption profiles. In particular, for selecting compounds having a desired absorption profile compared to others, the profiles are compared and the compounds ranked in order of optimal to minimal concentration, rate and/or extent of absorption at a sampling site of interest, and/or one or more of absorption parameters from the group of permeability, solubility, dissolution rate, and transport mechanism. Ranking profiles can then be utilized to select compounds having a desired absorption profile, which include optimally absorbed compounds, but also may include those that are poorly absorbed. For instance, the selection can be based on choosing compounds that fall within a user defined window of absorption rate, extent of absorption and/or concentration at a selected sampling site. The user defined window can be based on ranges of concentration, rate and/or extent of absorption relative to a control or set of standard compounds having known absorption profiles for the selected route of administration. An example of a desired absorption profile includes compounds that exhibit moderate to optimal rate and/or extent of absorption for a particular barrier to absorption as compared to a control.

The secondary library can then be subjected to further rounds of bioavailability screening, including additional rounds of more focused absorption screening, as well as other screens that characterize the test samples by metabolism, toxicity, biological activity and the like. This process can be repeated one or more times to obtain libraries containing compounds that are increasingly optimized for absorption, and optionally absorption and one or more other properties.

Secondary libraries produced by the method of the invention are unique in that they contain compounds possessing a desired absorption profile as the common functional denominator for a selected route of administration, and thus substantially retain route-specific structural and functional diversity of activities and bioavailability residing in the parent library. By way of contrast, secondary libraries produced by activity screening are likely to represent reduced activity and bioavailability diversity, since compounds are selected solely to interact with specific receptor(s). Activity screens tend to select compounds with similar molecular structure, which tends to result in similar properties and therefore absorption profiles. Absorption screening selects for molecular properties and thus in more likely to maintain structural diversity. For instance, depending on the diversity of the first library, a secondary library produced according to the method of the invention will contain a variable composite of compounds or mixtures of compounds having a user defined absorption profile, compounds having low to high activity against a particular receptor, as well as compounds that exhibit no activity against that particular receptor(s). These secondary libraries also will contain optimal diversity with regard to route-specific structure-bioavailability information, which is extremely useful for subsequent structure-based compound design and iterative synthesis of analog libraries and the like.

Thus an advantage of screening compound libraries by absorption profiles is that the structural and functional activity and bioavailability diversity residing in the parent library for a selected route of administration is retained in the secondary library, although no activity or structural information is required to define the content of the new library. Another advantage is that a majority of all compounds residing in the newly created library will exhibit a user selected absorption profile, and thus the chance of identifying well absorbed leads for secondary screening by activity and other properties, and ultimately drug development, is improved. An additional advantage is that the libraries are reduced to a more manageable size for secondary screening, while retaining optimal activity diversity within the library in terms of a composite of inherent biological activities for a selected route of administration.

The present invention is significant and counterintuitive in that biological activity (i.e., receptor-interaction activity) is not required for the process, or for obtaining libraries optimized to contain compounds having improved in vivo pharmacological activity for a selected route of administration. Furthermore, screening according to the present invention increases the utility of compound libraries in general through identification of new lead drug compounds from: (1) libraries that have not been screened for activity; (2) libraries previously screened for activity that contain compounds failing to pass activity screens; and (3) libraries previously screened for activity that contain compounds failing to reach the drug development stage for lack of desired biological activity or for failing to work in a preferred route of administration or formulation. As can be appreciated, the method and libraries produced by the method of the invention increase the chances of finding better absorbed leads for drug development for a selected route of administration. The method of the invention also permits early identification of possible routes of administration for a lead compound identified by screening of an absorption library of the invention by biological activity.

Compound Library:

Compounds employed in the method of the invention may be from physical compound libraries that contain natural and/or synthetic compounds and pools. Compound files (computer-readable compound representations and theoretical "virtual" libraries) also may serve as a reservoir from which to obtain compounds for screening. Examples of natural compound libraries include those that contain compounds obtained from biological preparations, such as from microorganisms (viruses, bacteria), algae, lower plants (fungi), higher plants, lower animals, mammals and the like. Examples of synthetic libraries include those that contain compounds generated using various synthetic chemistry techniques, such as solid and/or solution phase chemistries. Synthetic libraries produced by combinatorial chemistries are of particular interest. Techniques and sources for obtaining the compound libraries are well known, and new sources and chemistries are being developed at a rapid pace. The methods of the invention are applicable for any of these libraries.

Compounds of a physical library are typically stored in multi-vessel storage and/or testing units, such as multi-well microtiter plates, as liquids or solids. In particular, compounds of a given library can reside in pools containing mixtures of two or more compounds, as extracts from biological preparations, and/or as isolated individual compounds per storage and/or test vessel of a multi-vessel storage and/or testing unit. The units may be stacked or stored in separate locations. As can be appreciated, however, individual vessels of a library do not have to be stored in the same physical location; for instance, they can be assigned to a particular library although they reside in a different storage unit and/or location. The same applies to compound files.

As an example, compound libraries may be represented as a machine-readable compound file. This includes compound files stored and/or accessible on a computer-readable medium. Examples include optical and magnetic mediums and the like. Machine-readable compound library files are particularly useful, for example, when large combinatorial libraries are screened according to the method of the invention, and then the absorption profile and/or ranking information is used to catalogue the larger library electronically without the need to go back and create a separate physical library that reflects the new library. The compound file can then be accessed to retrieve, add or change information in the file to generate new libraries and/or proceed through iterative rounds of new screening.

Historically, natural products are the most common source of new pharmaceutical and lead drug candidates. A natural product library will contain extracts of various naturally occurring substances. Common sources of the extracts are microbial sources such as various fungi, bacteria, or algae. Plant extracts are also a common component of natural product libraries. The natural product libraries are readily producible using standard methods. Natural product libraries also are commercially available. For instance, natural product libraries can be obtained from a variety of commercial venders, such as Pan Laboratories (Bothell, Wash.) and MycoSearch (NC).

In contrast to natural product libraries, synthetic compound libraries are composed of chemicals that are not necessarily natural. Synthetic compound libraries suitable for the present intention include libraries constructed de novo or obtained commercially. Any number of methods for constructing synthetic compound libraries can be utilized. Synthetic compound libraries also are commercially available from various sources. Examples of commercial sources for synthetic libraries include Maybridge Chemical Co. (Trevillet, Cornwall, UK), Comgenex (Princeton, N.J.), Brandon Associates (Merrimack, N.H.), and Microsource (New Milford, Conn.). In addition, a "rare chemical" library can be obtained from Aldrich Chemical Company, Inc. (Milwaukee, Wis.).

Compounds from both natural product and synthetic compound libraries are readily modified through conventional chemical, physical, and biochemical methods (Blondelle et al., TIBTech (1996) 14:60).

Of particular interest are synthetic compound libraries produced through combinatorial chemistry, referred to as combinatorial libraries. Combinatorial chemistry is a technique of creating large libraries of diverse compounds through systematic and repetitive use of chemical building blocks or templates. The combinatorial libraries may be based on any number of templates or core molecules modified by addition of constituents. For instance, combinatorial libraries may include isolated or mixtures of peptide, oligonucleotide, and drug-like small molecules, or combinations thereof, such as those generated by pin technology and split-pool methods. Examples include peptides, peptidomimetics, cyclic peptides, constrained peptides, small non-peptide organics, nucleic acids, chiral and non-chiral compounds, drug-like small molecule libraries and the like.

Combinatorial libraries can be made de novo or obtained commercially. Virtually an unlimited number of techniques can be used to create a combinatorial library, such as solution and solid phase chemistries. An advantage of solution-phase synthesis is that it capitalizes on the vast range of solution chemistry available in the chemical literature. Solid-phase synthesis is useful for facile purification and easier automation. For instance, combinatorial chemistry libraries can be produced by semi- of fully-automatic equipment available from various sources following manufactures protocols. Examples include Hewlett-Packard (Palo Alto, Calif.), Perkin-Elmer Applied Biosystems (Foster City, Calif.) or ChemTech (Louisville, Ky.). These types of equipment are compatible with a wide variety of coupling chemistries. Combinatorial libraries also can be made-to-order or purchased commercially. Examples of commercial venders include Affymax (Palo Alto, Calif.), ArQule (Medford, Mass.), Helios Pharmaceuticals (Louisville, Ky.), Gryphon Sciences (So. San Francisco, Calif.).

Additional compound libraries include compound file libraries. Compound files are databases containing one-dimensional, two-dimensional or three-dimensional descriptions of chemical compounds. These libraries can be created to describe any chemical compound. For example, there are several commercial sources of both two-dimensional (e.g., from Maybridge Chemical Company, Bark Information Services, or the National Cancer Institute) and three-dimensional (e.g., the Cambridge Small Molecule Library) compound files. Alternatively, these compound files can be easily created based on known chemical formulas and the basic chemical knowledge, such as standard atoms, bond angles and lengths and the like.

Virtual compounds are of interest as they can be exploited using computer methods to design, select and iteratively refine compound libraries of small molecule drugs from structure-bioavailability data, structure-activity relationship (SAR) data or three-dimensional structural or pharmacophore models having known and/or predicted bioavailability profiles. An important feature of the process is the initial computer generation of very large virtual libraries of synthetically accessible compounds. These compounds are designed to explore specific structural features suggested from an input SAR or structural model. Any number of suitable computer systems can be utilized for this purpose. Virtual libraries typically contain 100,000 to 1,000,000 compounds where each compound has a validated chemical synthesis pathway, and is characterized by a set of molecular descriptors. Computer codes are then used to select library sub-sets (100–1000 compounds) for rounds of automated synthesis and testing using high-throughput absorption screening according to the method of the invention. Any number of approaches can be employed for coding. Test data resulting from absorption screening for a given round of synthesis are interpreted by a computer selector code that is able to optimize multiple objectives simultaneously, in order to refine the properties of molecules selected in further rounds of synthesis and testing. Such a screening approach can be implemented through a hierarchical computer system (e.g., client-server, mainframe, real time system) that tracts compounds from virtual conception through to testing and compound file database registration. This approach is extremely useful for creating new structure-bioavailability data from analysis of both positive and negative absorption profiles for a test sample, e.g., structural differences that contribute to good versus poor absorption.

Assays for Generating Bioavailability Data:

In vitro bioavailability data utilized to generate an absorption profile for a test sample include permeability and solubility parameters, and optionally transport mechanism and dissolution parameters. Bioavailability data can be generated de novo following any number of techniques, or obtained from public or existing sources where available. The bioavailability data can be derived from chemical, and/or biological assays as well as theoretical predictions. By way of example, the in vitro assays may employ artificial (synthetic) or naturally occurring biological preparations. This includes chemcial, cell and/or tissue preparations. Assays for generating in vitro bioavailability data involve screening a plurality of test samples containing isolated compounds and/or isolated mixtures of compounds per test sample in an assay characterized by measurement of (1) permeability and optionally transport mechanism for a test sample; and (2) solubility and optionally dissolution for a test sample. Methods and materials for performing the assays are based on the selected route of administration, the associated barrier(s) to absorption and proposed sampling site(s). For instance, if oral delivery is proposed for simulation and an initial sampling site is selected to be the portal vein (so as to isolate gastrointestinal absorption events from hepatic metabolism) then bioavailability data is collected from an in vitro assay that best approximates the luminal barrier and segmental physiology of the gastrointestinal tract.

Examples of some common cell and tissue sources for permeability and transport mechanism assays for a selected route of administration are provided below in Table 1.

TABLE 1

Permeability and Transport Mechanism.

| Route/Tissue | Cell Culture |
|---|---|
| Oral/Intestinal | Caco-2 cells |
|  | HT-29 cells |
|  | T84 cells |
|  | Intestinal epithelial cells (IEC) |
|  | SV40 T Immortalized cells |
|  | Organ culture/co-culture |
|  | Primary culture |
| Inhalation/Nasal | SV40 T immortalized cells |
|  | Primary culture |
| Ocular/Corneal | RCE1 cells |
|  | Primary cultures |
|  | SV40 T immortalized cells |
| Oral-Buccal/Cheek | Primary cultures |
| Topical/Transdermal | HaCat cells |
|  | Primary/co-cultures |
| IV/Hepatic | Hepatic carcinoma cell lines |
|  | Primary cultures |
|  | Co-cultures |
|  | SV40 T immortalized cells |
| IV/Blood Brain Barrier | Primary culture |
|  | SV40 immortalized cells |

Examples of some common parameters for solubility and dissolution assays for a given route of administration are provided below in Table 2.

TABLE 2

Solubility and Dissolution Parameters.

| Route/Anatomy/Physiology | | In vitro Parameters |
|---|---|---|
| Oral | Gastrointestinal (GI) tract | pH |
|  | Stomach | Temperature |
|  | Duodenum | Concentration of test sample |
|  | Jejunum | Volume |
|  | Ileum | Osmotic pressure |
|  | Colon | Admixing conditions |
| Buccal/Sublingual | Mouth | Physiologic Fluid/Buffer/solvent system |
|  | Cheek | Excipients |
|  | Tongue | Other Additives |
| Rectal | Lower GI tract | Test chamber composition |
|  | Colon | |
|  | Rectum | |
| Parenteral | Skin | |
|  | Muscles | |
|  | Veins | |

TABLE 2-continued

Solubility and Dissolution Parameters.

| Route/Anatomy/Physiology | | In vitro Parameters |
|---|---|---|
| Aerosol | Respiratory system | |
| | Nose | |
| | Lungs | |
| | Mouth | |
| Transdermal | Skin | |
| | Topical | |
| | Ear | |

In vitro and in vivo techniques for collecting permeability and transport mechanism data using cell- and/or tissue-based preparation assays are well known in the art (Stewart et al., Pharm. Res. (1995) 12:693–699; Andus et al., Pharm. Res. (1990) 435–451; Minth et al., Eur. J. Cell. Biol. (1992) 57:132–137; Chan et al., DDT 1(11):461–473). For instance, in vitro assays characterizing permeability and transport mechanisms include in vitro cell-based diffusion experiments and immobilized membrane assays, as well as in situ perfusion assays, intestinal ring assays, intubation assays in rodents, rabbits, dogs, non-human primates and the like, assays of brush border membrane vesicles, and everted intestinal sacs or tissue section assays. In vivo assays for collecting permeability and transport mechanism data typically are conducted in animal models such as mouse, rat, rabbit, hamster, dog, and monkey to characterize bioavailability of a compound of interest, including distribution, metabolism, elimination and toxicity. For high-throughput screening, cell culture-based in vitro assays are preferred. For high-resolution screening and validation, tissue-based in vitro and/or mammal-based in vivo data are preferred.

Cell culture models are preferred for high-throughput screening, as they allow experiments to be conducted with relatively small amounts of a test sample while maximizing surface area and can be utilized to perform large numbers of experiments on multiple samples simultaneously. Cell models also require fewer experiments since there is no animal variability. An array of different cell lines also can be used to systematically collect complementary bioavailability data related to a series of transport barriers (passive paracellular, active paracellular, carrier-mediated influx, carrier-mediated efflux) and metabolic barriers (protease, esterase, cytochrome P450, conjugation enzymes).

Cells and tissue preparations employed in the assays can be obtained from repositories, or from any higher eukaryote, such as rabbit, mouse, rat, dog, cat, monkey, bovine, ovine, porcine, equine, humans and the like. A tissue sample can be derived from any region of the body, taking into consideration ethical issues. The tissue sample can then be adapted or attached to various support devices depending on the intended assay. Alternatively, cells can be cultivated from tissue. This generally involves obtaining a biopsy sample from a target tissue followed by culturing of cells from the biopsy. Cells and tissue also may be derived from sources that have been genetically manipulated, such as by recombinant DNA techniques, that express a desired protein or combination of proteins relevant to a given screening assay. Artificially engineered tissues also can be employed, such as those made using artificial scaffolds/matrices and tissue growth regulators to direct three-dimensional growth and development of cells used to inoculate the scaffolds/matrices.

Epithelial and endothelial cells and tissues that comprise them are employed to assess barriers related to internal and external surfaces of the body. For example, epithelial cells can be obtained for the intestine, lungs, cornea, esophagus, gonads, nasal cavity and the like. Endothelial cells can be obtained from layers that line the blood brain barrier, as well as cavities of the heart and of the blood and lymph vessels, and the serious cavities of the body, originating from the mesoderm.

One of ordinary skill in the art will recognize that cells and tissues can be obtained de novo from a sample of interest, or from existing sources. Public sources include cell and cell line repositories such as the American Type Culture Collection (ATCC), the Belgian Culture Collections of Microorganisms (BCCM), or the German Collection of Microorganisms and Cell Cultures (DSM), among many others. The cells can be cultivated by standard techniques known in the art.

Preferred assays for collecting permeability data utilize devices and methods that measure change in resistance or conductivity of a membrane system by ion flux. Any device suitable for such studies can be employed. These include voltage-clamp type devices and methods that employ either cell cultures or precision tissue slices. Diffusion chamber systems utilizing cultured cells grown on permeable supports to measure permeability are preferred. More preferred devices are readily adapted for high-throughput and automated screening. Examples of such devices are known and exemplified in U.S. Pat. No. 5,599,688; WO 96/13721; and WO 97/16717. These devices also can be adapted for examining transport mechanisms. As can be appreciated, however, measurement of resistance, conductivity and/or ion flux is not required to determine permeability of compounds. Many other techniques are available and can be employed in the invention. For instance, permeability data also may be predicted using theoretical models to approximate this parameter, for example, from SAR/QSAR (e.g., log P, molecular weight, H-bonding, surface properties).

Transport mechanism of a test sample of interest can be determined using cell cultures and/or tissue sections following standard techniques. These assays typically involve contacting cells or tissue with a compound of interest and measuring uptake into the cells, or competing for uptake, compared to a known transport-specific substrate. These experiments can be performed at short incubation times, so that kinetic parameters can be measured that will accurately characterize the transporter systems, and minimize the effects of non-saturating passive functions. (Bailey et al., Advanced Drug Delivery Reviews (1996) 22:85–103); Hidalgo et al., Advanced Drug Delivery Reviews (1996) 22:53–66; Andus et al., Pharm. Res. (1990) 7(5):435–451). For high-throughput analyses, cell suspensions can be employed utilizing an automated method that measures gain or loss of radioactivity or fluorescence and the like such as described in WO 97/49987.

In a preferred embodiment, transport mechanism is determined using high-throughout transporter screening cell lines and assays. In this aspect of the invention a cell line is selected and/or manipulated to over-express one or more transporter proteins, and/or enzymes. The cells are then used to rapidly identify the mechanism(s) by which a compound is transported across the physiological barrier of interest. Transporters of interest represent the basic categories of transport including uptake and efflux transporters. These transporters aid in the movement of materials in biological systems, into and out of cells and across cellular layers. Natural combination(s) of enzyme(s) and transporter(s) also can provide the basis of a high-throughput transport mechanism screening assay. For instance, certain enzymes or transporters require secondary enzymes or transporters to function in a normal physiological mode, i.e., cytochrome P4503A is co-regulated with P-glycoprotein. These proteins share the same substrate and their genes are co-regulated. Thus multiple artificial combination(s) of transporter(s) and enzyme(s) can be employed for characterizing transport mechanism of a test sample of interest. Examples of possible combinations of a transporter and/or enzyme in a host cell of interest include cell-transporter-enzyme, cell-transporter, cell-enzyme, cell-enzyme-enzyme, and cell-transporter-transporter. Examples of transporters that can be used to transfect the host cell of interest include peptide transporters (PepT1), amino acid transporters, organic cation transporters (OCT1), organic anion transporters, nucleotide transporters (N1, N2, N3, ES, EI), glucose transporters (SGLT1, GLUT 1 through GLUT 7), monocarboxylate transporters (MCT1), and multi-drug transporters (LRP, MDR, MRP, PGP). Examples of enzymes that can be used to transfect the host cell are Phase I and II enzymes, cytochrome P450, 3A, 2D and the like.

Nucleic acid and/or amino acid sequences for transporters/enzymes can be identified in various genomic and protein related databases. Examples of publicly accessible databases include as GenBank (Benson et al., *Nucleic Acids Res* (1998)26(1):1–7; USA National Center for Biotechnology Information, National Library of Medicine, National Institutes of Health, Bethesda, Md., USA), TIGR Database (The Institute for Genomic Research, Rockville. Md.. USA), Protein Data Bank (Brookhaven National Laboratory, USA), and the ExPASy and Swiss-Protein database (Swiss Institute of Bioinformatics, Geneve, Switzerland).

Any number of known techniques can be used to prepare nucleic acid encoding a transporter(s) and/or enzyme(s) of interest. To express a target protein in a host cell the nucleotide sequence coding for the polypeptide is inserted into an appropriate expression vector, i.e., a vector that contains the necessary elements for the transcription and translation of the inserted coding sequence. The host cell line can be stably or transiently transfected by methods known in the art. Examples of transient transfection methods include calcium phosphate, electroploration, lipofectamine, and DEAE dextran. A cell line can be stably transfected using methods known in the art such as calcium phosphate. In addition, the host cell can be infected with a retrovirus containing a target protein of interest, resulting in stable expression of the desired target protein. Host cells that express the target gene product can be identified by standard techniques. These include, but are not limited to, detection of the protein as measured by immunoprecipitation and Western blot analysis or by measuring a specific biological response.

For synthesis in a cell, a target transporter/enzyme protein can be generated by standard techniques. Cells that naturally express a target protein can be employed. Transfection and transformation of a host cell with DNA encoding a protein of interest also can be used. For example, a polymerase chain reaction (PCR) based strategy may be used to clone a target DNA sequence encoding all or part of a target membrane polypeptide of interest. (See, e.g., "PCR Cloning Protocols: From Molecular Cloning to Genetic Engineering," B. A. White, ed., Humana Press, Methods in Molecular Biology, Vol. 67, 1997). For example, PCR can be used for cloning through differential and subtractive approaches to cDNA analysis, performing and optimizing long-distance PCR, cloning unknown neighboring DNA, and using PCR to create and screen libraries. PCR also can be used to introduce site-specific and random mutations into DNA encoding a target protein of interest.

For general cloning purposes, complementary and/or degenerate oligonucleotides corresponding to conserved motifs of the target membrane polypeptide may be designed to serve as primers in a cDNA and/or PCR reaction. Templates for primer design can be obtained from any number of sources. For example, sequences, including expressed sequence tags (ESTs) can be obtained from various databases, such as GenBank, TIGR, ExPASy and Swiss-Protein databanks. Homology comparisons performed using any one of a number of alignment readily available programs that employ search engines to find the best primers in a sequence based on various algorithms. Any number of commercially available sequence analysis packages, such as Lasergene, GeneWorks, DNASIS, Gene Jockey II, Gene Construction Kit, MacPlasmap, Plasmid ARTIST, Protein Predictor, DNA/RNA Builder, and Quanta. (See, e.g., "Sequence Data Analysis Guidebook," Simon R. Swindell, ed., Humana Press, 1996). The information can be used to design degenerate primers, nested/multiplex primers, site-directed mutagenesis, restriction enzyme sites etc. Primers can be designed from homology information, and computer programs can be used for primer design as well. Examples include "Primer Premier 4.0" for automatic primer selection (CloneTech, Inc.). The amplified cDNA and/or PCR fragment may be used to isolate full-length clones by radioactive or non-radioactive labeling of the amplified fragment and screening a library.

Alternatively, transporter/enzyme DNA cloned from one source may be utilized to obtain a corresponding DNA sequence from other sources. Specifically, a genomic and/or cDNA library constructed from DNA and/or RNA prepared from a cell known or expected to express the target transporter/enzyme may be used to transform a eukaryotic or prokaryotic host cell that is deficient in the putative gene. Transformation of a recombinant plasmid coding for the protein into a deficient host cell would be expected to provide the cell with a complement product corresponding to the protein of interest. In some cases, a host cell can be selected to express a particular phenotype associated with the target polypeptide and thus may be selected by this property. For a review of cloning strategies which may be used, see e.g., Sambrook et al., 1989, Molecular Cloning, A Laboratory Manual, Cold Springs Harbor Press, New York; and Ausubel et al., 1989, Current Protocols in Molecular Biology, Green Publishing Associates and Wiley Interscience, New York.

To express a target transporter/enzyme in a host cell the nucleotide sequence coding for the protein, or a functional equivalent for modular assembly as described above, is inserted into an appropriate expression vector, i.e., a vector which contains the necessary elements for the transcription and translation of the inserted coding sequence. Host cells containing the coding sequence and that express the target gene product may be identified by standard techniques. For example, these include but are not limited to DNA-DNA or DNA-RNA hybridization; the presence or absence of "marker" gene functions; assessing the level of transcription as measured by the expression of mRNA transcripts in the host cell; and detection of the gene product as measured by immunoassay or by its biological activity.

Once a clone producing the target transporter/enzyme is identified, the clone may be expanded and used to over express the protein(s). If desired, the proteins may be purified using techniques well-known in the art including, but not limited to immunoaffinity purification, chromatographic methods including high performance liquid chromatography or cation exchange chromatography, affinity chromatography based on affinity of the polypeptide for a particular ligand, immunoaffinity purification using antibodies and the like. The purified proteins can then be bound to an artificial membrane matrix and utilized for assessing interaction of compounds to the transporter/enzyme of interest.

Some commonly used host cell systems for expression of transport proteins and enzymes include *E. coli*, Xenopus oocytes, baculovirus, vaccinia, and yeast, as well as many higher eukaryotes including transgenic cells in culture and in whole animals and plants. (See, e.g., G. W. Gould, "Membrane Protein Expression Systems: A User's Guide," Portland Press, 1994, Rocky S. Tuan, ed.; and "Recombinant Gene Expression Protocols," Humana Press, 1996). For example, yeast expression systems are well known and can be used to express and recover target transporter/enzyme systems of interest following standard protocols. (See, e.g., Nekrasova et al, *Eur. J. Biochem.* (1996) 238:28–37; Gene Expression Technology Methods in Enzymology 185: (1990); Molecular Biology and Genetic Engineering of Yeasts CRC Press, Inc. (1992); Herescovics et al., FASEB (1993) 7:540–550; Larriba, G. Yeast (1993) 9:441–463; Buckholz, R. G., *Curr Opinion Biotech* (1993) 4:538–542; Mackett, M, "Expression of Membrane Proteins in Yeast Membrane Protein Expression Systems: A Users Guide," pp. 177–218, Portland Press, (1995).

For high-resolution screening and validation, tissue-based assays may be employed to characterize transport mechanisms. For example, of the cytochrome P450 superfamily, CYP3A enzymes represent the most abundant isoforms in the liver and they are responsible for the metabolism of compounds of diverse chemical structure. The uptake of a compound into hepatocytes can be mediated by passive or carrier processes. Once in the parenchymal cell of the liver, the drug can be metabolized or bind to intracellular proteins. The drug or its metabolite(s) may return to the circulation or exit from the hepatocyte into the bile canaliculus, again by passive or carrier-mediated transport, before secretion in bile. Experimental systems have been devised to study these processes in isolation. Examples of such systems include isolated perfused rat liver (IPRL), and bile duct cannulated (BDC) rat models. (Chan et al., DDT (1996) 1:461–473).

Tissue from transgenic animals designed to express particular transport properties in one or more particular tissues also may be utilized to characterize transport mechanisms. In this aspect of the invention, an animal can be genetically manipulated to express or not express one or more specific proteins in a tissue of interest, e.g. transporter protein in duodenum tissue. Tissue from the genetically engineered animal can then be used to examine transport mechanisms in a tissue-based assay. Transgenic animal methodologies are well known (Gordon et al., Hum. Cell (1993) 6(3):161–169; and Jaenisch, R., Science (1998) 240:1468–1474).

Artificially engineered tissue also can be used for permeability assays, such as tissues generated ex vivo for use as skin grafts, transplants, and the like. Such tissues can be obtained using standard techniques. See, for example, U.S. Pat. Nos. 5,759,830; 5,770,193; and 5,770,417.

Solubility and dissolution data can be obtained in an in vitro assay by testing each sample of interest in an appropriate physiologic fluid/buffer system that best approximates the particular physiological system selected as the barrier to absorption. A solubility profile is a plot of solubility of a test sample at various physiological conditions. As an example, the natural pH environment of the gastrointestinal tract varies from acidic in the stomach to slightly alkaline in the small intestine and fluid composition for each segment may vary as well. The solubility profile provides an estimation of the completeness of dissolution of a test sample in a particular physiological compartment or anatomical entity. In this instance, a panel of test wells each having different pHs and physiological fluid composition can be employed to generate a solubility profile for each test sample. Solubility and dissolution data can also be predicted using theoretical models to approximate these values, for example, from SAR/QSAR information.

In vitro dissolution assays measure the rate and extent of dissolution of a test sample in an aqueous solution. Various parameters are considered when performing a dissolution assay and are well known in the art. These parameters include size of the experimental vessel, amount of agitation and nature of the stirrer, temperature and nature of the dissolution medium, pH, viscosity, and design of the dissolution apparatus. Standard methods known in the art for measuring dissolution include rotating basket, paddle, rotating bottle, flow-through dissolution, intrinsic dissolution, and peristalsis methods. These methods can be adapted and used as a guide for high-throughput solubility and dissolution screening.

For high-throughput collection of solubility and dissolution data, automated methods of solid and liquid handling are employed. This method involves addition of samples to a multi-well or multi-tube/plate system. The data associated with these tubes/plates, such as physiologic fluid/buffer system, volume, concentration, pH and tube/plate maps, is transferred into an inventory system. The inventory system generates codes containing updated information pertaining to the aliquoting, diluting, or pooling methods applied to the original tubes/plates. Tasks created in the database are then carried out physically in coded tubes/plates. Aliquots are then distributed to designated screen sites. After testing, the solubility profiles are generated and ported to a database for access and analysis.

Assays for Screening Secondary Absorption Libraries:

Secondary libraries selected for absorption also can be characterized by one or more additional properties including, but not limited to, metabolism, distribution, elimination, toxicity, and biological activity. As with absorption, assays to characterize the relevant data are based on the selected route of administration. Metabolism or biotransformation refers to the biochemical transformation of a compound to another chemical form. The biotransformation process typically results in a metabolite that is more polar (water-soluble) than the original parent molecule.

Most tissues have some metabolizing capacity but the liver is by far the most important organ, on the basis of size if not always concentration of target compound metabolizing enzyme. Phase I reactions are defined as those that introduce a functional group to the molecule and phase II reactions are those that conjugate those function groups with endogenous moieties.

Since metabolism is a drug clearance process, metabolism of a compound contributes to elimination of the compound. Thus, compounds selected for absorption can be screened for metabolism in order to consider disposition of a drug after or concurrent with administration using standard techniques known in the art. (See, e.g., Sakuma & Kamataki, Drug metabolism research in the development of innovative drugs, In: Drug News & Perspectives (1994) 7 (2):82–86).

Metabolism assays for high-throughput screening preferably are cell-based (cells and cellular preparations), whereas high resolution screening can employ both cell and tissue-based assays. In particular, test samples from compound libraries can be screened in cell and tissue preparations derived from various species and organs. Although liver is the most frequently used source of cells and tissue, other human and non-human organs, including kidney, skin, intestines, lung, and blood, are available and can be used to assess extra-hepatic metabolism. Examples of cell and tissue preparations include subcellular fractions (e.g., liver S9 and microsomes), hepatocytes (e.g., collagenase perfusion, suspended, cultured), renal proximal tubules and papillary cells, re-aggregate brain cells, bone marrow cell cultures, blood cells, cardiomyocytes, and established cell lines as well as precision-cut tissue slices.

Examples of in vitro metabolism assays suitable for high-throughput screening include assays characterized by cytochrome P450 form-specific metabolism. These involve assaying a test compound by P450 induction and/or competition studies with form-specific competing substrates (e.g., P450 inhibitors), such as P450 enzymes CYP1A, 2A6, 2C9, 2C19, 2D6, and 2E1. Cells expressing single or combinations of these or other metabolizing enzymes also may be used alone or in combination with cell-based permeability assays. A high-throughput cell-based metabolism assay can include cytochrome P450 induction screens, other metabolism marker enzymes and the like, such as with measurement of DNA or protein levels. Suitable cells for metabolism assays include hepatocytes in primary culture. Computer-implemented systems for predicting metabolism also may be employed.

Absorption libraries also may be characterized by additional distribution and elimination events. In this aspect of the invention, in vitro assays are performed to assess protein binding to a test compound, since protein binding can affect compound distribution and elimination. In general, it is free compound that diffuses into cells and tissues. Binding can be classified as restrictive or permissive with regard to elimination, or quantitatively defined in terms of affinity. Affinity of the binding is defined as low or high when reversible, or more unusually when irreversible binding occurs. The biological half-life of a test compound will increase due to its interaction with a protein. Usually, the higher the affinity the lower the elimination that may be observed. Albumin is by far the most frequent contributors to plasma protein binding since it comprises about one half of the total plasma proteins. The al-Acid glycoprotein also plays an important role in the protein binding of a compound since it has an affinity for bases (many drugs are weak bases). It is an acute phase reactant and its concentration rises in inflammatory processes, malignant disease and stress. Lipoproteins (HDL, LDL or VLDL) bind drugs that are highly liposoluble and a fairly specific ligand-protein interaction occurs between certain steroids and gamma globulins. Thus, in vitro protein binding assays that employ one or more of albumin, al-acid glycoprotein, lipoprotein, steroid and gamma globulins may be utilized to collect distribution and elimination data that can be utilized to further characterize an absorption library.

Similarly, toxicity of a test compound may also be assayed and used to characterize compounds of an absorption library. Any number of techniques in the art may be employed for this purpose. Preferred methods are in vitro. Examples include determination of toxicity mechanisms, determination of cytotoxic potentials in cell and tissues of target organs, estimation of therapeutic indices from in vitro data, cytotoxicity screening of closely related drug compounds in cells from the same mammal or from different species, detection and quantification of peroxisome proliferation, screening of agents to prevent or reverse cytotoxicity, and specialized studies on target cells using co-incubation systems, e.g., red blood cells and hepatocytes.

Toxicity assays may utilize any technique that provides a toxicity parameter as an endpoint. For high-throughput screening, cell based assays are preferred. This includes gene expression (e.g., protein or nucleic acid based) enzymatic activity, and morphology screens and the like. Examples of cell-based assays include in vitro peroxisome proliferation studies, which can be used to assay palmitoyl CoA-oxidation in primary hepatocyte culture, with or without concurrent measurement of DNA or protein levels. Cytotoxicity assays in primary cultures also can be utilized, and include screening for cytotoxicity in hepatocytes or renal proximal tubules, enzyme release (lactate dehydrogenase), and MTT conversion (mitochondrial function) following standard techniques. Computer-implemented SAR/QSAR models for predicting toxicity also may be employed, such as when structural information is available.

Absorption libraries produced according to the method of the invention also may be examined for activity hits using any technique suitable for such purpose. Examples include screening of isolated receptors or use of cellular preparations that contain a receptor target of interest (i.e., compound/ligand-receptor interaction/binding). These include reporter gene assays, binding assays, cellular proliferation assays and the like. (See, e.g., Wallace, R. W., and Goldman, M. E., Bioassay Design and Implementation, High Throughput Screening, (1997) p. 279–328, Ed. Devlin, J P). Activity assays also may use SAR/QSAR models.

Screening of secondary absorption libraries by one or more of such additional properties can be performed concurrently or following the initial absorption screen of a primary compound library.

PK Tool and System:

The PK tool of the invention is utilized to generate a simulated in vivo absorption profile from in vitro solubility and permeability data, and optionally in vitro dissolution rate and transport mechanism data for a test sample of a compound library. The PK tool includes as computer-readable components, an input/output system suitable for data input and data output, a simulation engine having a numerical-based differential equation solver, and a simulation model comprising a pharmacokinetic model of the mammalian system to be simulated. In vitro bioavailability data is provided through the input/output system, and then the simulation engine and simulation model are applied to facilitate a simulation run so as to generate a user selected in vivo absorption profile for the test sample. Together, the simulation engine and simulation model are employed to simulate the fate of a test sample in the system under investigation.

The PK tool is based on a compartment-flow simulation model system. The compartment-flow model employs compartments, flow regulators, and converters that collectively regulate flow among the compartments. The model components are represented by a series of differential equations which when run through the simulation engine are solved at each time increment dt based on the initial underlying values of the equations, the input values supplied by the user, and calculations performed by various subsystems of the model when activated in a particular scenario.

The PK tool optionally comprises a repository of different pharmacokinetic models and initial parameter values for a given model. The repository preferably resides in a database of the PK tool, and/or is accessible through an acquisition model. The PK tool also may include one or more curve-fitting algorithms for generation of absorption parameters and constants for correlation of in vitro data to in vivo data, or in vivo data from one species of a mammal to in vivo data of a second species of mammal based on a selected route of administration.

1. Input/Output System

With regard to the components of the PK tool, the input/output system provides a user interface between the user and the PK tool of the invention. The input/output system may be any suitable interface for input and output of data and other information, and for operable interaction with a simulation engine and a simulation model. The input/output system preferably provides an interface for a standalone computer or integrated multi-component computer system having a data processor, a memory, and a display. Input into the method and PK tool of the invention is in vitro bioavailability data derived from an assay corresponding to a selected route of administration and mammalian system of interest. For example, the user enters the initial parameter values for a test sample, such as dose, permeability, solubility, and the like, and then optionally indicates the transport mechanism, e.g., passive transcellular, passive paracellular, carrier-mediated influx, or carrier-mediated efflux. When transport mechanism is not indicated, the PK tool can be designed to employ a default transport mechanism, such as passive transcellular. Data may be entered numerically, as a mathematical expression or as a graph that represents a physiological or pharmacokinetic parameter, or alpha such as transcellular, paracellular, passive, active, etc. An advantage of entering data as a graph is that it removes any requirement to define the mathematical relationship between a dependent and an independent variable. The interface output displays and/or compares parameters related to absorption, such as graphs or tables corresponding to rate of absorption, extent of absorption, and concentration profiles, and the like. Output of the method and PK tool is utilized to profile and rank the test sample by one or more selected absorption parameters.

The absorption parameters of a profile include concentration, rate and/or extent of absorption of a test sample. As can be appreciated, absorption parameters can be represented in multiple different ways that relate time, mass, volume, concentration variables, fraction of the dose absorbed and the like. Examples include rate "dD/dt" and "dc/dt" (e.g., mass/time-mg/hr, concentration/time-$\mu$g/ml·hr), concentration "C" (e.g., mass/volume-$\mu$g/ml), area under the curve "AUC" (e.g., concentration·time, $\mu$g·hr/ml), and extent/fraction of the dose absorbed "F" (e.g., no units, 0 to 1). Other examples include the maximum concentration ($C_{max}$), which is the maximum concentration reached during the residence of a compound at a selected sampling site; time to maximum concentration ($T_{max}$), which is the time after administration when the maximum concentration is reached; and half-life ($t_{1/2}$), which is the time where the concentration reaches ½ its maximum at a selected sampling site. Other examples of output include individual simulated parameters such as permeability, solubility, dissolution, and the like for individual segments, as well as cumulative values for these and/or other parameters.

2. Simulation Engine

The simulation engine comprises a differential equation solver. The simulation engine also may include a system control statement module when control statement rules such as IF . . . THEN type production rules are employed. The differential equation solver uses standard numerical methods to solve the system of equations that comprise a given simulation model. These include algorithms such as Euler's and Runge-Kutta methods. Such simulation algorithms and simulation approaches are well known (See, e.g., Acton, F. S., *Numerical Methods that Work*, New York, Harper & Row (1970); Burden et al., *Numerical Analysis,* Boston, Mass., Prindle, Weber & Schmidt (1981); Gerald et al.. Applied Numerical Analysis, Reading, Mass., Addison-Wesley Publishing Co., (1984); McCormick et al., Numerical Methods in Fortran, Englewood Cliffs, N.J., Prentice Hall, (1964); and Benku, T., The Runge-Kutta Methods. BYTE Magazine, April 1986, pp. 191–210).

Many different numerical schemes exist for the evaluation of the differential equations. There are literally 100's of schemes that currently exist, including those incorporated into public commercially available computer applications, private industrial computer applications, private individually owned and written computer applications, manual hand-calculated procedures, and published procedures. With the use of computers as tools to evaluate the differential equations, new schemes are developed annually. The majority of the numerical schemes are incorporated into computer applications to allow quick evaluation of the differential equations.

Computer application or programs described as simulation engines or differential equation solver programs can be either interpretive or compiled. A compiled program is one that has been converted and written in computer language (such as C++, or the like) and are comprehendible only to computers. The components of an interpretive program are written in characters and a language that can be read and understood by people. Both types of programs require a numerical scheme to evaluate the differential equations of the model. Speed and run time are the main advantages of using a compiled rather than a interpretive program.

A preferred simulation engine permits concurrent model building and simulation. An example is STELLA® (High Performance Systems, Inc.). STELLA® is an interpretive program that can use three different numerical schemes to evaluate the differential equations: Euler's method, Runge-Kutta 2, or Runge-Kutta 4. Kinetica® (InnaPhase, Inc.) is another differential equation solving program that can evaluate the equations of the model. By translating the model from a STELLA® readable format to a Kinetica® readable format, physiological simulations can be constructed using Kinetica®, which has various fitting algorithms. This procedure can be utilized when the adjustment parameters are being optimized in a stepwise fashion.

3. Simulation Model

The simulation model is a mathematical model of a multi-compartment physiological model of a mammalian system (e.g., GI tract) that corresponds to the selected route of administration (e.g., oral). A given physiological model is represented by series of differential equations that describe rate process interactions among anatomical segments for the physiological system under investigation. The individual segments or compartments are represented mathematically as a one, two and/or three compartment kinetic system. The segments are linked in a stepwise fashion so as to form an integrated physiological model describing absorption of a compound relative to the anatomical segments and at least one sampling site for assessing an absorption event in isolation. For a model simulating oral delivery, anatomical segments of the GI tract are provided, which can include the stomach, duodenum, jejunum, ileum and colon. A sampling site for the GI tract may be the portal vein and/or plasma. The rectum and colon would be applicable for modeling a rectal route of delivery. Segments and sampling site for buccal or sublingual delivery routes can include the mouth, cheek/tongue tissue and plasma. For ocular routes, this can include aqueous humor, conjunctival sac, tear duct, nasal cavity and plasma. For the lung routes, this can include respiratory bronchioles zone and plasma. For delivery via the nose, this can include nasal cavity and plasma. For the topical and transdermal routes, this can include epidermal, dermal, subcutaneous tissue, muscle and plasma. Other systems adhere to these basic designs.

Of course compartments representing a particular anatomical segment can be added or removed depending on the model's intended end use, such as when an isolated segment is examined, or when it is desired to account for parameters affecting bioavailability at additional sampling sites. For example, compartments can be added to account for both pre- or post-absorptive protein binding or complex formation to account for reversible association of a compound to the proteins (albumin and al-acid glycoprotein) of blood, or more usually plasma. Other compartments of that may be added would include those that account for phase I and/or phase II hepatic metabolism. Formulation compartments that account for variable compound formulations also can be added, such as time-release, extended release or otherwise controlled release formulations. Another example is inclusion of kidney compartments to account for renal clearance.

The compartments can be modified by factors that influence absorption such as mass, volume, surface area, concentration, permeability, solubility, fluid secretion/absorption, fluid transit, mass transit and the like, depending on the physiological system under investigation. As a rule of thumb, compartment modifiers relate to input variables. For instance, where transport mechanism and dissolution rate are variables considered for generating an absorption profile, then the physiological model will include compartments and parameters that account for these variables.

When represented as a compartment-flow simulation model, the anatomical segments of a physiological model typically include one or more central and peripheral compartments that reversibly communicate through a flow regulator. A central compartment represents the interior or mucosal side of an anatomical segment. A peripheral compartment represents the blood side of the segment. The central and peripheral compartments are connected by a flow regulator representing a physiological barrier through which material from the central compartment "flows" or is transferred to the peripheral compartment at some empirically defined or calculated transfer rate "ka" applied by a converter, which allows calculation of parameters using compartment values. Transfers ("flows") between compartments can be zero order, second order and/or mixed order processes. As an example, a first order transfer from central compartment 1 to peripheral compartment 2 can be defined by a finite difference equation connecting inputs (e.g., rate constant k12 and amount of compound in stomach=amount+dt*(-elimination−k12+k21)) to the flow controller between the compartments (e.g., k12) and setting it as the product of the two variables. Thus the underlying equations of the model are utilized to calculate the amount of a compound in each compartment, and standard differential equations interrelate the system of compartments and their equations. This permits the model to simulate movement of a compound through each compartment according to the calculated rates at each time increment (dt). Since all movement between compartments is in units of mass, the blood side and transferred test compound concentration is calculated from the amount of compound in the blood side (peripheral compartment) and volume of the mucosal side (central compartment). A model cycle is entered through the input/output user interface as incremental pulses (to simulate ramp, plug flow/lag times) or as a fixed time range to initiate and effectuate cycling of a test compound of interest.

The basic structure of a physiological model and mathematical representation of its interrelated anatomical segments can be constructed using any number of techniques. The preferred techniques employ graphical-oriented compartment-flow model development computer programs such as STELLA®, KINETICA® and the like. Many such programs are available, and most employ graphical user interfaces for model building and manipulation. In essence, symbols used by the programs for elements of the model are arranged by the user to assemble a diagram of the system or process to be modeled. Each factor in the model may be programmed as a numerical constant, a linear or non-linear relationship between two parameters or as a logic statement. The model development program then generates the differential equations corresponding to the user constructed model. For example, STELLA® employs five basic graphic tools that are linked to create the basic structure of a model: (1) stocks; (2) flows; (3) converters; (4) input links; and (5) infinite stocks (See, e.g., Peterson et al., STELLA® II, Technical Documentation, High Performance Systems, Inc., (1993)). Stock are boxes that represent a reservoir or compartment. Flows or flow regulators control variables capable of altering the state of compartment variables, and can be both uni- and bi-directional in terms of flow regulation. Thus, the flow/flow regulators regulate movement into and out of compartments. Converters modify flow regulators or other converters. Converters function to hold or calculate parameter variable volumes that can be used as constants or variables which describe equations, inputs and/or outputs. Converters allow calculation of parameters using compartment values. Input links serve as the internal communication or connective "wiring" for the model. The input links direct action between compartments, flow regulators, and converters. In calculus parlance, flows represent time derivatives; stocks are the integrals (or accumulations) of flows over time; and converters contain the micro-logic of flows. The stocks are represented as finite difference equations having the following form: $Stock(t)=Stock(t-dt)+(Flow)*dt$. Rewriting this equation with timescripts and substituting t for dt: $Stock_t=Stock_{t-\Delta t}+\Delta t*(Flow)$. Re-arranging terms: $(Stock_t-Stock_{t-\Delta t})/\Delta t=Flow$, where "Flow" is the change in the variable "Stock" over the time interval "t." In the limit as t goes to zero, the difference equation becomes the differential equation: $d(Stock)/dt=Flow$. Expressing this in integral notation: $Stock=\int Flow\, dt$. For higher-order equations, the higher-order differentials are expressed as a series of first-order equations. Thus, computer programs such as STELLA® can be utilized to generate physiologic-based multi-compartment models as compartment-flow models using graphical tools and supplying the relevant differential equations of pharmacokinetics for the given physiologic system under investigation. An example of iconic tools and description, as well as graphically depicted compartment-flow models generated using STELLA® and their relation to a conventional pharmacokinetic IV model is illustrated in FIG. 6–9.

The model components may include variable descriptors. Variable descriptors for STELLA®, for example, include a broad assortment of mathematical, statistical, and built in logic functions such as boolean and time functions, as well as user-defined constants or graphical relationships. This includes control statements, e.g., AND, OR, IF . . . THEN . . . ELSE, delay and pulsing, that allow for development of a set of production rules that the program uses to control the model. Variable descriptors are inserted into the "converters" and connected using "input links." This makes it is possible to develop complex rule sets to control flow through the model. The amount of time required to complete one model cycle is accomplished by inputting a total run time and a time increment (dt). The STELLA® program then calculates the value of every parameter in the model at each successive time increment using Runge-Kutta or Euler's simulation techniques. The preferred simulation technique is Runge-Kutta. Once a model is built, it can be modified and further refined, or adapted or reconstructed by other methods, including manually, by compiling, or translated to other computer languages and the like depending on its intended end use.

Figure 10:
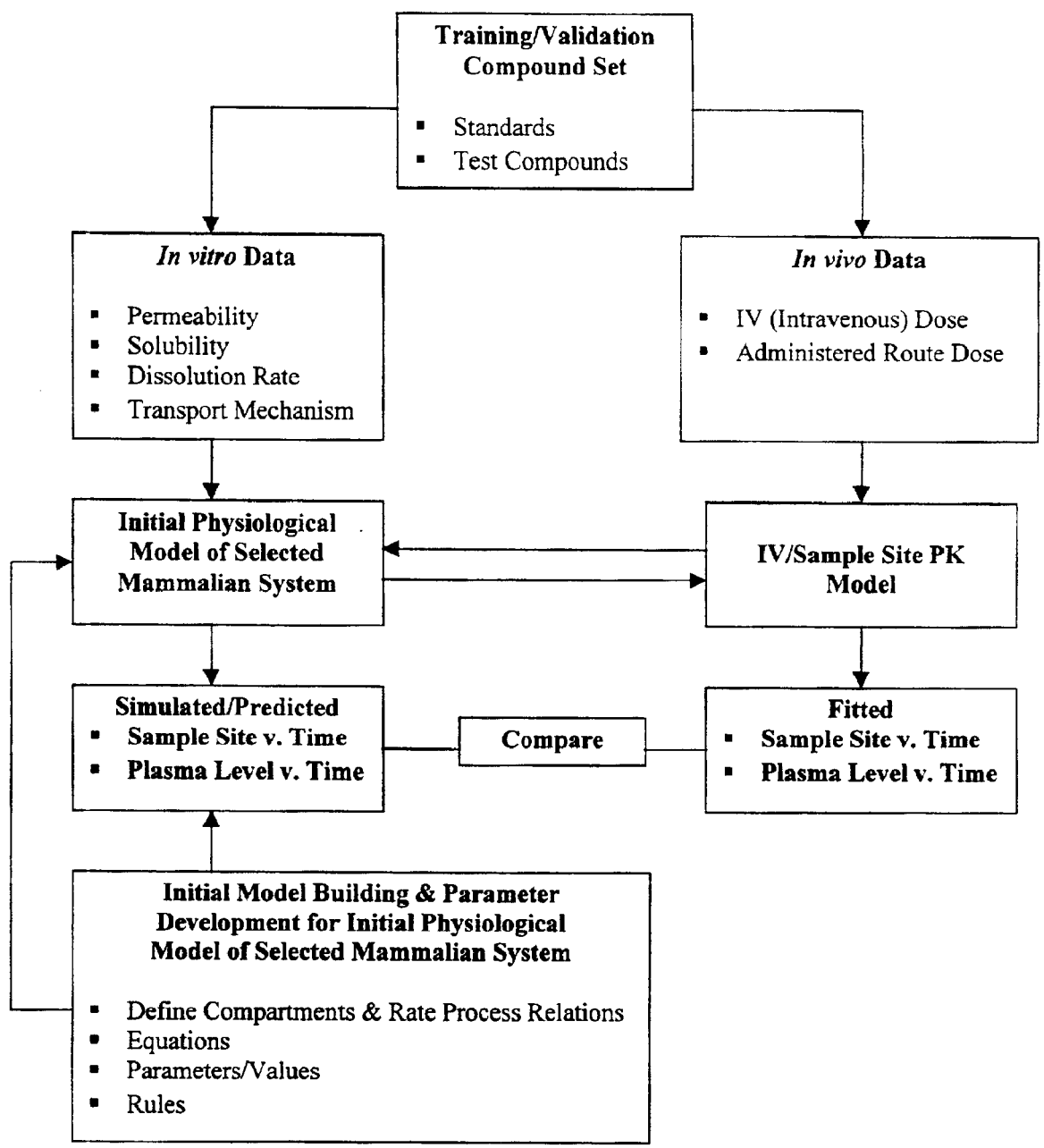
FIG. 10 shows schematic of a method of the invention for development of an initial physiologic-based simulation model for PK tool and method of the invention.

A preferred method of the invention for constructing a physiological model is depicted in FIG. 10. This method employs a two-pronged approach that utilizes a training set of standards and test compounds having a wide range of dosing requirements and a wide range of permeability, solubility, transport mechanisms and dissolution rates to refine the rate process relations and generate the initial values for the underlying equations of the model. The first prong employs the training/validation set of compounds to generate in vivo pharmacokinetic data (e.g., human plasma profiles). The second prong utilizes the training/validation set of compounds to generate in vitro permeability, solubility, transport mechanism and dissolution rate data that is employed to perform a simulation with the developmental physiological model. The in vivo pharmacokinetic data is then compared to the simulated in vivo data to determine how well a developmental model can predict the actual in vivo values from in vitro data. The developmental model is adjusted until it is capable of predicting in vivo absorption for the training set from in vitro data input. Then the model can then be validated using the same basic approach and to assess model performance.

In particular, three primary sets of data are generated from the training set for the comparison. The first set of data is empirically derived in vivo plasma data from animals or humans. The second set of data is obtained from conversion of the in vivo plasma data to a form corresponding to the primary sampling site of the developmental physiological model. The third set of data is empirically derived in vitro bioavailability data including permeability, solubility, dissolution rate and transport mechanism data. The raw data points are preferably collected and statistically analyzed to provide the best fit data. The best fit data may be obtained by any number of curve-fitting approaches, including standard regression techniques.

The in vivo plasma data is utilized to judge how well a developmental simulation model is able to predict absorption of the training set of compounds relative to the empirically derived in vivo plasma values. Plasma data also is utilized to calculate absorption at the relevant primary sampling site of the developmental physiological model. For instance, in order to use in vivo plasma data in a developmental physiological model, the plasma data must first be converted to data corresponding to the primary sampling site of the model. If plasma is the primary sampling site then no conversion is needed. However, if plasma is not the primary sampling site, then a pharmacokinetic training/validation model relating the primary sampling site and the in vivo plasma data is utilized. For example, when the developmental model is of the gastrointestinal tract, the portal vein can be selected as a primary sampling site and plasma selected as a secondary sampling site. Thus in this instance the in vivo plasma data is converted to portal vein data so that the parameters affecting secondary bioavailability events are separated from the primary absorption event resulting from passage of the test sample across the gastrointestinal lumen. This is accomplished by adding a plasma-portal vein conversion/validation model that relates in vivo plasma data to portal vein data. This plasma-portal vein conversion/validation model can be separate or integrated with the developmental model. In most cases, the plasma-portal vein model is based on a standard central-peripheral pharmacokinetic compartment approach for data conversion. The third set of data, the in vitro derived data, is utilized to run the developmental model, and the simulated absorption profile from this data set is compared to the in vivo derived plasma and simulated sampling site data. The developmental physiological model is modified until the simulated absorption profiles are in agreement with the in vivo denied plasma and simulated sampling site data.

As the number of parameters for evaluation increase it becomes more important to isolate and test each component of the model building process by validation using a standard validation set of compounds. The validation set of compounds should contain a diverse set of compounds that represent a broad range of absorption profiles for which both in vitro permeability, solubility, dissolution rate, and transport mechanism data, and in vivo plasma data is available. Statistical criteria such as sum of squares of the deviations between experimental data and calculated values obtained from the developmental physiological model are used to determine how well the model fits the data. If the developmental physiological model does not predict a good fit for the data, then the model is adjusted by isolating or including additional rate processes by an iterative approach.

Parameter values utilized in the underlying equations of a given physiological model may be provided in a database for ready access and manipulation by the PK tool of the invention. The database may include values for physiological parameters, such as rate constants and various other values employed in the PK tool. The rate constants correspond to time-dependent numerical constants describing rate processes (e.g., k12 and k21). The physiological parameters include rate constants, permeability, solubility, transport mechanism and dissolution rate variables, and the like, as well as pH, volume, surface area, transit times, transit rates, and the like, that are based on the physiology of a given anatomical segment represented in a selected physiological model.

Figure 11:
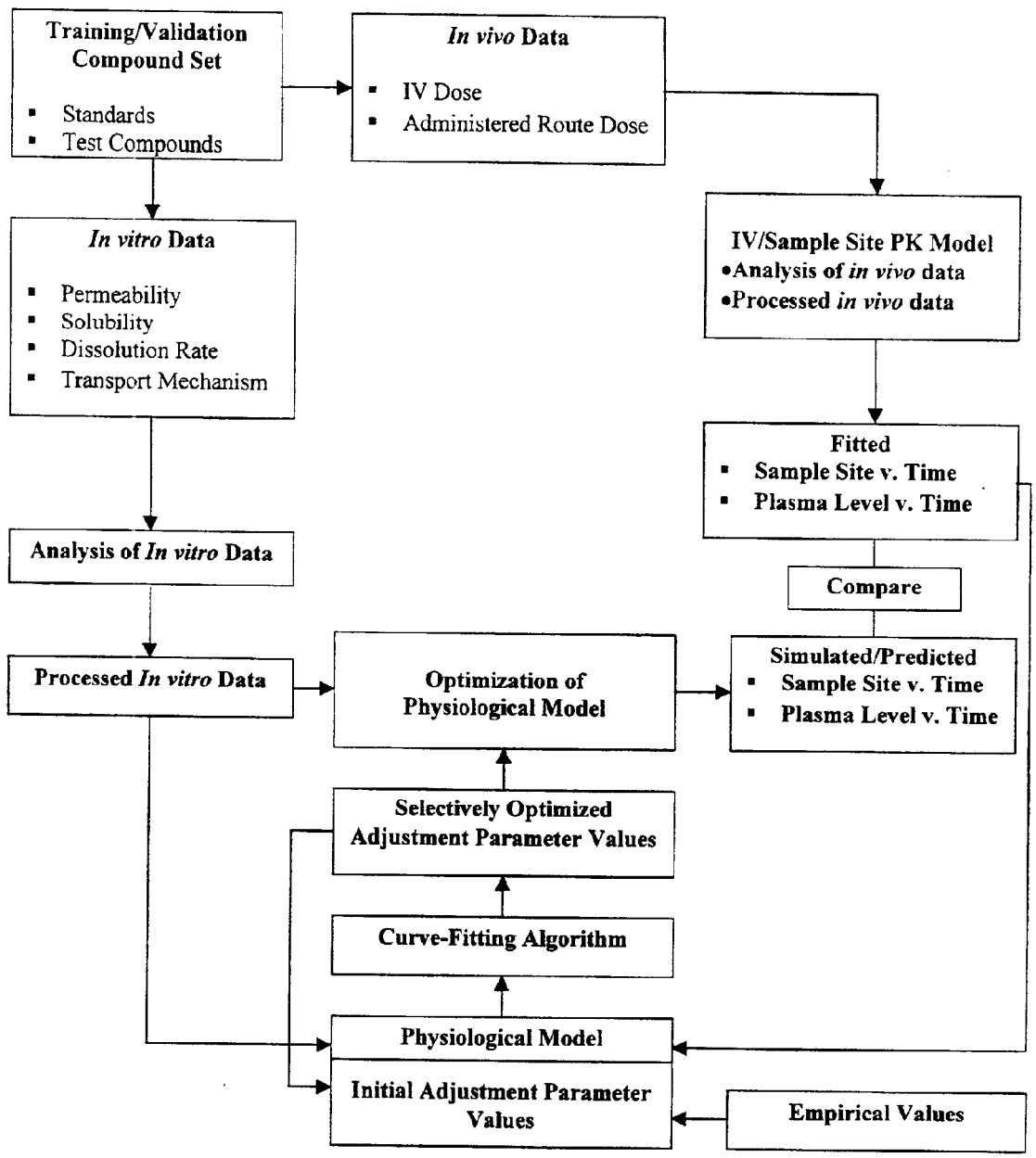
FIG. 11 shows schematic of a method of the invention for development of a physiologic-based simulation model having selectively optimized adjustment parameters.
Figure 27:
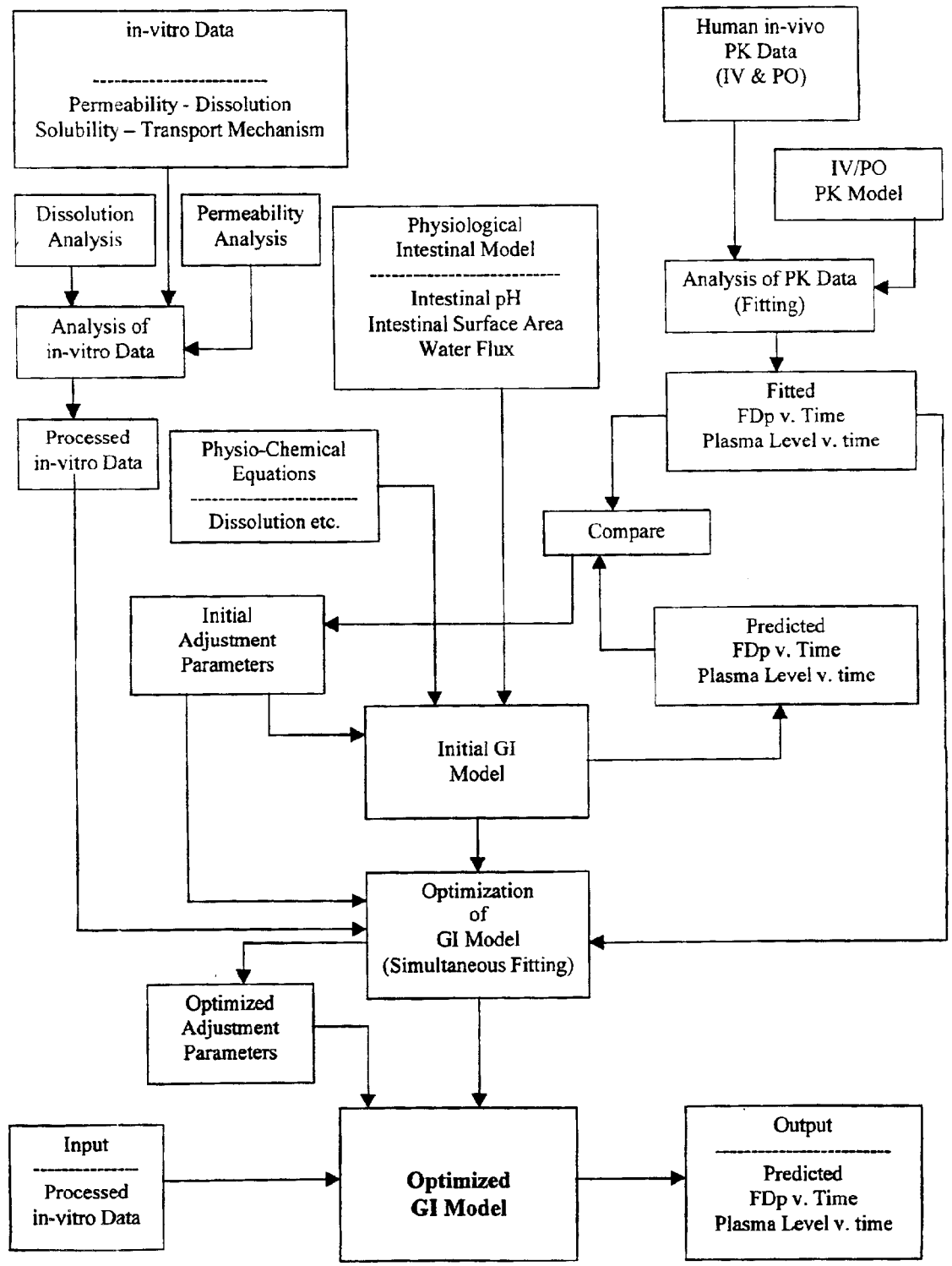
FIG. 27 shows schematic of method for development of selectively optimized adjustment parameters and for optimization of the integrated physiologic-based GI track simulation model of PK tool and method of the invention.
Figure 28:
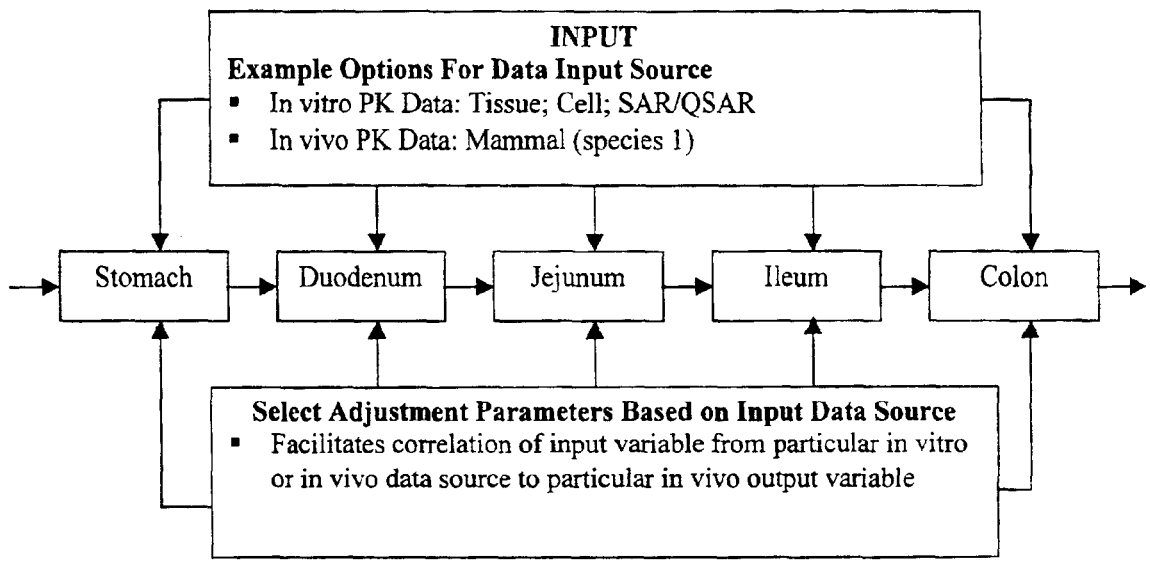
FIG. 28 shows schematic of method for selection of model parameters for utilization in a given physiologic-based GI track simulation model of PK tool and method of the invention.
Figure 29:
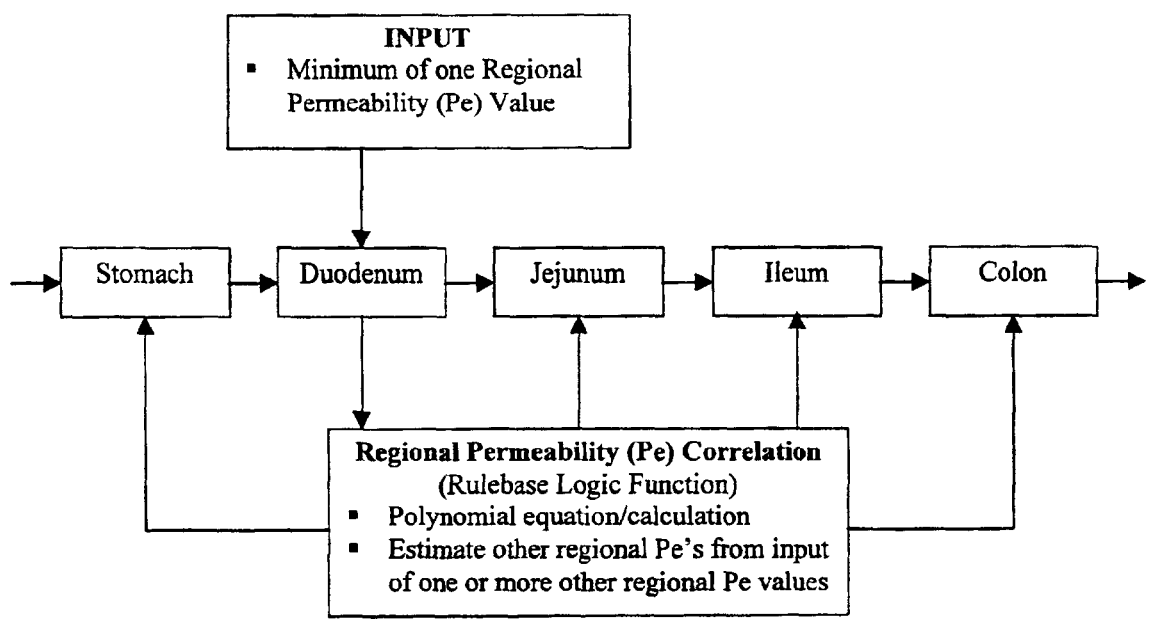
FIG. 29 shows schematic of method for regional (segmental) calculation/estimation of permeability from one or more user input values for permeability of a given GI tract region/segment. Regional permeability (Pe) correlation based on input of Pe value for duodenum is illustrated.
Figure 30:
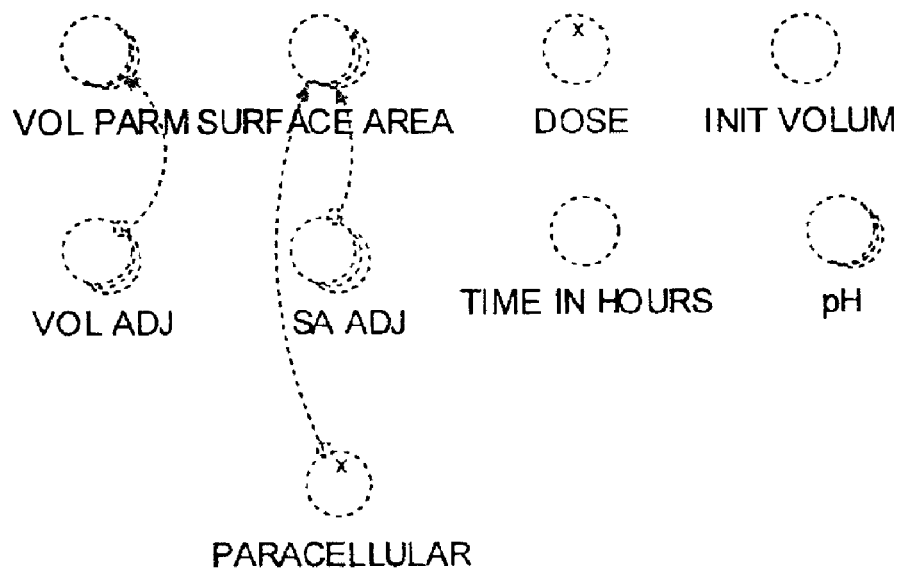
FIG. 30 shows graphical converter diagram illustrating volume, surface area, dose time and pH parameters and calculations for integrated GI track simulation model components of the PK tool and method of the invention.
Figure 31:
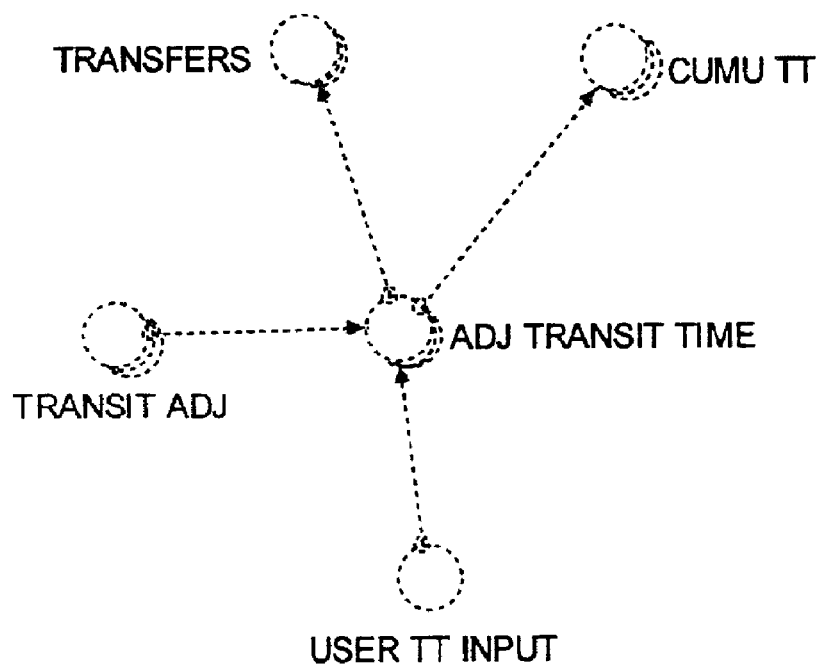
FIG. 31 shows graphical converter diagram illustrating GI tract transit time parameters and calculations for integrated GI track simulation model components of the PK tool and method of the invention.
Figure 32:
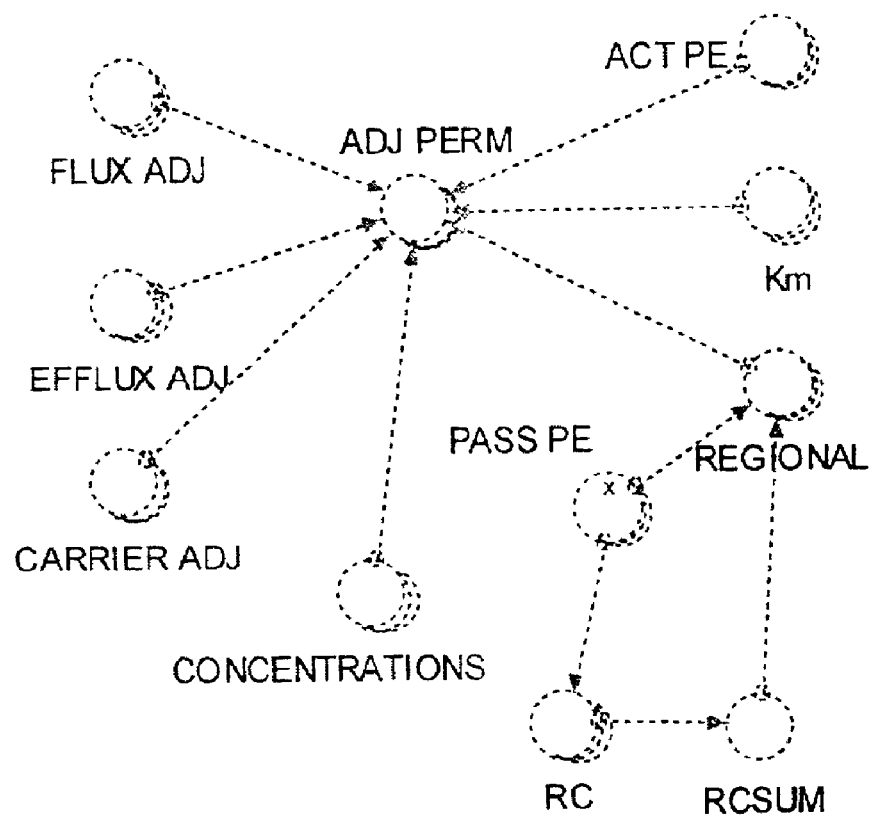
FIG. 32 shows graphical converter diagram illustrating GI tract permeability parameters and calculations for integrated GI track simulation model components of the PK tool and method of the invention.
Figure 33:
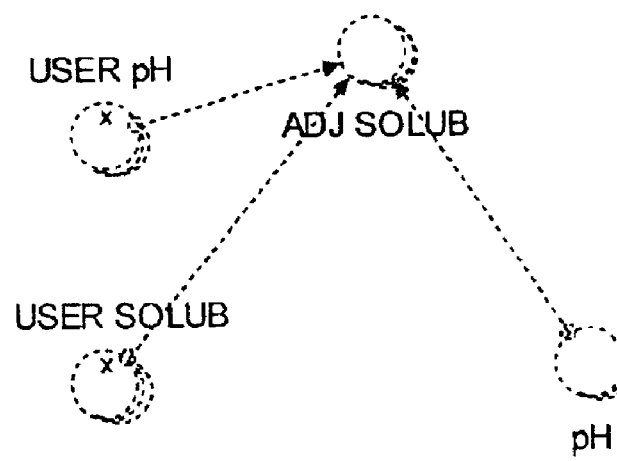
FIG. 33 shows graphical converter diagram illustrating GI tract solubility parameters and calculations for integrated GI track simulation model components of the PK tool and method of the invention.
Figure 34:
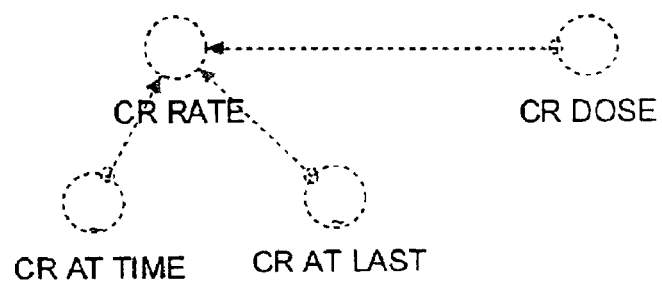
FIG. 34 shows graphical converter diagram illustrating GI tract control release formulation parameters and calculations for integrated GI track simulation model components of the PK tool and method of the invention.
Figure 35:
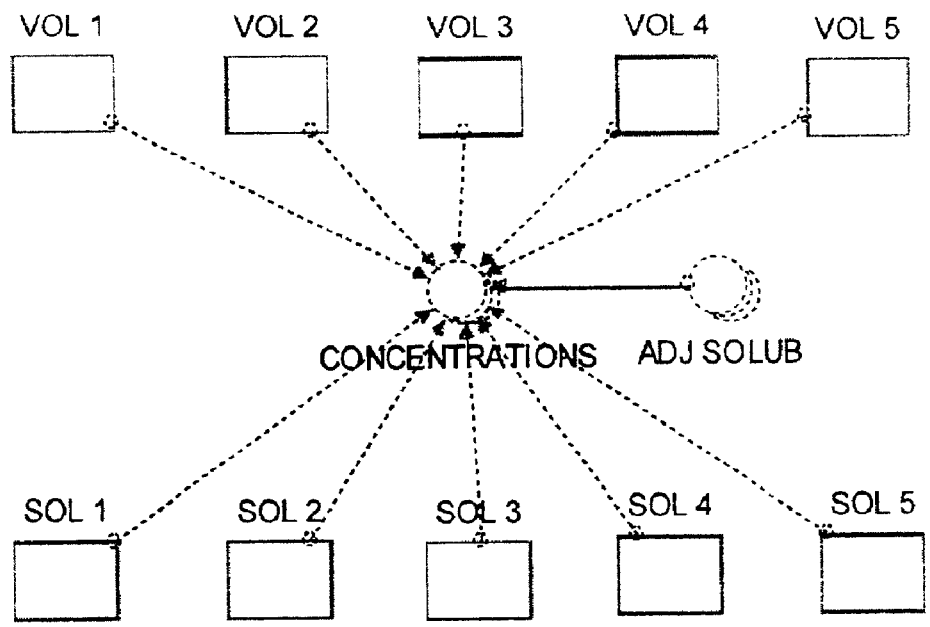
FIG. 35 shows graphical compartment-converter diagram illustrating GI tract concentration parameters and calculations for integrated GI track simulation model components of the PK tool and method of the invention.
Figure 36:
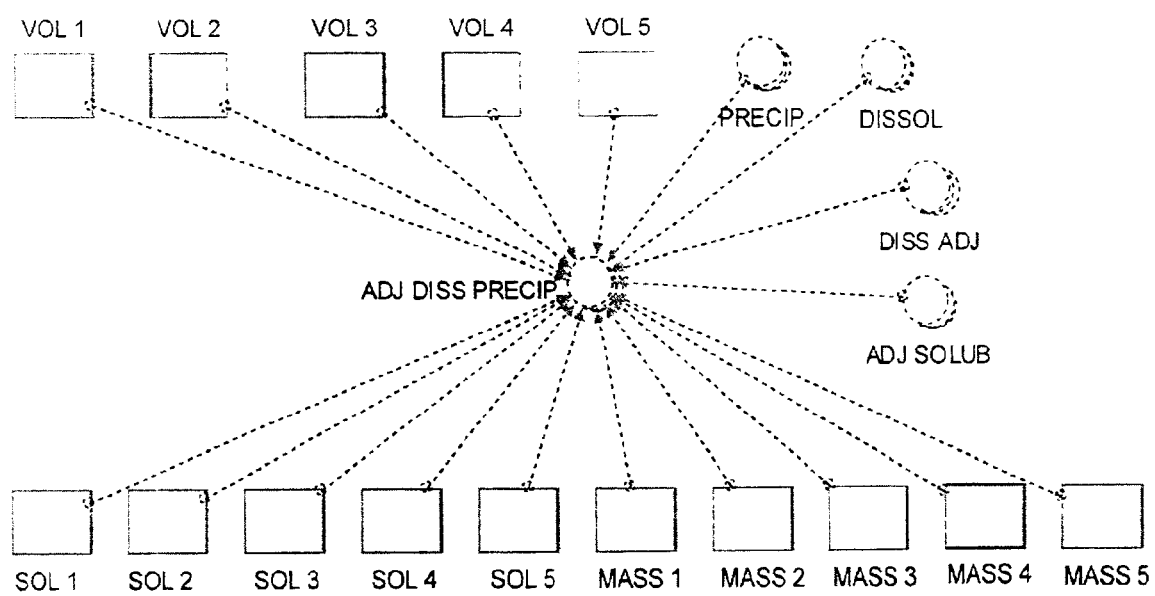
FIG. 36 shows graphical compartment-converter diagram illustrating GI tract dissolution parameters and calculations for integrated GI track simulation model components of the PK tool and method of the invention.
Figure 37:
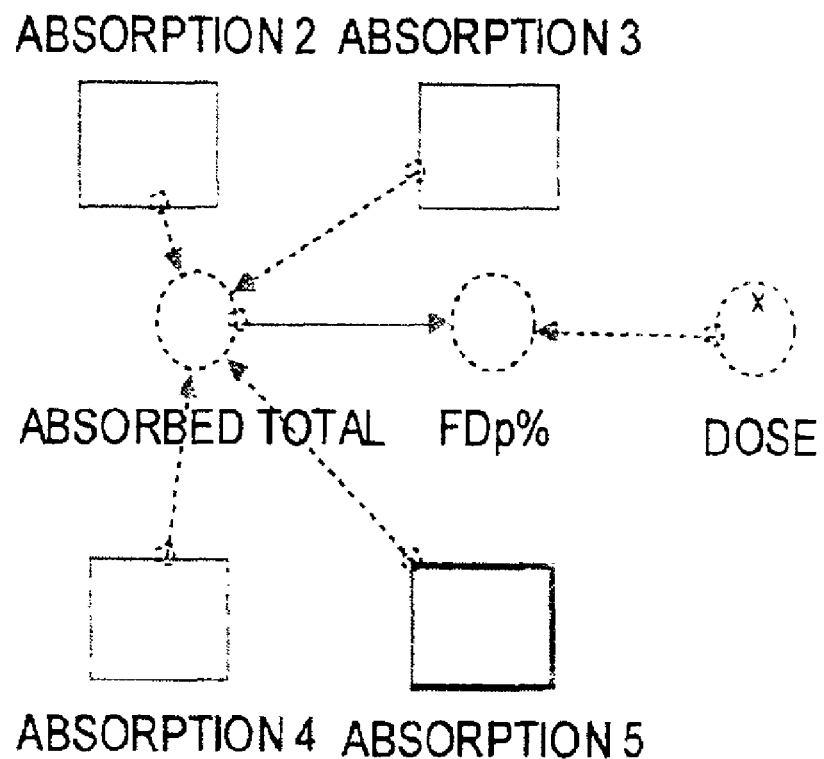
FIG. 37 shows graphical compartment-converter diagram illustrating GI tract output calculations for absorption for integrated GI track simulation model components of the PK tool and method of the invention.
Figure 38:
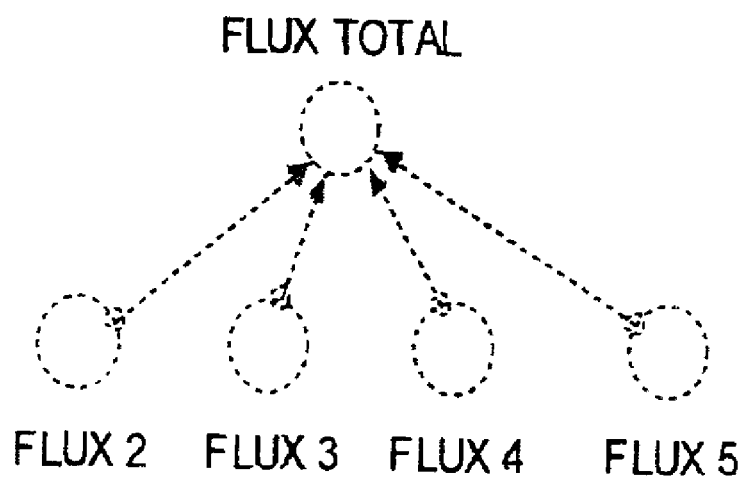
FIG. 38 shows graphical converter diagram illustrating GI tract output calculations for soluble mass absorption rate (flux) for integrated GI track simulation model components of the PK tool and method of the invention.
Figure 39:
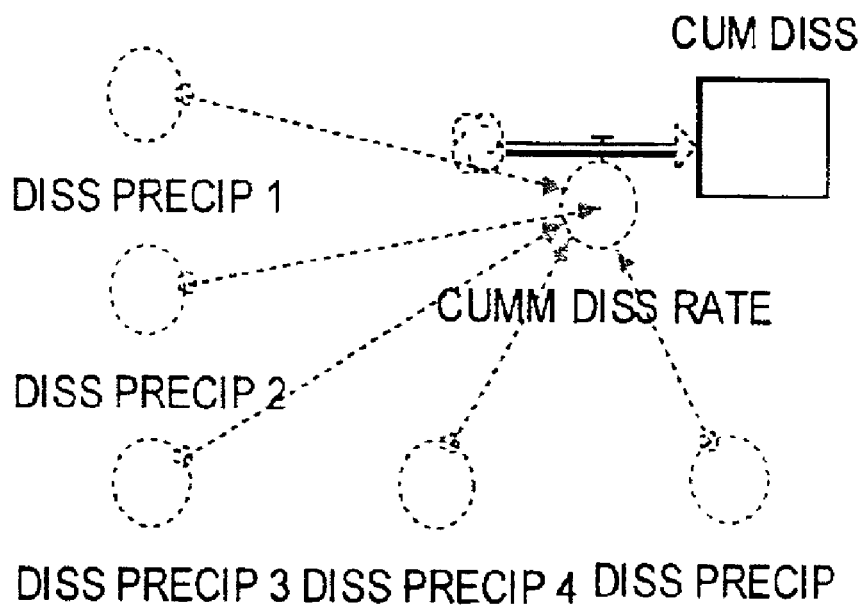
FIG. 39 shows graphical compartment-flow-converter diagram illustrating GI tract output calculations for cumulative dissolution rate and amount for integrated GI track simulation model components of the PK tool and method of the invention.
Figure 40:
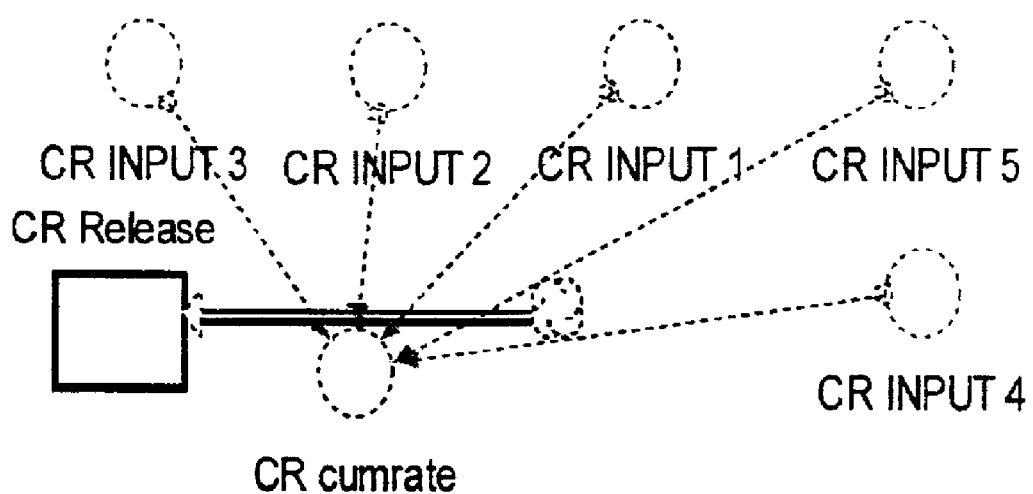
FIG. 40 shows graphical compartment-flow-converter diagram illustrating GI tract output calculations for cumulative control release formulation rate and amount for integrated GI track simulation model components of the PK tool and method of the invention.
Figure 45:
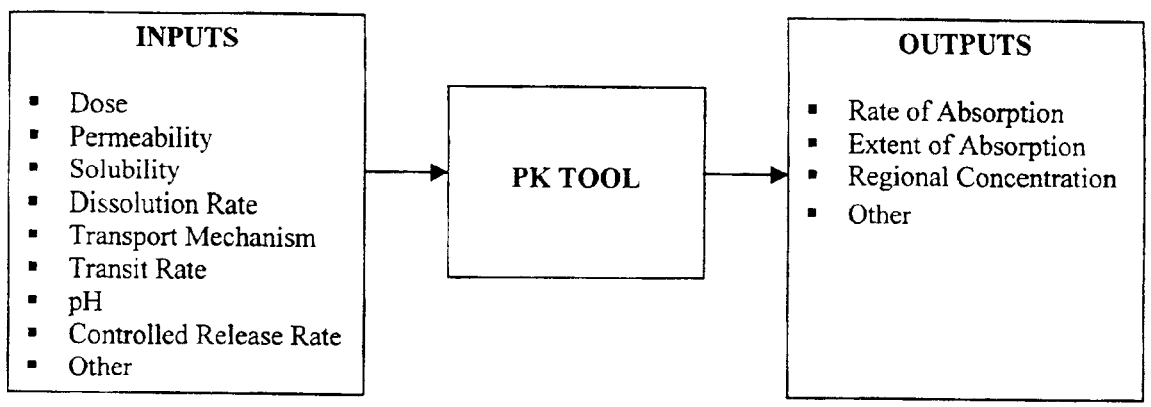
FIG. 45 is a high level INPUT/PROCESS/OUTPUT diagram of the PK tool of the invention as presented to a user of the carrying out a method of the invention, with inputs provided by the user and outputs provided by the PK tool.
Figure 46:
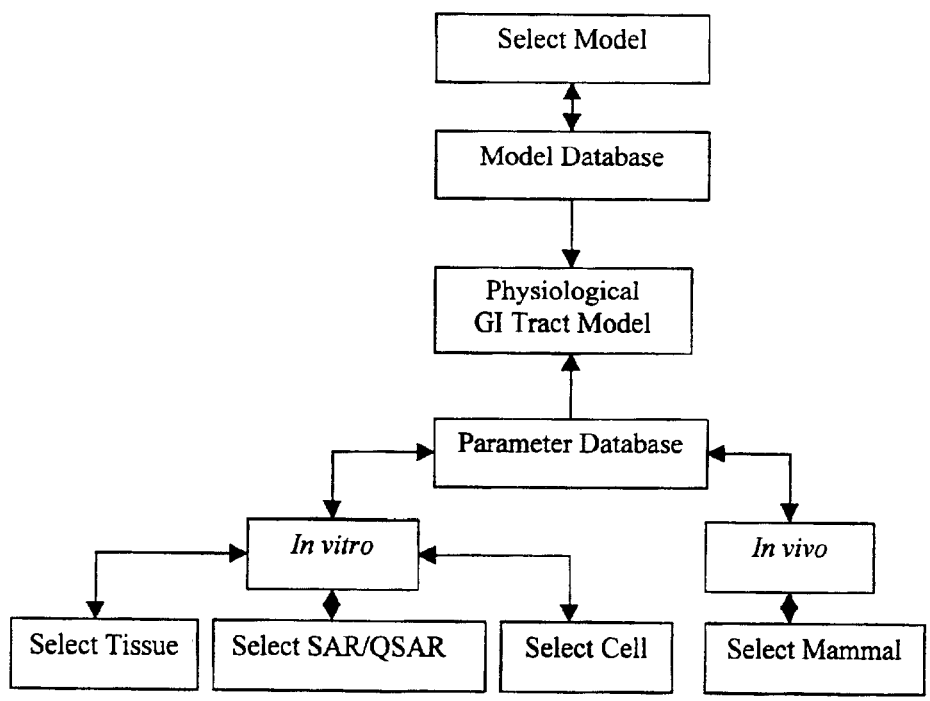
FIG. 46 illustrates a flow chart and structure chart of a subsystem of the PK tool and method of the invention for selection of a physiological GI track model from a model database and a parameter database.
Figure 47:
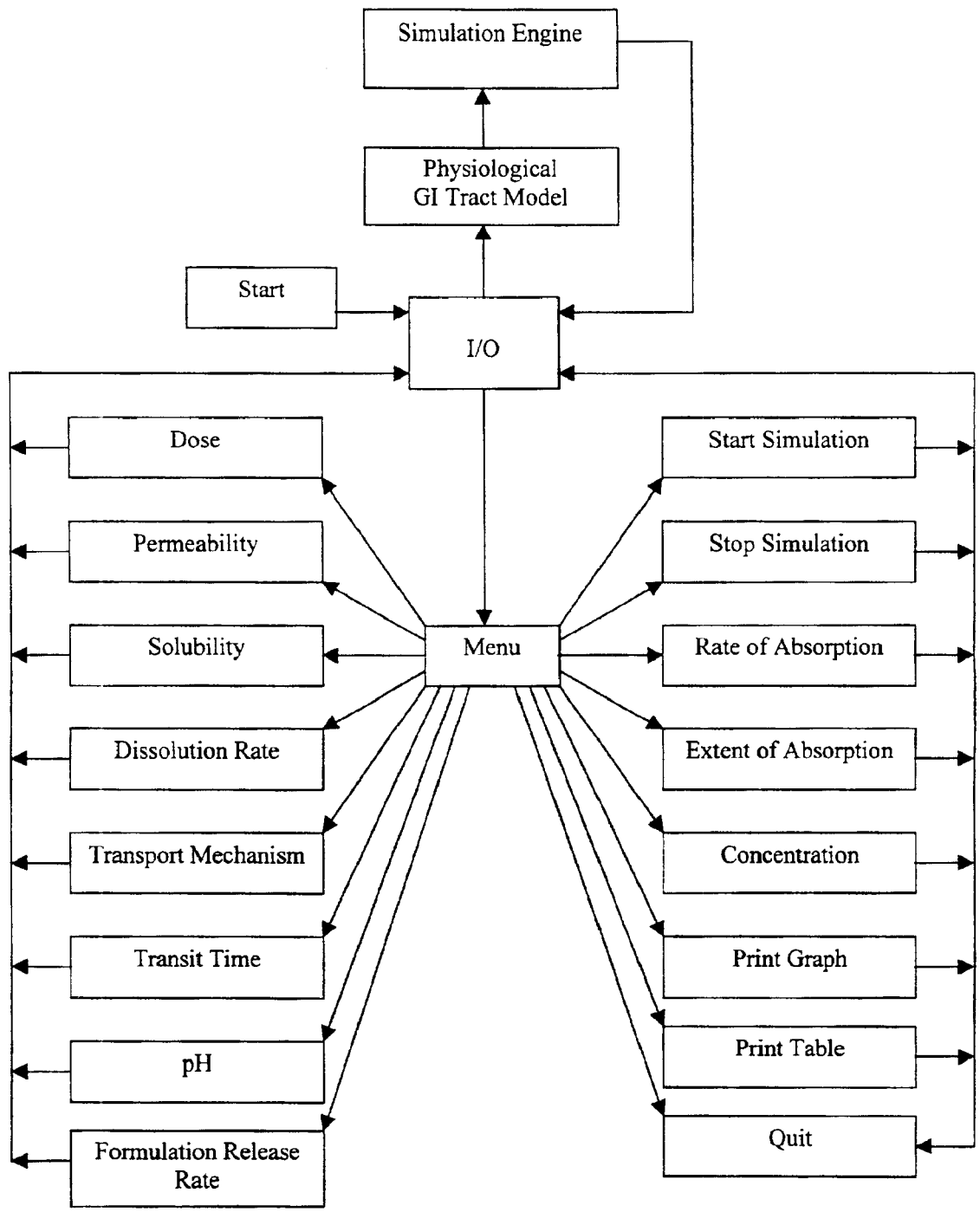
FIG. 47 is a flow chart and structure chart of the system of the PK tool and method of the invention.
Figure 48:
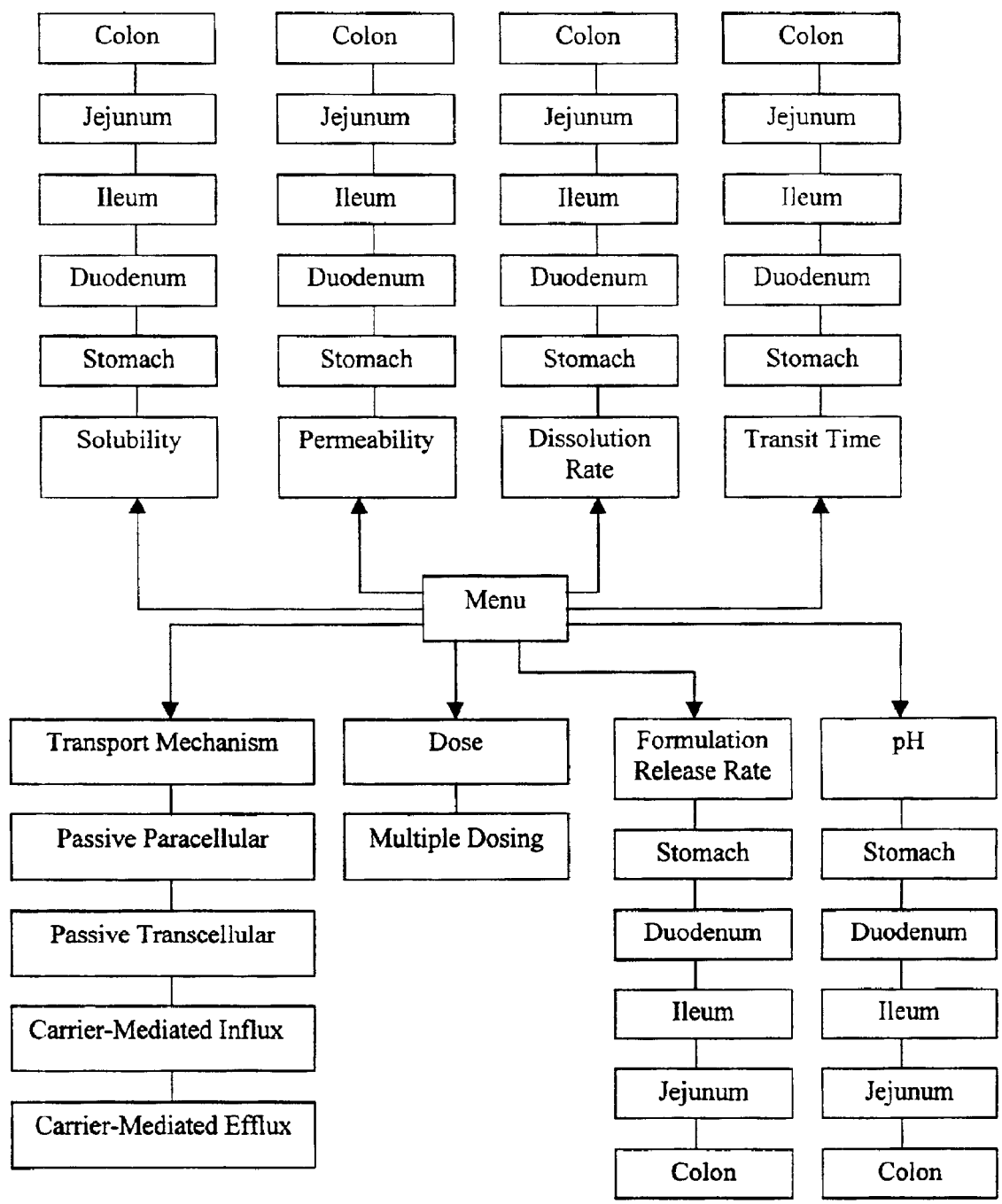
FIG. 48 is a flow chart and structure chart of a menu of the system of the PK tool and method of the invention.
Figure 49:
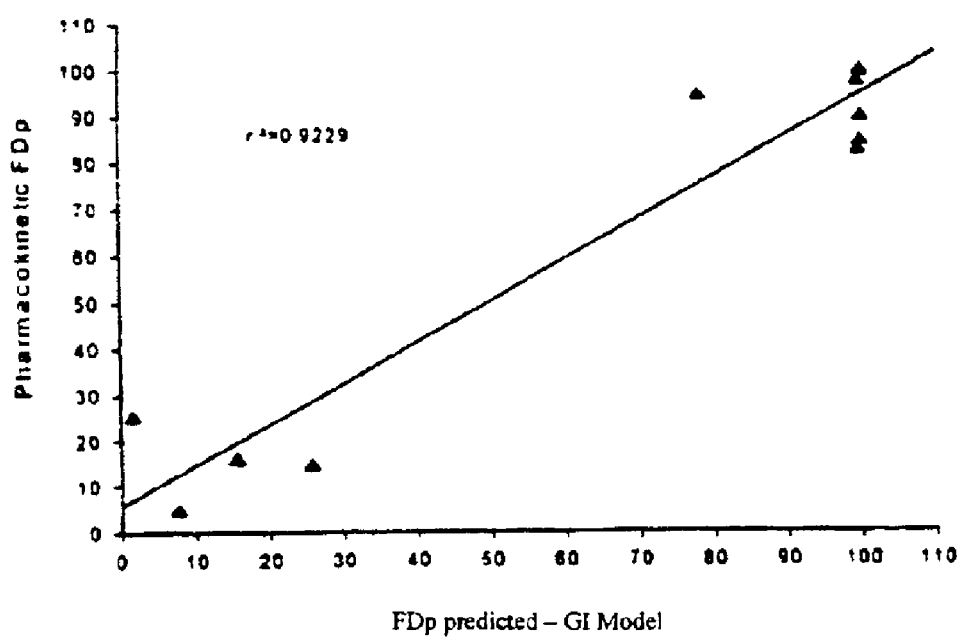
FIG. 49 illustrates correlation of extent of absorption for fraction of the dose absorbed in portal vein (FDp), as predicted using physiologic-based GI tract simulation model and PK tool of the invention, to FDp derived from human clinical data for 12 compounds.
Figure 50:
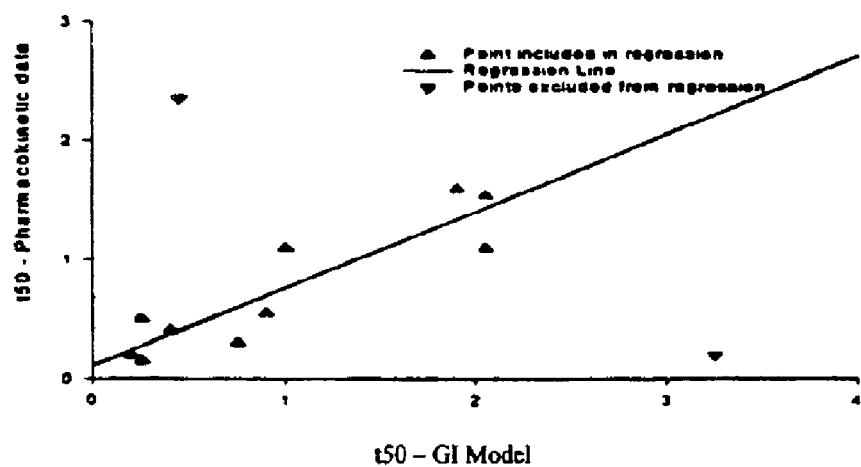
FIG. 50 illustrates correlation of rate of absorption for fraction of the dose absorbed in portal vein (FDp), as predicted using integrated physiologic-based GI tract simulation model and PK tool of the invention, to FDp derived from human clinical data for 12 compounds.
Figure 51:
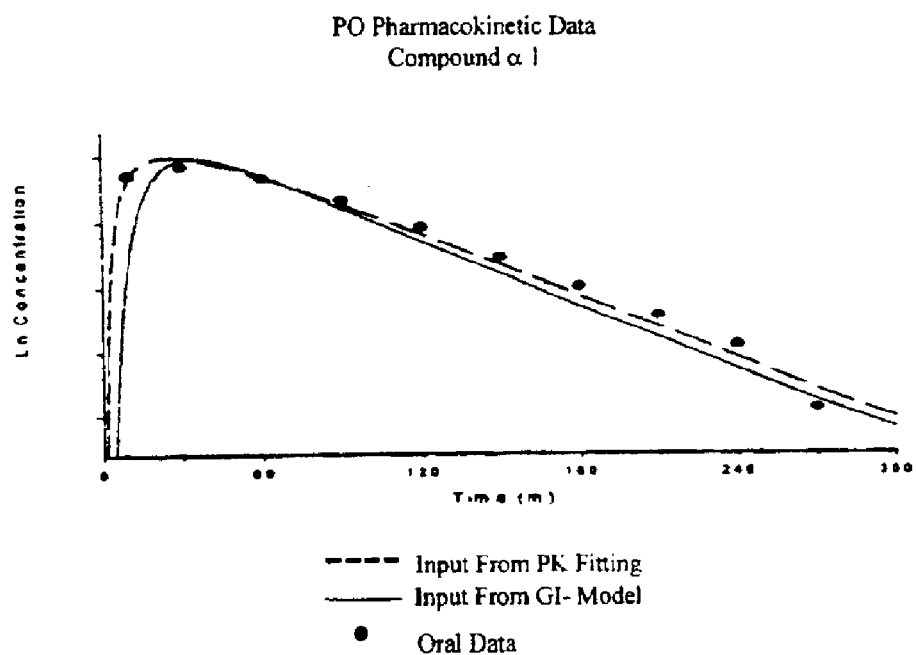
FIG. 51 compares plasma levels as predicted using integrated physiologic-based GI tract simulation model and PK tool of the invention, to plasma levels derived from human clinical data for a test compound.
Figure 52:
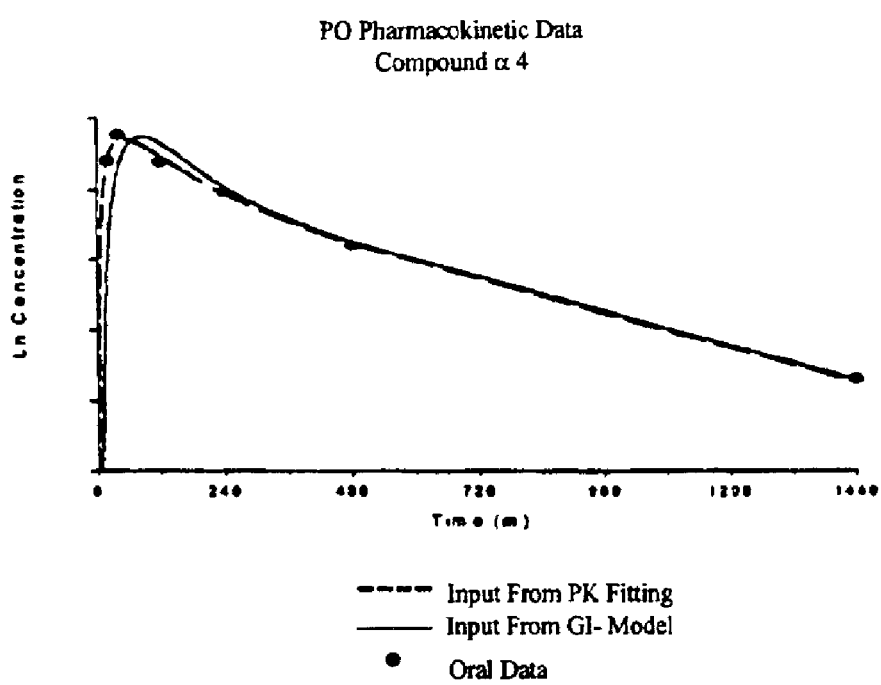
FIG. 52 compares plasma levels as predicted using integrated physiologic-based GI tract simulation model and PK tool of the invention, to plasma levels derived from human clinical data for a test compound.
Figure 53:
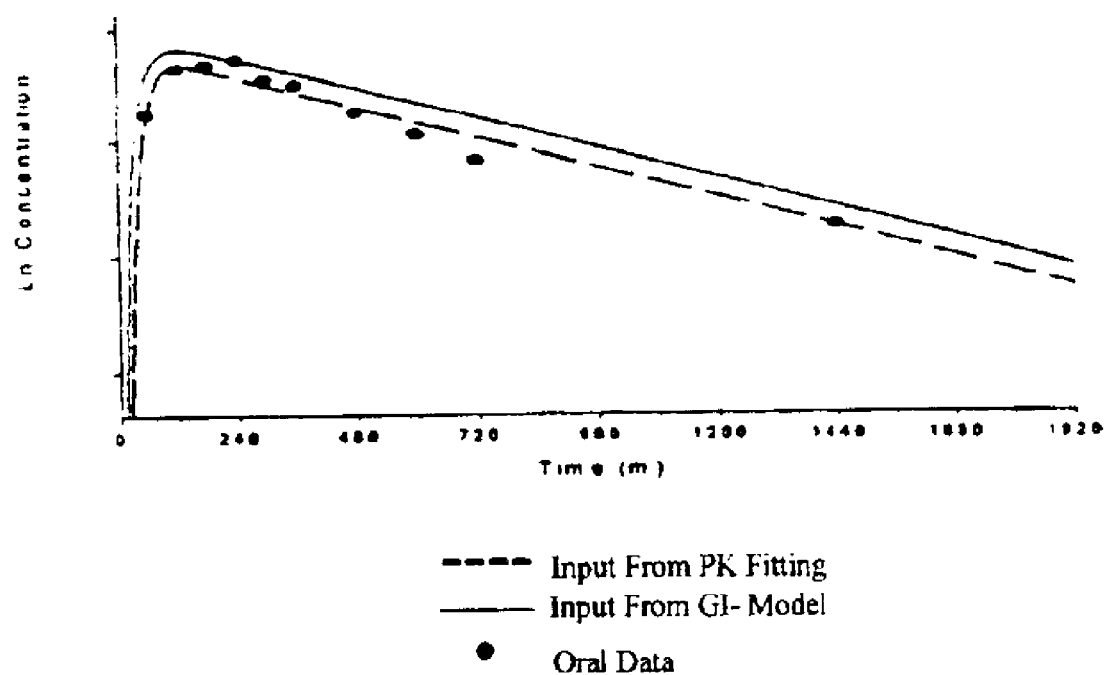
FIG. 53 compares plasma levels as predicted using integrated physiologic-based GI tract simulation model and PK tool of the invention, to plasma levels derived from human clinical data for a test compound.
Figure 54:
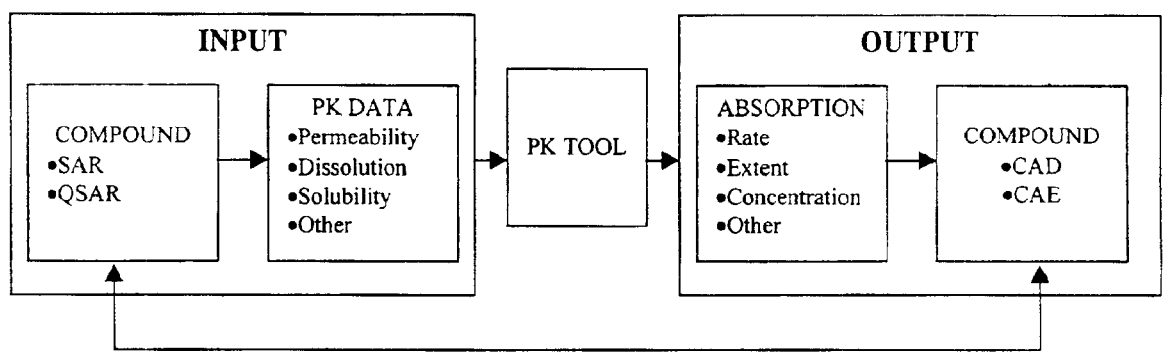
FIG. 54 shows high level INPUT/PROCESS/OUTPUT diagram of the PK tool of the invention for SAR/QSAR and CAD/CAE compound design and synthesis.
Figure 55:
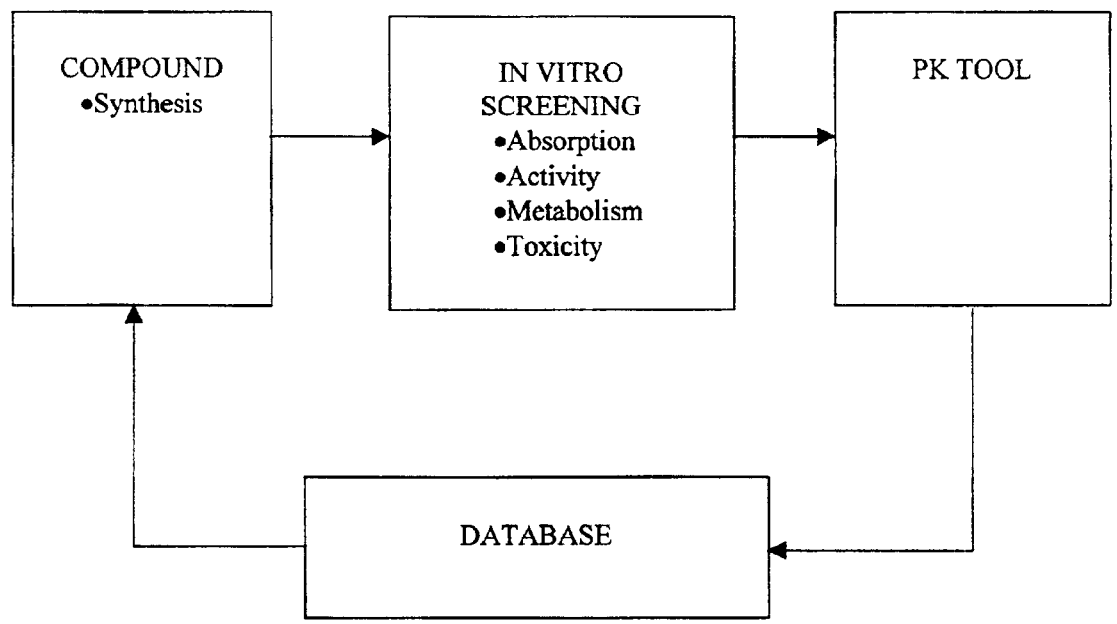
FIG. 55 shows high level flow and structure chart for screening method of the invention utilizing the PK tool and method of the invention.

The database also may include adjustment parameter values and/or regional correlation parameter values. The adjustment parameters include constants or ranges of constants that are utilized to correlate in vitro input parameter values derived from a particular in vitro assay system (e.g., rabbit intestinal tissue, Caco-2 cells) to a corresponding in vivo parameter value employed in the underlying equations of a selected physiological model (e.g., human GI tract). This aspect of the invention permits modification of existing physiologic-based pharmacokinetic models as well as development of new ones so as to enable their application for diverse compound data sets. The adjustment parameters are obtainable from iterative rounds of simulation and simultaneous "adjustment" of one or more empirically derived absorption parameters (e.g., physiological parameters for different anatomical segments) until the in vitro data from a given type of assay (e.g., Caco-2 cell data) can be used in the model to accurately predict in vivo absorption in the system of interest (e.g., human GI). In particular, the adjustment parameters are obtained by a stepwise selective optimization process that employs a regression-based curve-fitting algorithm that estimates the change required in a value assigned to an initial absorption parameter of a developmental physiological model in order to change an output variable corresponding to the simulated rate, extent and/or concentration of a test sample at a selected site of administration for a mammalian system of interest. Linear or non-linear regression may be employed for curve fitting, where non-linear regression is preferred. The regression analysis preferably utilizes a concurrent approach in which in vivo pharmacokinetic data (fitted in vivo sampling site data) and in vitro data are utilized simultaneously for the analysis. A few parameters of the developmental physiological model are adjusted at a time until the simulated absorption profiles generated by the physiological model for each of the training/validation compounds provides a good fit to empirically derived in vivo data. An example of this approach is depicted in FIGS. 11 and 27. Utilization of adjustment parameters permits predictability of diverse data sets, where predictability ranges from a regression coefficient ($r^2$) of greater than 0.40, 0.45, 0.50, 0.55, 0.60, 0.65, 0.60, 0.65, 0.70, or 0.75 for 80% of compounds in a compound test set having a diverse range of dose requirements and a diverse range of permeability, solubility and transport mechanisms. The preferred predictability ranges from a regression coefficient ($r^2$) of greater than 0.60, with a regression coefficient ($r^2$) of greater than 0.75 being more preferred, and greater than 0.80 being most preferred.

The regional correlation parameters of the PK tool include constants or ranges of constants that are utilized to estimate a selected parameter value of a first segment of the mammalian system under investigation when that value is not supplied by the user. The model performs this estimation by a polynomial approach, in which (1) regional correlation parameter values, and (2) one or more values for the parameter that is supplied by the user for a second segment of the mammalian system, are utilized to estimate the value for the first segment. The regional correlation parameters may be empirically derived values or adjustment parameter values for various segments of the mammalian system of interest such as for permeability. The polynomial is based on the particular parameter to be estimated. The regional correlation is performed by logic function of the model, which when activated utilizes a polynomial algorithm to perform the estimation. The regional correlation logic function of the model is activated when a value is missing for the selected parameter. The estimated value(s) are then utilized as input variables for the particular parameter in question. The model then proceeds by employing the estimated value for subsequent simulation. Various regional correlation parameters can be used, such as permeability, solubility, dissolution rate, transport mechanism and the like. The preferred correlation parameters are for permeability. This permits the PK tool of the invention to predict absorption of a test sample from minimal input permeability values, such as when the simulation model is a GI tract simulation model and when cell-based assays are employed to provide permeability data corresponding to a given GI segment (e.g., Caco-2 cells and colon).

Since the parameter values are specific for a given physiological model (e.g., GI model-parameters, Ocular model-parameters, Blood-Brain-Barrier-parameters, etc.), parameter values are chosen accordingly. These values are obtainable de novo from experiments or from the literature. The preferred values are based on a diverse collection of training/validation compounds for which in vivo pharmacokinetic data is available.

The various physiological models also may reside in a database, in part or in whole, and may be provided in the database with or without the initial parameter values. The database will preferably provide the differential equations of the model in a compartment-flow data structure that is readily portable as well as executable by the simulation engine.

An integrated physiological model corresponding to the GI tract of a mammal constructed using STELLA® and the above-described methodology is illustrated in FIGS. 25–26 and 30–40. An example of information provided by the database is illustrated in Appendix 4 for the gastrointestinal model depicted in FIGS. 25–26 and 30–40.

A physiologic-based simulation model of the PK tool and method of the invention may optionally include a training/validation model. This aspect of the invention can be used for determining whether the model is specific and accurate with respect to compounds of known membrane transport mechanism (e.g., passive transcellular, passive paracellular, transporter involved for absorption and secretion) and/or with respect to known drug solubility/dissolution rate limitations.

Figure 12:
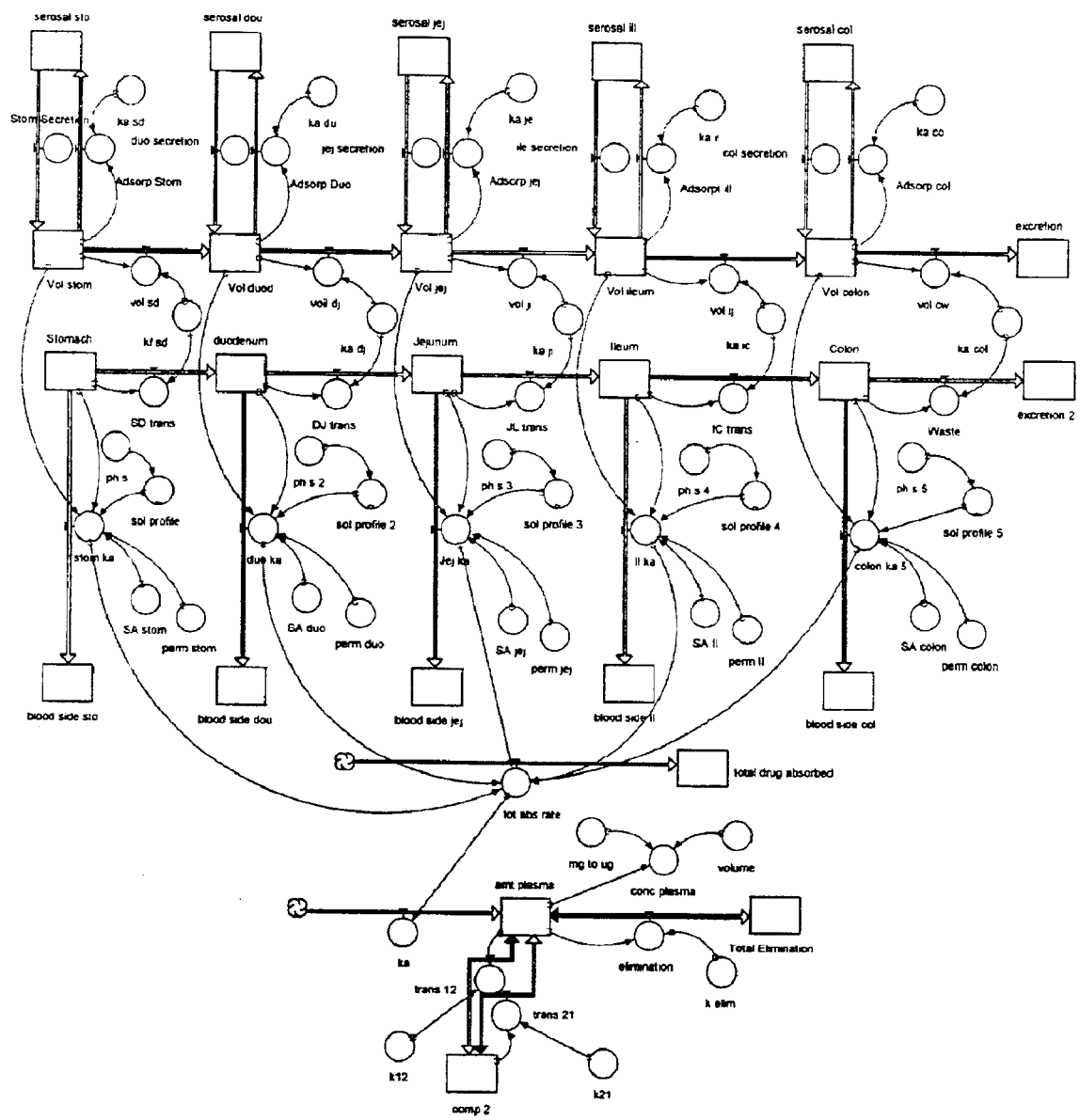
FIG. 12 shows graphical compartment-flow diagram illustrating the mass-volume GI tract simulation model of the invention linked to a training/validation plasma model.

A validation model can be linked to the physiological model of the invention as illustrated in FIG. 12. The linked system is then run to access the specificity and accuracy computed values for rate and extent of absorption. These values are then compared to empirically measured plasma values. If computed values fall outside of an acceptable range the model can be reevaluated for these compounds and adjustments made to the model.

Absorption Profile Ranking/Cataloging:

Absorption profiles generated for test samples of a compound library are compared to select those samples having a desired absorption profile. The selection process essentially involves ranking the compounds by one or more absorption parameters such as rate, extent and/or concentration, or parameters derived therefrom. By "ranking" is intended assignment of a feature to a compound or pool of compounds that distinguishes it from another in a hierarchical manner.

The manner in which ranking is recorded is not a limitation of the invention. For example, ranking may be any recorded by any descriptor that represents the desired absorption parameter, provided the descriptor is ultimately interpretable by a machine and/or a human. Bar codes, numbers, letters, symbols, scalars and the like are examples. A ranking value may be encrypted and later decoded if desired. In some instances, the ranking information can be stored in one form or unit of an absorption parameter, and keys utilized to convert the ranking unit to the next, such as for converting in vitro data to a value that has meaning in the context of in vivo data. In other instances the bioavailability data may be recorded in otherwise abstract pieces, that when combined or processed by a converter, such as a mathematical algorithm, yields a value in a new context. Ranking information is preferably stored in a database, i.e., location(s) where data can be permanently and/or temporarily stored, accessed and/or updated etc.

Quality of the data, whether derived from the literature or other sources, is an important consideration in reliability of the ranking. For example, data in an evaluation test set can be assigned or scored with a quality grade, such as A, B, C etc., based on data source and quality. Data also may be converted into scalar units for ranking purposes. The scalar units can be qualitative and/or quantitative. They also may be assigned to various ranges, where values falling within a particular scalar range indicate an extent, presence and/or absence of a particular bioavailability property. For instance, a scalar value in the range of 1–10 may be used, where values 1–3 indicate poor bioavailability, 4–6 indicate marginal bioavailability, and 7–10 indicate increasing bioavailability. The scalar can be specific or general. An example of a specific scalar unit system of ranking is "Scalar Unit= Specific PK parameter." General scaling is exemplified by qualitative endpoints (i.e., endpoints simply reported as positive (absorption) or negative (no absorption)). Statistical methods can be used in the ranking process if desired.

Generally the selected compounds also are catalogued using a descriptor, which reflects the absorption and/or ranking profile. By "cataloging" is intended assignment of a descriptor for indexing, filing and/or retrieval from a database. Cataloging permits the information to be provided to a compound archive of the originating library, as well as separate libraries that contain the selected compounds. This includes cataloging and organizing compounds of the library according to a selected absorption profile or specific absorption parameter and cross-referencing by features other than absorption. These features include, but are not limited to, for example, distribution, metabolism, elimination, toxicity and biological activity. Other features include transport mechanism (e.g., passive diffusion, active transport etc.), molecular size (e.g., molecular weight), polarity, charge (e.g., pKa), method of preparation (e.g., synthesis, biosynthesis, extraction, etc.), structure (e.g., mass spectrophotometry, X-ray crystallography, NMR, etc.), and/or applications (e.g., pharmacologic class, functional materials, additives, catalysts, etc.). Alternatively, the absorption profile/parameter information can be added to existing data files that characterize a test sample of a parent library or portion thereof.

Cataloging is extremely valuable in terms of library management and data analyses of libraries. For instance, cataloging facilitates grouping and organization of compounds in high-throughput screening compatible, multi-well units containing single or pools of compounds per storage vessel. Data maps outlining the position of each compound or pool of compounds and its corresponding absorption catalog descriptor also may accompany storage units. The data maps are represented in a machine-readable format that can be provided to a database.

High-Throughput Screening:

The method of the invention is particularly suited for high-throughput screening of compound libraries. High-throughput screening provides a very rapid approach for carrying out a large number of experiments in a short period of time through the combination of automation and biochemical testing. An additional aspect of high-throughput screening is the use of small volumes for the assays, thus decreasing the amount of a to-be-screened compound necessary and facilitating automation. High-throughput screening utilizing the PK tool of the invention similarly provides a very rapid approach for carrying out a large number of bioavailability predictions in a short period of time. SAR and QSAR information also may be utilized for high-throughput screening.

A high-throughput screening method can be based on an in vitro assay for collecting permeability, solubility, dissolution and transport mechanism data. The assays can be based on detection by a variety of known methods including spectrophotometric or optical tracting of radioactive or fluorescent markers, conductivity, light absorbency, or other method of tracting a molecule based on size, charge, affinity and the like. Any assay method that is robust, simple and amenable to automation can be used as the basis of a high-throughput screening method. For example, an high-throughput screening method can measure gain or loss of radioactivity, gain or loss of fluorescence, a change in the resistance or conductivity of a membrane (WO 96/13721), cell monolayers (WO 97/16717), or a cell suspension (WO 97/49987). High-throughput solid and/or liquid handling devices may be employed for solubility and dissolution screens. An advantage of high-throughput screening is the ability to assay a large collection of compounds in an extremely short period of time.

The method of the invention can be integrated with combinatorial chemistry, engineering and instrumentation to create novel assay formats. Lead optimization may employ traditional single-compound synthesis or parallel synthesis of discrete compounds. One approach for parallel synthesis and screening is array chemistry, a system involving dozens of parallel reactions for establishing structure/bioavailability relationships. Synthesis reactors and purification equipment can be automated and integrated with the PK tool and method of the invention. This affords faster screening of larger numbers of compounds.

In particular, compounds may be screened individually or as sets or arrays of sets. For instance, a compound set may contain unique backbone chemistry with diverse side groups attached. These arrays are created by combinatorial reaction of a serial number of functionally identical but structurally diverse building blocks to create a single compound, which is chemically analyzed by HPLC and mass spectrometry. The compounds are then logically arranged in spatially addressable multi-well microtiter plates (e.g., 96 and/or 386 well microtiter plates) with a single compound per well. This format yields multiplex array where other properties such as chemical structure, mass and the like are stored in a database that is searchable via a unique catalog descriptor. These arrays may be assembled into a larger set of compounds referred to as an array of sets.

Several strategies can be employed to manage the high-throughput absorption screening of large chemical compound sets against multiple cell types, tissues, and physiological conditions. The single compound per assay per well is the most direct. The advantages are that no deconvolution is required and minimal potential for masking exists. Single compound per assay fits particularly well with the multiplex screening array, where a primary assay provides extensive absorption and structure-bioavailability data, the negative assay data also adding value for subsequent lead optimization.

Alternatively, pooling of compounds per assay well can be employed to quickly and efficiently assay large compound sets. The primary disadvantage is the need for subsequent deconvolution of positive readouts, the potential for masking of one compound's absorption profile by others, and thus information content of the compound set is partially lost. Nevertheless, the pooling approach is very useful for rapid high-throughput screening of larger libraries, where the compounds are screened in blocks containing discrete pools or mixtures of compounds per test sample, where about 1,000 to 100,000 compounds are represented per block, and about 3 to 10 compounds per discrete pool. Permeability and solubility data are generated using a robotic high-throughput system. For example, compounds can be stored in carousels with robotic retrieval systems and conveyors delivering samples to a dispensing area. Individual samples are identifiable by bar codes. The system can be configured to hold a variety of libraries in different phases ranging from solid archives to liquid libraries in micro-tubes or micro-plates and, being modular in design, can be readily adapted according to the differing needs of a user and or piece of testing equipment. If desired, dissolution rate and transport mechanisms are preferably screened in subsequent rounds of deconvolution.

Permeability and solubility studies on mixtures of compounds yield hybrid or conglomerate values unless the compounds are provided in stoichiometric concentrations and quantitatively tracted through the testing process, for instance via LC/MS, so as to minimize masking effects. Conglomerate values can be separated further by collecting the relevant data for each pool under different gradient testing conditions, such as concentration, pH, and physiological fluid/solvent system gradient conditions. This approach generates permeability and solubility profiles representing ranges of values that are readily supplied as input into the PK tool of the invention.

Discrete compound pools selected by a hybrid absorption profile for a given route of administration can then be deconvoluted by any technique known in the art. Smaller pools or individual compounds separated from a test pool can be subjected to further subsequent rounds of more focused absorption screening according to the methods of the invention.

If desired, multiple parallel high-throughput bioavailability screens in addition to absorption can be utilized to screen large compound arrays so as to maximize structure/bioavailability information content and turnaround time. The compound libraries screened for bioavailability can be integrated into data management programs, and multiplexing in primary and secondary assays.

As can be appreciated, the method of the invention does not require knowledge of biological activity to create libraries optimized for bioavailability. However, activity hits in these libraries are likely to exhibit improved administration route-specific bioavailability in vivo and thus improved in vivo pharmacological activity compared to those selected by activity alone. Accordingly, the method of the invention provides a receptor-independent approach to cataloging and designing compound libraries with optimally diverse properties, as well as selection and design of compounds for lead drug development and optimization. The method is readily adapted for automated high-throughput screening and ranking of unscreened libraries (pristine), previously screened libraries (screened), focused libraries pared down by screening and selection (focused), or combinations thereof. Libraries produced by the methods of the invention increase the chance of identifying lead compounds having improved pharmacological activity in vivo for a selected route of administration before or early in drug development.

The following examples illustrate various aspects of this invention. These examples do not limit the scope of this invention.

EXAMPLES

A physiologic-based simulation model for predicting oral absorption of a compound in a mammal from in vitro (e.g., tissue, cell and SAR/QSAR) and in vivo data (e.g., human) was constructed in two primary stages. The first stage involved development of a mass-based multi-compartment simulation model (mass model), a volume-based multi-compartment simulation model (volume model) and an integrated mass-volume multi-compartment simulation model (mass-volume model). These models were individually tested and validated for five segments of the GI tract: the stomach, the duodenum, the jejunum, the ileum, and the colon. The second stage involved development of an integrated multi-compartment physiological model of the GI tract (GI model). The models were developed using a combination of in vitro data and in vivo data.

A computer-based mathematical model development tool with a graphical user interface was employed to design and construct the initial simulation models. The computer program STELLA® was selected as suitable for this purpose since it permitted compartment model building and mathematical equation modification and at each stage of the build, as well as calculation of flow between compartments at user-specified time intervals (dt) with user-specified input functions and values. An example of iconic tools and description, as well as graphically depicted compartment-flow models generated using STELLA® and their relation to a conventional pharmacokinetic IV model is illustrated in FIGS. 6–9.

Example 2

Compound Data Sets

Compound data sets for development, and thus building, testing, training and validation of the models were obtained from various sources including the literature and cell, tissue, animal and human tests as described herein. The data sets included relevant physiological parameters related to absorption of a compound including GI track related parameters (e.g., pH, initial volumes, surface area, average transit time, volume transfer rates, new water absorption etc.) and physicochemical compound related parameters (e.g., dissolution, permeability, solubility etc.).

Data sets were selected for compounds that permitted development and isolated testing and validation for each stage of the build. Compounds suitable for this purpose were chosen as follows. For the mass, volume and integrated mass-volume simulation models, a candidate compound was chosen based on the premise that the best candidate compound for model development would not be a drug that is highly correlated pharmacokinetically between cell, tissue, animal and humans, but one that is poorly correlated. That is, a compound predicted to have high total absorption in humans based on pre-clinical studies, but ultimately exhibited poor absorption in humans when tested in clinical trials was chosen. Additionally, a compound was selected that is not subject to pre-absorptive or hepatic metabolism so as to isolate absorption components of the models from pre-absorptive and metabolic factors. Gancyclovir (9-(1,3-dihydroxy-2-propoxymethyl) guanine, monosodium salt (DHPG) or Cytovene) was suitable for this purpose. Also, significant animal and human clinical data was publicly available for Gancyclovir (Jacobson et al., *Antimicrobial Agents and Chemotherapy*, Vol. 31, No. 8, p. 1251–1254 (1987); New Drug Application for Gancyclovir Sodium (Syntex, Inc. USA), obtained from the Food & Drug Administration; Drew et al., *New England Journal of Medicine*, (1995) 333:615–610; and Anderson et al., *Clinical Therapeutics*, (1995) 17:425–432 (1995)).

For development and testing of the integrated GI model, a set of training and testing lead drug compounds in various stages of human clinical testing were selected. This test set included compounds having diverse dosage requirements and ranges of permeability, solubility, dissolution and transport mechanisms, as shown below in Table 3.

TABLE 3

Compound Test Set

| Compound | Permeability | Solubility | Dose | Mechanism of Absorption |
|---|---|---|---|---|
| α1 | + + + + | + + + + | + + + + + | active |
| α2 | + + | + + + | + + + + + | paracellular |
| α3 | + | + | + + + + | unclassified |
| α4 | + | + + + + | + + | transcellular |
| α5 | + | + + + | + + + + | paracellular |
| α6 | + + + + | + + | + + + + | transcellular |
| α10 | + + + + | + + + + + | + | transcellular |
| β1 | + + + + + | + + + + + | + | transcellular |
| β2 | + + + + | + + | + + | transcellular |
| β3 | + | + | + + + | paracellular |
| β5 | + + + + | + + | + + + | unclassified |
| β6 | + | + + + + + | + + + | unclassified |

+ + + + + = greatest value & + = lowest value

Example 3

Experimental Data Collection and Processing

Experimentally derived in vivo and in vitro data was obtained as follows. To ensure quality data was used for training and validation, experimental conditions were specific enough to ensure proper data collection techniques, but flexible to allow minor and insignificant variations in individual protocols. Data sets used for model development included individual data points, i.e., raw data, that was analyzed and processed by stepwise regression analysis using a least squares minimization technique or similar fitting tool. In particular, data processing for permeability involved separation of compounds by absorption mechanism and into training and validation sets. pH dependent solubility profiles were interpolated to obtain complete profiles. For dissolution, data points were fit to determine dissolution rates. For human clinical data, data analysis and processing employed a pharmacokinetic IV/PO model and weighted least-squares analysis (See FIG. 19). The IV/PO model includes a central compartment in equilibrium with a peripheral compartment, a pre-systemic compartment re-circulated with the central compartment and for input PO doses (error function input), a hepatic compartment, as well as an IV dose and first-order elimination compartment. The plasma sample is taken from the central compartment, and the FDp sample from the hepatic compartment.

A. Human In Vivo Data-Oral (PO)

Plasma levels following oral administration (PO) in humans were used to determine the amount of compound input to the hepatic vein (FDp) as a function of time. Plasma levels of drug in humans following oral administration of drug solution or suspension after an overnight fast were used as a data set. If no solutions or suspensions were administered, formulated dosage form data were used. The PO profiles included individual data points for each patient enrolled in the study from the time of administration through 24 hours to 32 hours after administration, along with dosage. If multiple dose regimens were administered, plasma profiles for all doses were used.

B. Human In Vivo Data-Intravenous Administration (IV)

Plasma levels following intravenous administration (IV) in humans were used to determine the amount of drug input to the hepatic vein (FDp) as a function of time. IV profiles included individual data points for each patient enrolled in the study from the time of administration through 24 hours to 32 hours after administration, along with the dose. If multiple dosage regimens were administered, plasma profiles for all doses were used.

C. In vitro Permeability Data

In vitro permeability data was used to calculate drug fluxes across various regions of the intestinal mucosa. This included rabbit intestinal tissue from one or more of duodenum, jejunum, ileum and colon, and Caco-2 cells. The mechanism of transport, such as passive transcellular or paracellular, carrier-mediated absorption, carrier-mediated secretion, or mixed mechanism, was determined for several test compounds and permeabilities for each mechanism and assessed as listed in Table 4. Protocols for permeability assays are described in Example 4.

TABLE 4

Transport mechanism permeabilities and parameters for each GI region.

| Mechanism | Permeabilities | Parameters |
|---|---|---|
| Passive transcellular | Apical to basolateral (AP to BL) | $P_e$ |
| Passive paracellular | AP to BL | $P_e$ |
| Carrier-mediated absorption | AP to BL without inhibition | $K_m$, $P_c$, and $P_m$, or $P_e$ at entire concentration range |
| Carrier-mediated secretion | AP to BL and BL to AP without inhibition | $P_m$, $P_c$, and $P_m$, or $P_e$ at entire concentration range |

D. Solubility Data

Solubilities of test compounds as a function of pH were determined from pH 1.5 to 8.2 in increments of 0.1 pH units. Protocols describing conditions for solubility determination are found in Example 4. Alternatively, solubility at each pH unit from 1.5 to 8.0 was used, with a minimum of 5 data points at pH 1.5, 6.0, 6.5, 7.0, and 7.5. These solubilities were used to calculate the amount of soluble compound available for absorption across the intestinal mucosal barrier.

E. Dissolution Data

The dissolution of test compounds as a function of pH were determined at pH 1.5, 6.0, 6.5, 7.0, and 7.5. Protocols describing conditions for dissolution determination are found Example 4. The dissolution of powdered compound, and alternatively dissolution/disintegration data for the formulated dosage form used to collect oral plasma profiles were used. The dissolution data were used with solubility data to calculate the amount of drug available for absorption across the intestinal mucous within each region of the intestine.

Example 4

Protocols for Data Collection

Provided below are detailed protocols utilized for collecting and calculating data described in Example 3. These protocols were employed to ensure the quality of the data provided for development of the simulation models.

A. In Vitro Permeability Protocols

1. Diffusion Chambers

Permeability data is determined using intestinal tissue in vertical diffusion chambers similar in design to NaviCyte 8×24 mm, 9 mm Low-volume, or 9 mm round tissue diffusion chambers. The chamber system used maintains the tissue as well as the donor and receiver buffers at 37° C. Both the donor and receiver buffers within the chamber are continuously mixed throughout the experiment.

2. Mathematical Calculations

Effective permeability (Pe) is calculated using Equation 1.

$$P_e = \frac{V}{AC_0} \cdot \frac{dC}{dt} \quad (\text{Eq. 1})$$

where V is the volume of the receiver chamber (ml), A is the surface area available for diffusion (1.78 cm2 for 8×24 mm chambers, 0.64 cm2 for 9 mm round and Low-volume chambers), $C_0$ is the donor concentration, and $dC/dt$ is calculated as the slope of the regression line of the corrected receiver concentration (see Sampling) v. time plot. Two conditions must be satisfied for this equation to apply: (1) sink conditions in the receiver chamber, i.e. the accumulated concentration, must be virtually zero when compared to the donor concentration; and (2) the donor concentration must be constant ($C_0$) throughout the experiment.

The parameters for carrier-mediated absorption and secretion are calculated using Equation 3.

$$P_e = \frac{P_c}{1 + \frac{C_0}{K_m}} + P_m \quad (\text{Eq. 2})$$

where Pc is the carrier-mediated permeability, Pm is the passive permeability, Km is the affinity of the drug for the carrier, and $C_0$ is the donor concentration. Pc, Pm, and Km are calculated using non-linear regression, Pe is calculated using Equation 1, and $C_0$ is given as part of the experimental conditions. To obtain valid parameter values, Pe is determined for a sufficient number of $C_0$'s to determine Km using Equation 2 (a minimum of 6 $C_0$'s is recommended ranging between the analytical limit and the solubility limit). If Pe values are provided, the variability of the mean as well as the number of experiments performed for each concentration are provided to allow accurate regression analysis.

3. Experimental Conditions a. Buffers

Experiments are performed in appropriate, non-cytotoxic, physiological saline iso-osmotic buffers at pH 7.4 (basolateral/serosal side) or pH 6.5 (apical/mucosal side). Preferred buffers are Ringer's buffer (pH 7.4), Ringer's with glucose (pH 7.4), MES ringer's buffers (pH 6.5), or MES Ringer's with glucose (pH 6.5) (Table 5).

TABLE 5

Formulas for Ringer's buffer and Ringer's with glucose buffer.

| Chemical | Ringer's buffer (mM) | Ringer's with glucose (mM) | MES Ringers Buffer (mM) | MES Ringer's With glucose (mM) |
|---|---|---|---|---|
| KCl | 5 | 5 | 5 | 5 |
| Na$_2$HPO$_4$ | 1.15 | 1.15 | — | — |
| Na$_2$HPO$_4$ | 0.3 | 0.3 | — | — |
| NaHCO$_3$ | 25 | 25 | — | — |
| MgSO$_4$ | 1.1 | 1.1 | 1.1 | 1.1 |
| CaSO$_4$ | 1.25 | 1.25 | 1.25 | 1.25 |
| NaCl | qs iso-osmotic | qs iso-osmotic | qs iso-osmotic | qs iso-osmotic |
| MES | — | — | 25 | 25 |
| Glucose | — | 25 | — | 25 | pH adjusted with 1 N HCl or 1 N NaOH b. Sampling

Samples are collected from the receiver chamber beginning once steady state has been achieved and continuing for at least 90 minutes. Four to six (preferred) samples are collected to allow accurate determination of dC/dt (Equation 1). The volume removed from the receiver chamber at each time point is replaced with buffer containing no drug to maintain constant volume in the receiver chamber. The dilution of the receiver concentration due to the addition of buffer is corrected during data analysis and Pe calculation. The concentration may be corrected by: (1) adding the mass removed at each sampling time to the mass removed from the receiver chamber at all prior sampling times, by summing calculated mass absorbed and adding to mass for sample calculation; and (2) using Equation 3 (preferred).

$$\frac{1}{X} = -\sum_{n}^{k}(-1)n\frac{\beta\,(S)^{n-1}}{n\,(V)} \quad (\text{Eq. 3})$$

where the corrected receiver chamber concentration is obtained by dividing the collected sample concentration by Equation 3 (1/X), S is the volume of sample withdrawn, V is the receiver chamber volume, k is the sequential sample number, i.e., k=1 for the first sample time, k=2 for the second sample time, k-3 for the third sample time, etc., and β is the corresponding number from Pascal's triangle (Table 6).

TABLE 6

Pascal's Triangle for determining β coefficients.

| Sample | 1$^{st}$ term | 2$^{nd}$ term | 3$^{rd}$ term | 4$^{th}$ term | 5$^{th}$ term | 6$^{th}$ term |
|---|---|---|---|---|---|---|
| 1 | 1 | | | | | |
| 2 | 1 | 1 | | | | |
| 3 | 1 | 2 | 1 | | | |
| 4 | 1 | 3 | 3 | 1 | | |
| 5 | 1 | 4 | 6 | 4 | 1 | |
| 6 | 1 | 5 | 10 | 10 | 5 | 1 |

Donor concentration ($C_0$) is determined by sampling the donor buffer containing the test compound with subsequent analysis directly from the donor chamber, or from a stock solution of donor buffer provided binding and absorption to the interior of the chambers does not occur.

c. Intestinal Tissue

Rabbit intestinal tissue is used for permeability experiments. During mounting of tissue onto chambers, intestinal muscles are stripped off the mucosa and discarded. Care should be taken to ensure integrity of the tissue. A minimum of three chambers are used to determine $P_e$ values for each region, concentration and compound. The mean $P_e$ and Standard Error of the Mean are provided for each study.

d. Cell Monolayers

Caco-2 cell monolayer Pe is determined in diffusion chambers similar to NaviCyte Snapwell™ diffusion chambers and follow all procedures described above except the recommended buffers are Ringer's with glucose or MES Ringer's with glucose as listed in Table 6.

Caco-2 cells are grown using DMEM media supplemented with 10% FBS, 5% PCN-STEP, and 1% NEAA under 95–100% humidity and 5% CO$_2$ at 37° C. Cells are grown in flasks and the culture split at 85–95% confluence. Snapwells™ are seeded at 65,000 cell/cm$^2$ and used in the permeability experiment within 21–28 days post seeding to allow for differentiation.

4. Determination of Absorption Mechanism

Absorption mechanism for a compound is determined by one of the following methods. Determination of $P_e$ in both the apical-basal (AB) to basal-lateral (BL) and BL to AB directions using Equation 1, or determination of $P_e$ in the AB to BL direction at concentrations, (a) close to the analytical limit, and (b) close to the solubility limit.

Similar $P_e$ values in both the AB to BL and BL to AB indicate a passively absorbed compound and no further studies are required. AB to BL $P_e$ greater than BL to AB indicates carrier-mediated absorption and $P_e$ must be determined for 5 additional $C_0$ in the AB to BL direction. BL to AB $P_e$ greater than AB to BL indicates carrier mediated secretion and $P_e$ determined for 5 additional $C_0$'s in the BL to AB direction.

Similar $P_e$ values at low and high concentrations indicate a passively absorbed compound, and no further studies are required. Low concentration $P_e$ higher than high concentration $P_e$ indicates carrier-mediated absorption and Pe is determined for 5 additional $C_0$'s in the AB to BL direction. High concentration $P_e$ higher than low concentration $P_e$ may indicate carrier-mediated secretion. BL to AB $P_e$ is then determined at the low concentration and the mechanism determined as described above.

B. Solubility Determination

Solubility of a compound is determined using an accurate and scientifically sound method similar to the Phase Rule and Phase-solubility analysis as described in Remington's: The Science and Practice of Pharmacy, 19$^{th}$ edition, Chapter 16.

The solubility is determined at pH 1.5 using Simulated Gastric Fluid (USP XXII) minus pepsin. Solubility at pH 6.0, 6.5, 7.0, and 7.5 is determined in Simulated Intestinal Fluid (USB XXII) minus pancreatin. Parameters are for data collection are carefully monitored by ensuring purity of the test compound and accuracy of the Simulated Gastrointestinal fluids. A temperature of 37° C. is maintained accurately during the course of the determination. Complete saturation and accurate analysis of saturated solutions are employed.

C. Dissolution Determination

The dissolution rates are determined using the equipment, apparatus, and methods described in USP XXII, <711> dissolution. The dissolution rate at pH 1.5 is determined in Simulated Gastric Fluid (USP XXII) minus pancreatin. Concentrations are collected and analyzed for drug compound from the vessel for a sufficient time (6 hours, preferable) to allow the initial slope of the concentration v. time curve to be determined. The slope (dissolution rate) is determined using the initial linear portion of the concentration v. time plot if non-sink conditions exist. Under sink conditions, the entire plot are used to calculate the slope. The slope is reported as the dissolution rate. Explanations of the dissolution rate, sink and non-sink conditions, and equations for calculation are given in Remington's: the Science and Practice of Pharmacy, 19th edition, Chapter 34.

If a formulated dosage form is used for dissolution testing, the dissolution protocols described are used to determine the dissolution rate for drug compound from the formulated dosage form.

Example 5

Standards and Protocols for Evaluating Permeability Data Collection

This example provides detailed protocols for controlling the quality of permeability data collection described in Examples 3 and 4. Compounds listed in Table 7 are used as standards for monitoring permeability data collection and quality. The compounds were chosen to represent each intestinal transport mechanism (passive transcellular, passive paracellular, carrier-mediate influx, or carrier-mediated efflux).

TABLE 7

Permeability Standards

| Transport mechanism | Compounds |
| --- | --- |
| Passive Paracellular | mannitol |
| Passive Transcellular | hydrocortisone |
| Carrier-mediated Influx | D-glucose |
| Carrier-mediated Efflux | etoposide |

Mannitol, hydrocortisone, D-glucose, and etoposide also were chosen since they are widely used as markers for intestinal transport across rabbit tissue and other systems with well characterized Pe values. These compounds also are available commercially as either 3H-labeled or 14C-labeled.

Permeability data for standards is compared to the values for rabbit listed in Table 8 (or other standard values) using basic statistical analyses. If the data is significantly different (p-value >0.05) for any of the standard compounds, data collection is repeated.

TABLE 8

Transport Characteristics of Permeability Standards*

| Compound (donor concentration) | Pe (cm/s) | | | |
| --- | --- | --- | --- | --- |
| | Duodenum | Jejunum | Ileum | Colon |
| mannitol (1 mM)5 | $1.73 \times 10^{-6}$ | $3.54 \times 10^{-6}$ | $4.02 \times 10^{-6}$ | $5.53 \times 10^{-6}$ |
| hydrocortisone (0.01 µM)5 | $3.00 \times 10^{-7}$ | $1.31 \times 10^{-6}$ | $2.91 \times 10^{-6}$ | $3.85 \times 10^{-6}$ |
| D-glucose (10 mM)5 | $4.55 \times 10^{-6}$ | $1.02 \times 10^{-5}$ | $1.45 \times 10^{-5}$ | $9.28 \times 10^{-6}$ |
| etoposide (100 µM) | | | | |

*Note:
permeability values are representative of ranges. Other values or extended ranges may be used.

A. Experimental Conditions

Protocols, conditions and calculations for permeability evaluation of standards are as described in Example 4, with the following modifications.

Permeability experiments are performed using Ringer's buffer at pH 7.4 on both the apical/mucosal and basolateral/serosal sides. Ringer's buffer is as described above excepting that glucose is substituted with mannitol when Pe values for glucose are being measured.

Samples are collected from the receiver chamber beginning 30 minutes after experiment initiation and continuing every 15 minutes until 6 samples have been collected (105 minutes). One-half ml is removed from each receiver chamber at each time point and compound concentration determined. The volume removed from the receiver chamber is replaced with buffer containing no drug to maintain constant volume in the receiver chamber. The dilution of the receiver concentration due to the addition of buffer should be corrected during data analysis and Pe calculation. The concentration is corrected by using Equation 4.

$$\frac{1}{X} = \sum_{n=1}^{k} (-1)^{n-1} \frac{\beta}{k+1} \left(\frac{S}{V}\right)^{n-1} \qquad \text{(Eq. 4)}$$

Where the corrected receiver chamber concentration is obtained by dividing the collected sample concentration by Equation 4 (1/X), S is the volume of sample withdrawn, V is the receiver chamber volume, k is the sequential sample number, i.e. k=1 for the first sample time, k=2 for the second sample time, k=3 for the third sample time, etc., and β is the corresponding number from the modified Pascal's triangle below (Table 9). Note: Since the sample intervals are not even (i.e. the 1st interval is 30 minutes, all others 15 minutes) Equation 4 as well as the β coefficients are modified from those listed in Example 4.

TABLE 9

Modified Pascal's Triangle for determing β coefficients

| Sample | 1st term | 2nd term | 3rd term | 4th term | 5th term | 6th term |
|---|---|---|---|---|---|---|
| 1 | 2 | | | | | |
| 2 | 3 | 2 | | | | |
| 3 | 4 | 5 | 2 | | | |
| 4 | 5 | 9 | 7 | 2 | | |
| 5 | 6 | 14 | 16 | 9 | 2 | |
| 6 | 7 | 20 | 30 | 27 | 11 | 2 |

The donor concentration $C_0$ is determined by sampling 0.02 ml of the donor buffer containing drug (with subsequent analysis) directly from the donor chamber. Potential binding of drugs to the chambers also is monitored. Donor samples (0.02 ml) are taken at experiment initiation and at experiment conclusion. If a significant decrease in drug concentration has occurred (>10%) the experiment is repeated using procedures which compensate for the drug loss in the donor chamber. It is recommended that the donor chamber solution be removed and replaced with fresh donor buffer containing drug at appropriate intervals. The intervals and volumes to be used are determined using sound scientific judgment. Adequate data is collected to show the donor drug concentration has remained constant throughout the experiment.

For tissue-based permeability assays, during mounting of tissue onto chambers, intestinal muscles should be stripped off the mucosa and discarded. Care should be taken to ensure integrity of the tissue.

Animals donating tissue are euthanized immediately prior to experiment initiation. The small intestine is excised from the animal and kept in ice cold Ringer's buffer pH 7.4 until mounted in diffusion chambers. As soon as possible after excision, the tissue is cut into an appropriately sized piece and placed over the diffusion chamber pins with the mucosal side down. The muscle layers are carefully stripped away using forceps. After the tissue is mounted the two half chambers are placed together and the donor and receiver sides filled with the appropriate pre-warmed (37° C.) buffer. If NaviCyte chambers are used, the gas lift system is connected with 95% $O_2$/5% $CO_2$ flowing at ~5-15 ml/min (depending upon chamber volume) into each half chamber to maintain pH and mixing. Sampling begins 30 minutes after connection of the gas lift system.

The mean Pe and Standard Error of the Mean are determined for each study. Permeabilities from at least 6 chambers from 3 different animals are used in calculating the mean and Standard Error of the Mean.

In addition, the Pe of radiolabeled mannitol is determined simultaneously with the standard compound as a marker of intestinal integrity. Mannitol Pe values may be determined by concurrent diffusion using a donor buffer containing mannitol and the standard drug compound, or by continuing the experiment for 60 minutes after the last standard compound sample is collected using donor buffer containing mannitol and fresh receiver buffer containing no compounds.

Special experimental conditions are followed for certain standard compounds. This includes such conditions as a proton gradient, a sodium gradient, presence of glucose, etc. These conditions are listed in Table 10 and are substituted or added to the general conditions listed above.

TABLE 10

| | Experimental Conditions | |
|---|---|---|
| Standard Compound | Donor Concentration | Special Conditions |
| mannitol | 1 mM | |
| D-glucose | 10 mM | |
| hydrocortisone | 0.01 µM | |
| etoposide | 100 µM | drug dissolved in DM50, DMSO concentration in buffer < 0.1% |

Example 6

Physiologic-Based Mass Simulation Model

A. Design

A multi-compartment physiologic-based simulation model (the "mass-model") was designed to integrate mass-flow relationships among GI compartments representing the stomach, duodenum, jejunum, ileum, and colon, and thus throughout the GI tract, and to characterize drug movement in units of mass into peripheral compartments. Converters that interrelated transfer rates and associated rate constants (kt), which in turn were modified by various factors including pH, solubility profiles, compartment surface area and drug permeability were incorporated to account for drug movement among compartments. A plasma kinetics model also was included for validation purposes and for correlating clinical plasma data to the mass model. Converters also were used for unit conversion.

Gancyclovir was chosen to develop and test the mass model. Gancyclovir exhibits no in vivo biotransformation and is poorly absorbed. Thus, the mass model assumes no metabolism or protein binding. Additionally, dissolution rate and delivery system were not used in the mass model as modifying parameters of drug absorption, i.e., drug assumed to be completely dissolved in the stomach and solubilized according to its solubility profile.

Surface area values for each compartment of the mass model represented a "functional surface area," as opposed to an absolute value. A functional surface area was utilized since (1) fluids entering the gastrointestinal compartments do not cover the surfaces of the compartment instantaneously, but rather over a time course; and (2) solubilized drug within the fluid is not ideally presented to all absorptive areas. Functional surface areas for each compartment were calculated by solving Equation 5 for the area using various data inputs from the literature.

$$P \cdot A \cdot S_p = \partial M / \partial t \qquad \text{(Eq. 5)}$$

Where P is the permeability coefficient, A is the surface area of the membrane, $S_p$ is the solubility of the drug in the relevant segment of the intestine, and $\partial M/\partial t$ is drug flux, where flux $\partial M/\partial t$ is determined from the permeability of the drug in the particular intestinal compartment, the surface area covered by drug solution and the solubility of at the pH of the intestinal compartment.

For example, several studies have been conducted comparing permeability of various compounds (Rubas et al., *Pharmaceutical Research*, Vol. 10, No. 1 (1993)). Mannitol, which has similar physicochemical properties to Gancyclovir, also has similar permeability characteristics and a bioavailability of approximately 10% in humans when it is orally administered. For mannitol, permeability is well characterized. Thus, data obtained from the literature related to permeability in each compartment, pH-dependent solubility and mass concentration relationships was used to solve Equation 5 for area. Thus, it was this area, and not the theoretical total surface area of each compartment, that was used as the functional area of a compartment, which represented a good approximation of in vivo surface area relationships for initial model building.

Permeability values were obtained from published in vitro cell diffusion experiments and were accounted for by converters that modified luminal and peripheral flow (K12) for each compartment. For solubility, a solubility curve was used based on experimental data available in the literature. pH was then isolated in a separate converter to modify the solubility curve for the particular compartment. In contrast, for validation purposes, an absolute solubility value was used and pH was entered as 1 to isolate that converter from the validation model.

Absorption "transfer" rates among each two compartment sub-system were collected into a separate flow representing total absorption rate, which in turn was collected into a compartment representing the total amount of drug absorbed for each GI tract compartment, namely, stomach, duodenum, jejunum, ileum, and colon. Absorption rates among stomach, duodenum, jejunum, ileum, and colon modules were connected by flows modified by the associated rate constants between each GI segment.

For validation purposes, a plasma kinetics model was integrated with the mass-flow compartments by linking the total absorption rate to a flow representing the absorption rate constant, which in turn fed into the central plasma compartment. A standard two-compartment plasma kinetics model (Ramsay, *European Journal of Pharmaceutics and Biopharmaceutics*, Vol. 37, No. 3 (1991)) was used for this purpose. (See FIGS. 9 and 10) The plasma kinetics model incorporated first order transfers between the blood compartment and peripheral compartment. Two flows were used and set up as first order systems and thus different rate constants were applied in each direction. Compartment values were represented as mass units. Blood volume was input in a converter, which modified a converter for concentration along with the mass compartment. An elimination rate constant was also obtained form the literature in a first order process. In addition, while most drugs are given in milligram doses, plasma concentrations are reported in microgram or nanogram per milliliter. This is done since compounds are distributed rapidly into a large volume after entering the blood resulting in a concentration of drug in systemic circulation that is quite low with respect to the concentration at the site of administration. Accordingly, an additional converter was added to convert milligram units to nanogram or microgram units expected for concentrations of the test compound based on human bioavailability data. A compartment also was added to collect elimination data.

B. Mass Model Parameters

Parameters and associated values of the mass model include pH, solubility, permeability, and intestinal transit, and are illustrated in Table 11.

TABLE 11

Mass Model Parameters/Values

| Parameter | Value |
|---|---|
| Dose | 1000 mg |
| dt | 0.125 |
| Run Time | 24 hrs |
| ka assumed (mass transit) | 2.8 or 3 |
| Stomach | |
| Area | 50 cm$^2$ |
| Solubility | 31 mg/ml |
| Permeability | 1.1 × 10$^{-6}$ cm/sec |
| Duodenum | |
| Area | 125 cm$^2$ |
| Solubility | 3.65 mg/ml |
| Permeability | 1.1 × 10$^{-6}$ cm/sec |
| Jejunum | |
| Area | 182 cm$^2$ |
| Solubility | 3.65 mg/ml |
| Permeability | 2.17 × 10$^{-6}$ cm/sec |
| Ileum | |
| Area | 102 cm$^2$ |
| Solubility | 3.65 mg/ml |
| Permeability | 4.06 × 10$^{-6}$ cm/sec |
| Colon | |
| Area | 138 cm$^2$ |
| Solubility | 3.65 mg/ml |
| Permeability | 3.80 10$^{-6}$ cm/sec |
| Plasma Kinetics | |
| $k_{12}$ | 0.839 |
| $k_{21}$ | 0.670 |
| $k_{elim}$ | 0.161 |
| Fluid Volume | 76,800 ml |

The mass model also was tested by inputting values derived from the literature (Gibaldi et al., *Pharmacokinetics*, pp. 284–288, Marcell Dekker (1975)) into the plasma kinetics model. These values are shown in Table 12.

TABLE 12

Values for Plasma Kinetic Module

| Dose | 1 g |
|---|---|
| 1505a | 2.718 h$^{-1}$ |
| 1505b | 0.254 h$^{-1}$ |
| $k_{21}$ | 0.3737 h$^{-1}$ |
| $k_{12}$ | 0.7509 h$^{-1}$ |
| $k_{10}$ | 1.3474 h$^{-1}$ |
| $V_p$ | 20.1241 |

Example 7

Testing and Validation Mass Model

The mass model was tested using parameters shown in Table 11 with an initial dose of 1000 mg over a time course of 24 hours. AUC, $C_{max}$, $T_{max}$, and $T_{1/2}$ were simulated using various doses (New Drug Application for Gancyclovir Sodium, Syntex (USA), (obtained from the FDA under the Freedom of Information Act (FIA)) and compared to human clinical data obtained for Gancyclovir. Bioavailability simulated by the mass model for Gancyclovir was approximately 6%. Compared to human clinical data, obtained for two Phase I clinical studies (designated here as ICM 1505 and 1505b), bioavailability of fasted patients in clinical trials typically ranged from 3–20%. The mass model also was tested using a plasma kinetics validation model illustrated in FIG. 9.

Figure 17:
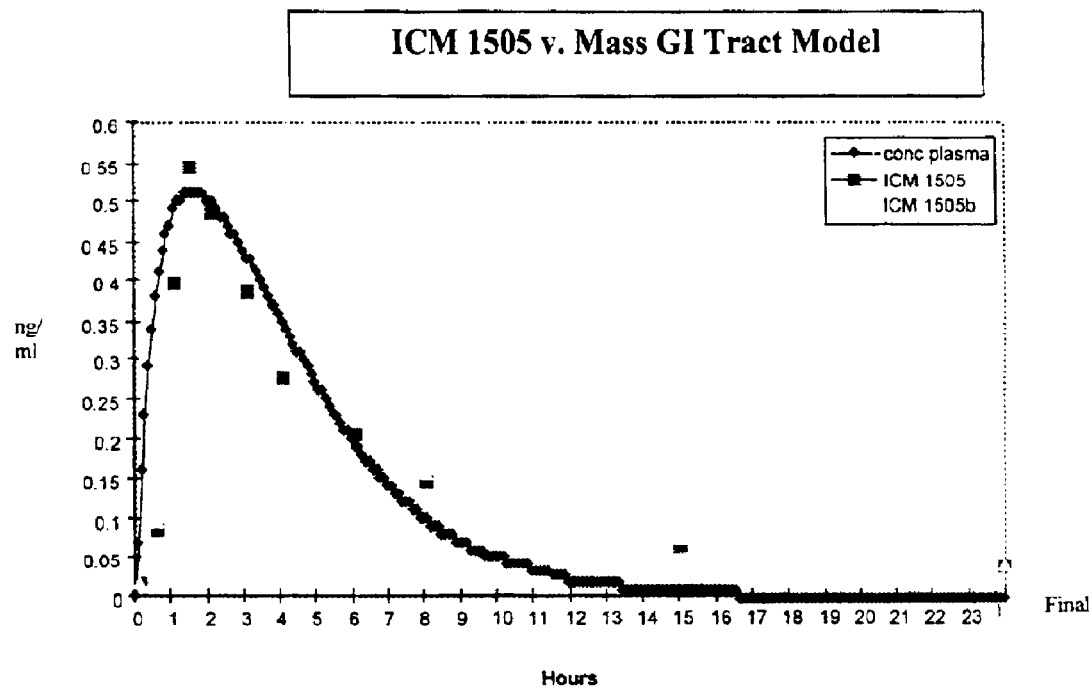
FIG. 17 compares plasma concentration profiles derived from clinical studies of gancyclovir and simulation using volume GI tract simulation model of the invention.

FIG. 17 shows the area under the concentration time curve for a 1000 mg dose of Gancyclovir, Tmax=1.4 hrs, Cmax=0.51 ng/ml., using the mass model, as compared to clinical study data of ICM 1505 and 1505b. The results demonstrate that the mass model underestimated plasma concentration during the post-absorptive period. Table 13 shows comparison of some values between clinical studies and those predicted by the mass model. The clinical studies also used a 70 Kg body weight for normalization of concentrations.

TABLE 13

Comparison of Mass Model to Clinical data

| Parameter | Mass Model | Clinical 1505a | Clinical 1505b |
|---|---|---|---|
| Cmax (mcg/ml) | 0.51 | 0.55 | 0.59 |
| Tmax (hrs) | 1.40 | 1.43 | 1.43 |

Example 8

Physiologic-Based Volume Simulation Model

A. Design

A physiologic-based simulation model for incorporating fluid volume flux and GI transit was developed for integration with the mass model to account for changes in absorption resulting from fluid absorption/secretion and transit, and thus apparent drug concentration. The volume model was constructed so that fluid enters a compartment and was absorbed by a first order process based on an absorption rate for that fluid. Movement of fluid between compartments was dependent on a zero or first order fluid transit rate.

B. Volume Model Parameters

As a starting point for the volume model, values were obtained from literature that described in general terms absorption and secretion of fluid throughout the body (Change et al., *Gastrointestinal, Hepatobiliary and Nutritional Physiology*, Chapter 5, p. 92, Lippincott-Raven (1996)). Values representing total intake of fluid per day and total secretion of fluid per day were modeled into the system normalized linearly to increments of dt for the model. To permit for changes in dt for the model, the values were entered as pulses. Values used in the volume model are shown in Table 14.

TABLE 14

Volume Model Parameters/Values

| Source | ml/24 hrs | ml/0.1 hrs |
|---|---|---|
| Intake/Secretion | | |
| Stomach | 6500 | 27.08 |
| Orally | 2000 | 8.33 |
| Salivary Glands | 1500 | 6.25 |
| Stomach | 2500 | 10.42 |
| Duodenum | 2000 | 8.33 |
| Bile | 500 | 2.08 |
| Pancreas | 1500 | 6.25 |
| Jejunum/Ileum | 1000 | 4.17 |
| Jejunum | 641 | 2.67 |
| Ileum | 359 | 1.50 |
| Colon | 0 | 0 |
| Total Absorption | 9000 | 337.57.5 |
| Duodenum | 2598 | 10.82 |
| Jejunum | 3783 | 15.76 |
| Ileum | 2120 | 8.83 |
| Colon | 400 | 1.67 |
| Total | 8900 | 37.09 |

Note:
Values for compartments based on %total intestinal area

Where data was only available for a series of compartments, values were assigned to each compartment based on the percentage of the total area for that series (e.g. secretions for jejunum and ileum and absorption for parts of the small intestine). The model was set as two flows between the blood (serosal) side of the compartment and the compartment itself. Each flow represented the rate constant for secretion and fluid absorption.

For development purposes, absorption and stomach secretion were assumed to be zero order when using values from Table 14 for both flows. Also, daily volume for fluid entry into the stomach was entered as a pulse according to the dt values shown in Table 14. Thus, total intake and secretions of fluid was modeled as a pulse occurring every 6 minutes throughout a 24 hour period. Initial volume in the stomach also was set up as a pulse of the total oral intake, salivary excretion, and stomach secretion over each dt increment.

Example 9

Testing and Validation of Volume Model

To test movement of fluid between compartments the volume model was modified to approximate zero order fluid transit or emptying and isolated from the mass component of the model. Initial values of 1000 ml and 250 ml were used for testing.

Example 10

Physiologic-Based Mass-Volume Simulation Model

A. Design

Figure 9:
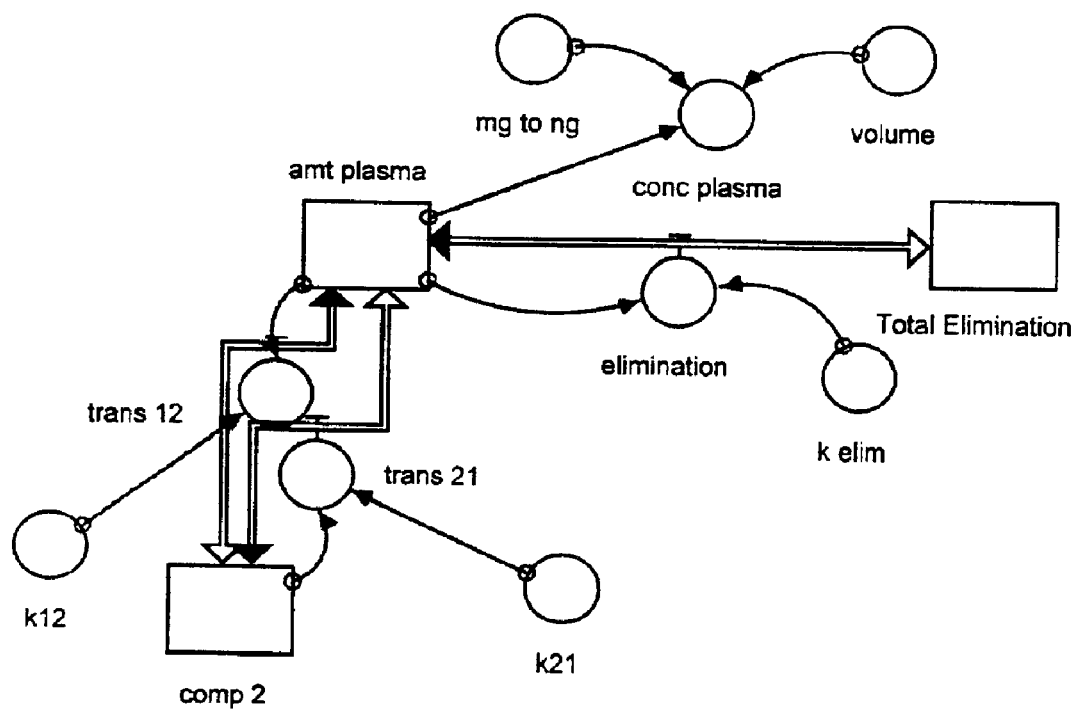
FIG. 9 is a graphical compartment-flow diagram illustrating the plasma simulation model of FIG. 5 and exemplary relationships among compartments, flow regulators, converters and input links.

A physiologic-based simulation model integrating the mass and volume models (the "mass-volume model") was constructed to integrate complex mass and fluid flow relationships. The integrated mass-volume model also included compartments to characterize drug movement into peripheral compartments. A plasma kinetics model for training/validation purposes also was included. The basic design for the integrated mass-volume model, linked to the plasma kinetics model shown in FIG. 9, is illustrated in FIG. 12.

Volume for a compartment was added as a product to obtain the amount of drug solubilized at a time increment volume. Additionally, an "IF . . . THEN . . . ELSE" control statement was added to prevent the equation from indicating that more drug was solubilized than dosed. Thus, the integrated mass-volume model shows the mass of drug in the stomach connected to the absorption rate constant as well as the volume compartment.

Mass and fluid transit rate constants of 2.8 and 3 for the stomach were calculated from values obtained from the literature for Gancyclovir (Syntex, Clinical Studies ICM 1653 and 1774, FDA NDA available data and Bachrach et al., Functional and Diagnostic Aspects of the Upper Digestive Tract, *Digestive System, Part I, Upper Digestive Tract*, Netter (1989)), and determined for each of the remaining compartments to approximate mass and fluid movement.

B. Mass-Volume Model Parameters

Parameters and associated values and equations were systematically varied or as described above for individual mass and volume models; an example of the equations and parameters employed in the mass-volume model are shown in Appendix 1. Dissolution rate and delivery system (controlled release device/formulation) were excluded from in the mass-volume model, and thus the model assumes a test compound is immediately in solution in the stomach.

Example 11

Testing and Validation of Mass-Volume Model

The mass-volume model was tested using the equations and parameters shown in Appendix 1. These parameters included the pulsed estimate of fluid absorption and gastrointestinal secretions, and rate constants extracted from the literature. Alternate sets of parameters for fluid absorption and secretions also were tested. For example, simple zero and first order rate constants of 1 or a sequential integer and various doses were evaluated for comparison to human clinical data.

Figure 18:
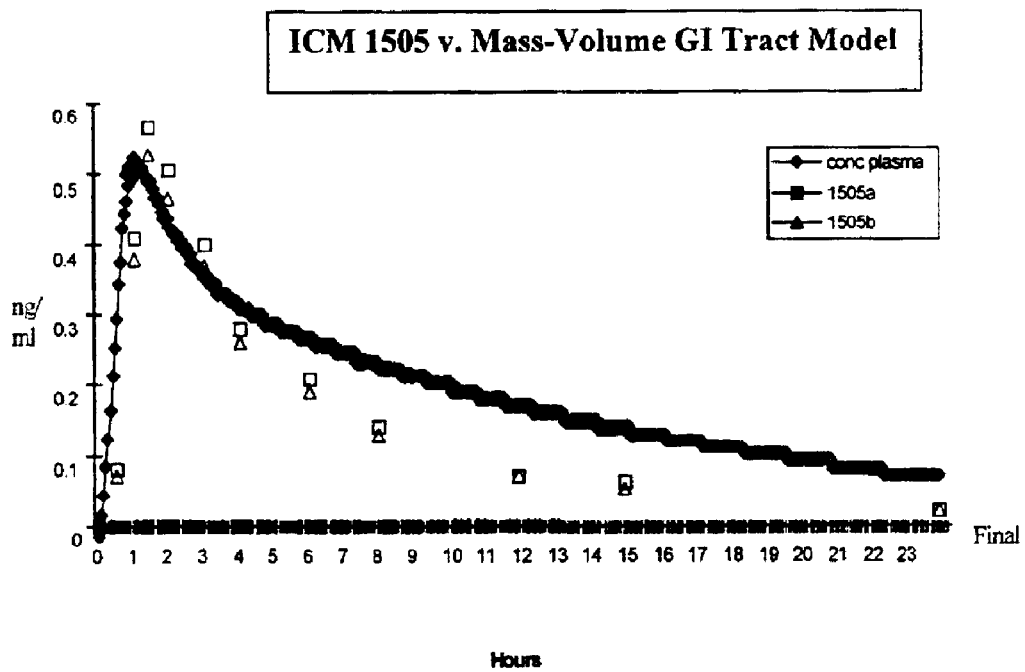
FIG. 18 compares plasma concentration profiles derived from clinical studies of gancyclovir and simulation using mass-volume GI tract simulation model of the invention.

FIG. 18 shows the area under the concentration time curve for a 1000 mg dose of Gancyclovir, Tmax=1.1875 hrs, Cmax=0.54 mcg/ml., using the mass-volume model of FIG. 12 with the estimated absorption and secretion rates, relationships, and values of Appendix 1, as compared to clinical study data of ICM 1505 and 1505b. The data is now less favorable for Tmax but more favorable for AUC compared to the mass model. These results demonstrate that the mass model underestimated plasma concentration during the post-absorptive period, while the combined mass-volume model appeared to overestimate it.

The mass-volume model was modified to incorporate simple zero and first order absorption and secretion. This model was then run using an initial volume of 250 ml and also 4 administrations of 250 ml water as done during clinical studies Results were similar to the results shown in FIG. 18, but with slightly higher absorption.

The mass-volume model also was run using the following combinations of data input: (1) doses of 500 mg, 750 mg, 1000 mg at qid, bid, and tid dosing; (2) initial volumes of 250 ml, 500 ml, 1000 ml; (3) varying absorption and secretion rates based on differing assumptions for daily secretion and fluid intake; (4) varying pH values in the various compartments; and (5) simulation of food intake and fasting conditions. Correlation was very good with some clinical data and less than optimal with others. Correlation with theoretical estimations also varied from very good to poor.

Collectively, the mass-volume model represented an improvement over the individual mass and volume models in that it provided a better approximation of in vivo conditions. While the simpler mass-model correlated better with clinical data, the integrated mass-volume model was more sensitive to changes in the various input parameters, physiological conditions and underlying constants, and thus a more rigorous model of the GI tract.

Example 12

Physiologic-Based GI tract Simulation Model

A. Design

The mass-volume model was selectively improved in a stepwise fashion to create an integrated physiologic-based simulation model of the GI tract of a mammal (the "GI model") capable of compound-independent prediction of oral absorption with a high level of accuracy. The model was developed to be flexible. That is, it was designed so that additional physiological factors that influence oral absorption could be identified and incorporated into the model as needed to improve the quality of the prediction for a diverse set of test compounds. Additionally, the GI model was developed to minimize input data requirements.

Figure 21:
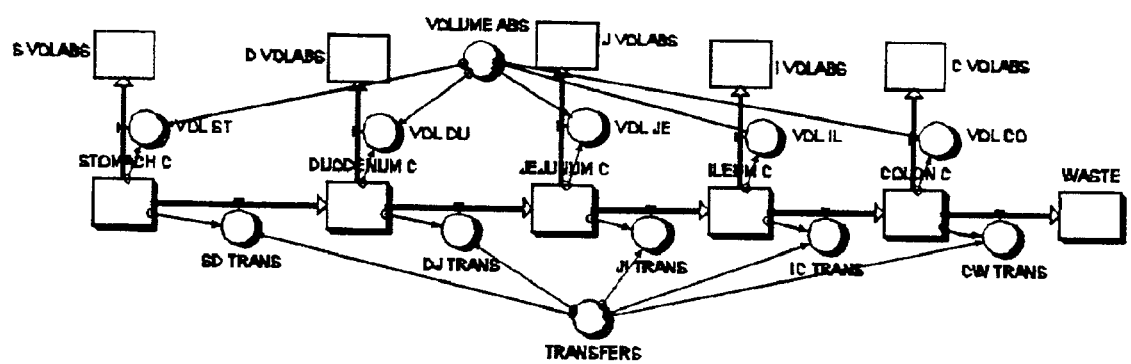
FIG. 21 shows graphical compartment-flow diagram illustrating the GI track fluid transit model component of the PK tool and method of the invention.
Figure 22:
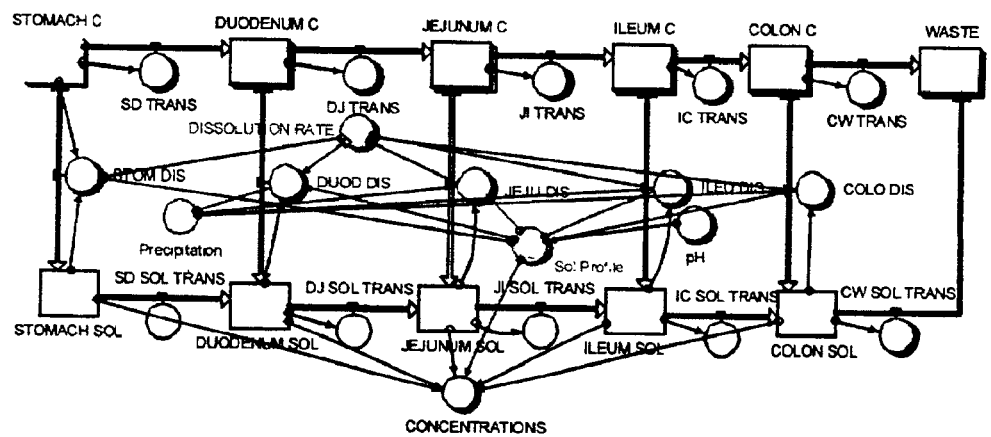
FIG. 22 shows graphical compartment-flow diagram illustrating the GI track solubility-dissolution model component of the PK tool and method of the invention.
Figure 23:
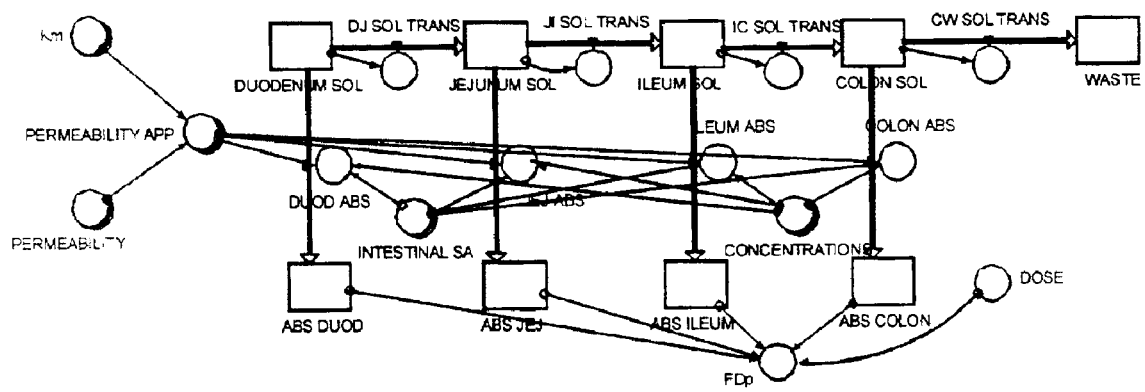
FIG. 23 shows graphical compartment-flow diagram illustrating the GI track absorption model component of the PK tool and method of the invention.
Figure 24:
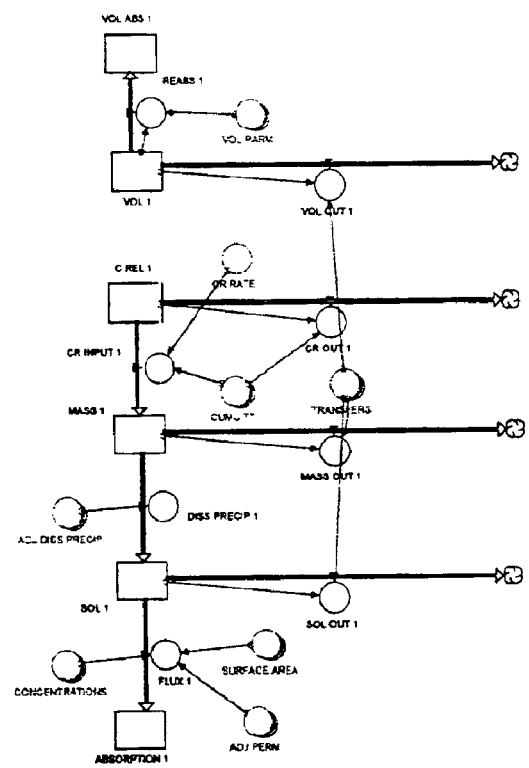
FIG. 24 shows graphical compartment-flow diagram illustrating integration of the GI track fluid transit model, solubility-dissolution model, and absorption model components for one GI segment of the PK tool and method of the invention.
Figure 25:
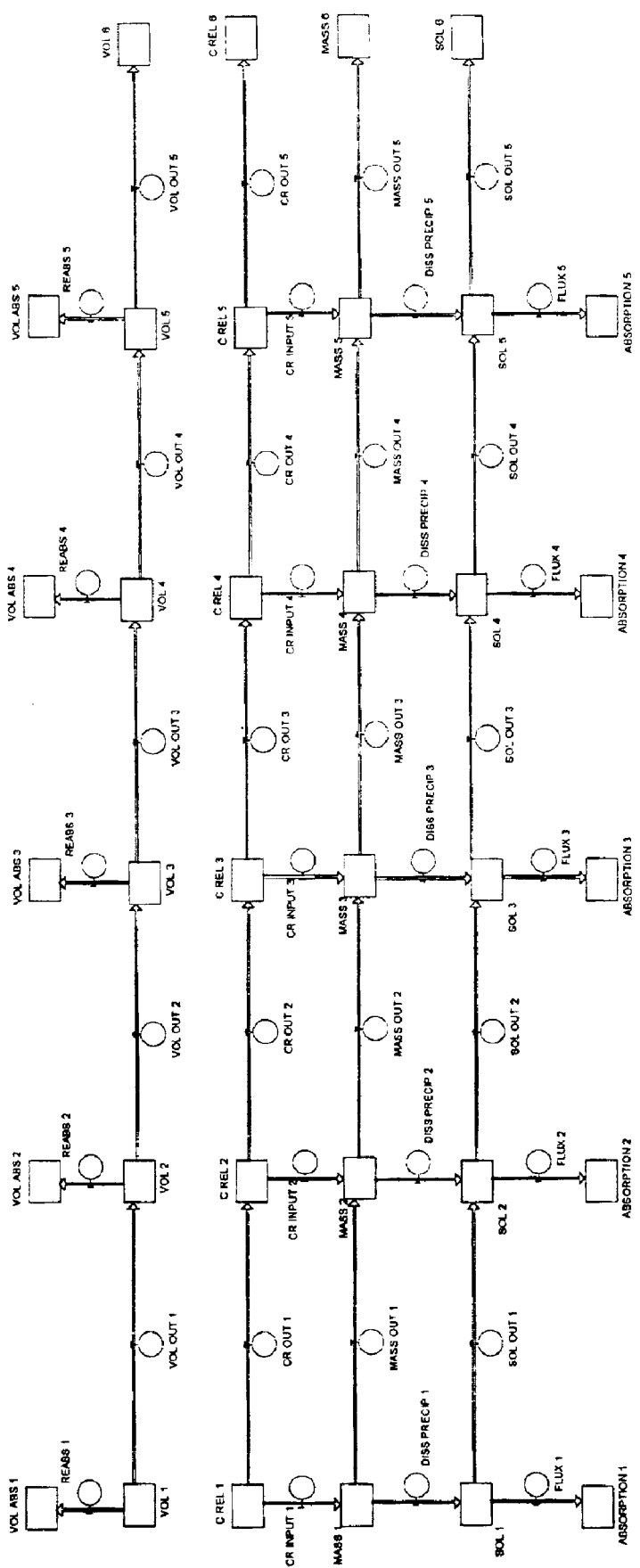
FIG. 25 shows graphical compartment-flow diagram illustrating integrated GI track simulation model components (without converters or input link connectors) of the PK tool and method of the invention.
Figure 26:
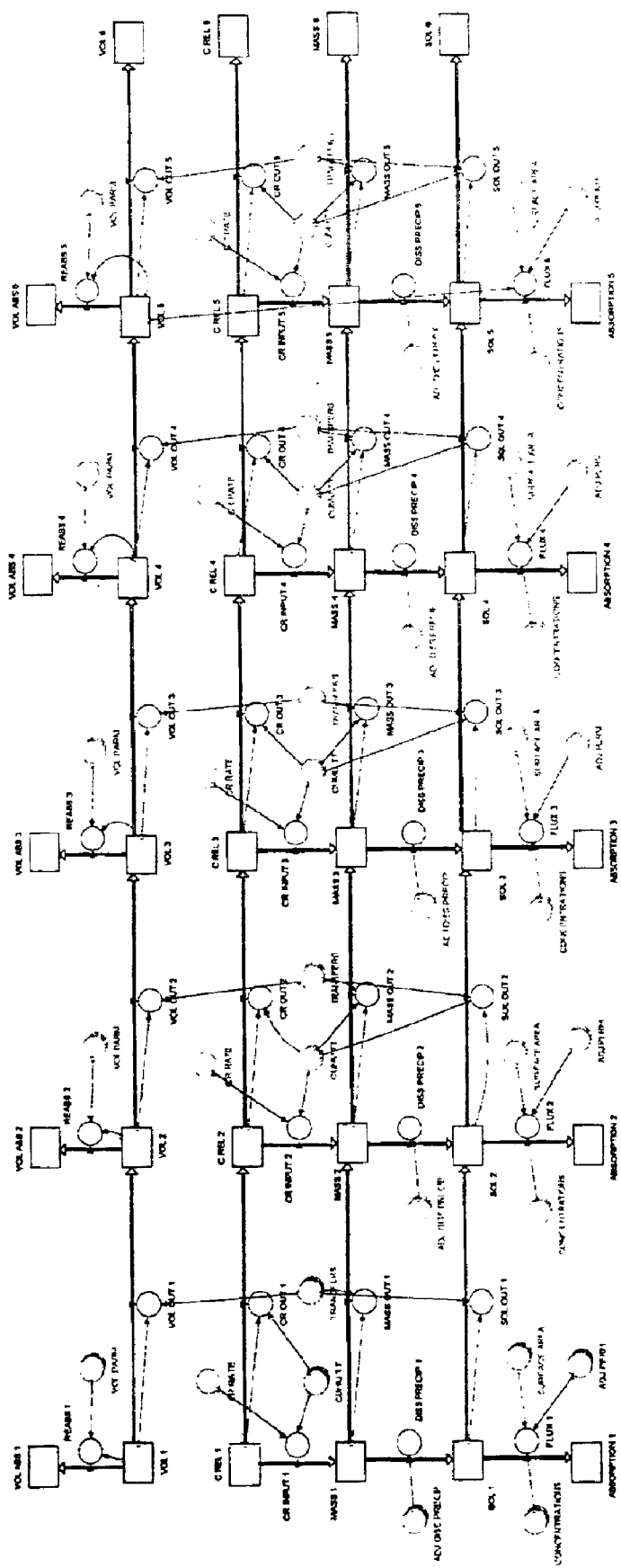
FIG. 26 shows graphical compartment-flow diagram illustrating integrated GI track simulation model components (with converters and input link connectors) of the PK tool and method of the invention.

The basic approach involved generation, testing and integration of a GI transit model (FIG. 21), a pH-dependent solubility and dissolution model (FIG. 22), and an absorption model (FIG. 23), as well as underlying equations and parameters, constants, calculated parameters, and rules by which a given simulation is to proceed. A controlled release device and formulation compartment also was included. A graphical compartment-flow model of the integrated GI model is illustrated in FIG. 25 (without converters, ghost or connectors) and FIG. 26 (with converters, ghost and connectors). Parameter inputs, calculations and outputs are illustrated in FIGS. 30–40. An abbreviation key for the GI model is provided as Appendix 3.

The GI model also incorporated additional features to improve the predictive power and versatility of the simulation model. One feature was the development and incorporation of regression analysis derived adjustment parameters based on analysis and processing of human clinical data and in vitro data for a diverse set of compounds. The adjustment parameters were utilized as constants in the GI model, and thus modify underlying equations of the model. A second feature was development and incorporation of regional permeability correlation parameters and equations that permitted estimation of values for segments of the model that were missing user provided input values for corresponding parameters. This facilitates prediction of oral drug absorption when permeability values or other parameter for a given compound are provided for a to limited number of GI segments, for example, when cell-based input data, such permeability data derived from Caco-2 cells is used to provide permeability input data of colon. Another feature was development and incorporation of parameters and calculations to account for transport mechanism and thus transport-specific variations in compound absorption. Another feature was incorporation of the ability to isolate and evaluate specific regional absorption events related to dissolution and mass transit. Also, the GI model was developed to separate absorption into the portal vein (FDp) from hepatic metabolism, so as to account for individual primary barriers to absorption.

B. GI Model Equations, Rules and Parameters

1. General Equations For GI Model:

Various differential equations and rules utilized for the GI tract model are provided below. For the equations, adjustment parameters are designated by the letter Z.

Transit Time:
First Order Transit Process $$\frac{dA}{dt} = k_{TT}[A] \quad \text{(Eq. 6)}$$

dA/dt=rate of transit (or absorption), $k_{TT}$=rate of constant, A=amount (compound or water) in proximal compartment.
Rate Constant Calculation $$k_{TT} = \frac{\ln 10}{TT_{ADJ}} \quad \text{(Eq. 7)}$$

$TT_{ADJ}$=adjusted transit time $$TT_{ADJ} = (TT_p \cdot Z_{TT} \cdot \text{User}_{TT}) \quad \text{(Eq. 8)}$$

$TT_p$=physiological transit time, $Z_{TT}$=transit time adjustment parameter, $\text{User}_{TT}$=User controlled adjustment to transit time.
$K_{TT}$ is a regionally dependent parameter, i.e. different rate constants are used for each region of the GI tract.
Fluid volume absorption/resorption:

$$\frac{dA}{dt} = k_{VA}[A] \quad \text{(Eq. 9)}$$

dA/dt=rate of absortpion, $k_{VA}$=rate constant, A=amount of fluid (water) in the compartment $$k_{VAZ} = k_{emp} \cdot Z_{VA} \quad \text{(Eq. 10)}$$

$Z_{VA}$=volume absorption adjustment parameter, $k_{emp}$ is determined emperically to match human fluid absorption in vivo.
Dissolution and Solubility:
Dissolution rate (regionally dependent)

$$\frac{d(A)}{dt} = k_D \cdot Z_D \cdot Mass \cdot (S_{ADJ} - C) \quad \text{(Eq. 11)}$$

A=Amount dissolved, $k_D$=User supplied dissolution rate constant, $Z_D$=Dissolution rate adjustment parameter, $S_{ADJ}$=solubility, C=concentration
Solubility (regionally dependent)

$$S_{ADJ} = \frac{(s_N - s_{n-1})}{(pH_n - pH_{n-1})}(pH - pH_{n-1}) + S_{n-1} \quad \text{(Eq. 12)}$$

$S_{ADJ}$=Solubility, $S_n$=user supplied solubility $\{S_1 \ldots S_5\}$, $pH_n$=user supplied pH values $\{pH_1 \ldots pH_5\}$ corresponding to user supplied solubilities, pH=pH value appropriate to region of the system such as GI tract. n is selected such that $pH_n$>pH, and $pH_{n-1}$<pH. If any of $pH_1 \ldots pH_5$ are equal to pH, the corresponding $S_n$ is used as the solubility.
Concentration (regionally dependent)

$$C = \frac{S_{ADJ}}{V} \quad \text{(Eq. 13)}$$

C=concentration of soluble drug, V=volume of fluid
Flux/Absorption:

$$J = P_{ADJ} \cdot SA_{ADJ} \cdot C \quad \text{(Eq. 14)}$$

J=flux, $P_{ADJ}$=Adjusted permeability, $SA_{ADJ}$=Adjusted surface area available for absorption, C=concentration $$P_{ADJ} = \left(\frac{2}{1+Z_{EFF}}\right) \cdot P_m \cdot Z_F \cdot 3600 + \frac{Z_{ACT} \cdot P_c \cdot 3600}{1 + \frac{C}{K_m}} \quad \text{(Eq. 15)}$$

$Z_{EFF}$=Efflux transport adjustment parameter, $P_m$=passive membrane permeability, $Z_F$=passive permeability or flux adjustment parameter, $Z_{ACT}$=active permeability adjustment parameter, $P_c$=active carrier permeability, C=concentration, $K_m$=Michaelis-Menton kinetic parameter.
Regional Permeability Correlation
Any regional permeability, $P_m$, can be calculated using any number of other provided permeabilities.

$$\ln P_a = C + A \cdot \ln\frac{1}{P_b} + B \cdot \ln\left(\frac{1}{P_b}\right)^2 \quad \text{(Eq. 16)}$$

$P_a$=permeability calculated using the regional correlation, $P_b$, permeability provided by the user, A, B, and C=constant coefficients fitted to determine correlation.

By way of example, rules utilized for a GI tract model of the PK tool and method of the intention include the following general processes.

2. General Processes For Rule Generation:
   1. GI transit. The transit of drug compound and fluid volume are somewhat controlled and the transit of formulations and/or controlled release devices is much more strictly controlled.
   2. Controlled Drug Release. The release of drug from the dosage form must be controlled such that drug is released into the correct intestinal region at the appropriate time.
   3. Dissolution. A comparison between the concentration and the solubility must be made to determine if additional insoluble compound will dissolve, or if compound already dissolved must precipitate to insoluble drug due to solubility limitations.
   4. Absorption. Mathematically, absorption may occur when physiologically it is impossible, e.g. when the volume in the colon becomes low enough that any dissolved drug will be within fluid contained in other solid waste also present in the colon and therefore unavailable for absorption. IF . . . THEN production rules control these situations.
   5. Permeability calculations. To estimate unprovided permeability values from provided permeability values logical evaluations must be made to determine the correct equations necessary to make the correlations.
   6. Concentration calculations. The concentration in the intestine cannot exceed the solubility for that particular region. If it does, an incorrect flux will be calculated. IF . . . THEN production rules are used to ensure the correct concentration is used in the flux calculation.
   7. Mathematical anomalies. At certain times during the simulation (especially early and late in the simulation) some compartments, flow regulators, or converters used in other calculations may have a value of 0 which will result in a computational error, e.g. division by 0. Production of rules are used to identify these situations and avoid the errors.

The following table lists the specific processes, conditions, results that control statement rules. e.g., IF . . . THEN production rules, are used to control. Generally, separate rules used for each region of the GI tract and are combined into one line in the table.

TABLE 15

Rules for Physiologic-Based GI track Simulation Model

| Process | Condition | Result in True | Result if False | Comments |
|---|---|---|---|---|
| GI Transit of drug compound or fluid volume | Time < 4 hours | No transit to waste | Transit to waste by first order process | Applies to GI regions using different values for the condition. |
| GI Transit of formulations or controlled release devices | Time cumulative physiol. transit time | no transit to next compartment | Immediate transit to next compartment | The rate constant for first order transit is set exceedingly large to provide near instantaneous transit. |
| Controlled release | Time to reach GI region < Time < Time to exit GI region | Drug is released from dosage form to GI region | No drug release into that GI region | Drug is released according to user provided release profile. |
| Dissolution | Soluble drug/volume (concentration) < Solubility | Drug moves from insoluble to soluble compartment according to dissolution rate | Drug moves from soluble to insoluble compartment according to precipitation rate | Precipitation rate is set to provide near instantaneous precipitation without causing "overshoot". |
| Absorption | Volume $<1 \times 10^{-6}$ ml AND Mass $< 1 \times 10^{-8}$ mg | No absorption, i.e. concentration = 0 | Absorption by flux equation | |
| Permeability Calculations | Duodenum, Jejunum, and Ileum Permeabilities all provided | Use provided Permeabilities | Estimate unprovided pemiabilities from provided permeabilities | 1 or 2 permeabilities can be used to calculate unprovided permeabilities |
| Concentration Calculation | Concentration < Solubility | Concentration used in flux equation | Solubility used in flux equation | |
| Mathematical anomalies | Volume = 0 | Dissolution rate = 0 | Dissolution rate calculated by Noyes-Whitney equation | Dissolution given as an example. Similar condications are provided for concentration calculations and other processes. |

Exemplary equations, rules, parameters and initial values for the graphical compartment-flow model and various sub-models of the integrated GI model illustrated in FIGS. 21–26 and 30–40 are provided in Appendix 4, as related to the abbreviation key provided as Appendix 3. Various aspects of the physiological, adjustment and regional correlation parameters employed in the GI model and their development are described in further detail below.

1. Physiological Parameters

Physiological parameters of the GI model included physiological ranges reported in the literature (Table 17) as well as specific values utilized in the model and compiled for each of five regions of the gastrointestinal tract (stomach, duodenum, jejunum, ileum and colon)(Table 16). These included values related to pH, transit time, surface area, and volume parameters.

TABLE 16

Physiological Parameters Employed In GI Model

| | pH[a] | Initial Volumes (ml) | Surface Area $(cm^2)$[b] | Average Transit time (hr)[c] | Volume Transfer Rates $(t_{90})(hr^{-1})$[c] | | New Water Absorpiton Rates* $(hr^{-1})$[d] |
|---|---|---|---|---|---|---|---|
| Stomach | 1.5 | 100 | NA | 0.5 | | 4.6 | 0 |
| Duodenum | 6.0 | 0 | 150 | 0.225 | | 10.8 | 0 |
| Jejunum | 6.5 | 0 | 1000 | 1.5 | | 1.54 | 1.75 |
| Ileum | 7.0 | 0 | 1000 | 1.5 | | 1.54 | 1.75 |

TABLE 16-continued

Physiological Parameters Employed In GI Model

| pH[a] | Initial Volumes (ml) | Surface Area (cm$^2$)[b] | Average Transit time (hr)[c] | Volume Transfer Rates ($t_{90}$)(hr$^{-1}$)[c] | New Water Absorpiton Rates* (hr$^1$)[d] |
|---|---|---|---|---|---|
| Colon | 6.5 | 0 | 850 | 24 | 0.094 | 0.1 |

*Water absorption rate parameters were set so that cumulative water absorption from each region using the GI model were in agreement with values listed in Table 17.
[a]Lui et al. J Pharm Sci 1986;75(3):271–4; Youngberg et al. Dig Dis Sci 1987;32(5):472–80; Charman et al. J Pharm Sci 1997;86(3):269–82; Langguth et al. Biopharm Drug Dispos 1994;15(9):719–46; Kararli TT. Biopharm Drug Dispos 1995;16(5):351–80;
[b]Wagner JG J Pharm Sci 1961;50(5):59–87; Ho NF, Park JY, Ni PF, et al. Crouthamel W, Sarapu AC, editors. Animal Models For Oral Drug Delivery In Man: In Situ And In Vivo Approaches. Washington, D. C. American Pharmaceutical Association, 1983; 2, Advancing quantitative and mechanistic approaches in interfacing gastrointestinal drug absorption studies in animals and humans. p. 27–106;
[c]Ho et al. Crouthamel W, Sarapu AC, editors. Animal Models For Oral Drug Delivery In Man: In Situ And In Vivo Approaches. Washing, D. C. American Pharmaceutical Association, 1983; 2, Advancing quantitative and mechanistic approaches in interfacing gastrointestinal drug absorpiton studies in animals and humans. p. 27–106; Oberle et al. Journal of Pharmacokinetics & Biopharmaceutics 1987;15:529–44: Davis SS. S T P Pharma 1986;22:1015–22; Davis et al. Gut 1986;27:886–92;
[d]Turnberg LA. Digestion (1973)9:357–81.

TABLE 17

Physiological Parameters Employed In GI Model

| pH[a] | Initial Volumes (ml) | Surface Area (cm$^2$)[b] | Average Transit time (hr)[c] | Volume Transfer Rates ($t_{90}$)(hr$^{-1}$)[c] | | New Water Absorption Rates (hr$^1$)[d] |
|---|---|---|---|---|---|---|
| Stomach | 1.0–2.5 | 100 | NA | 0.5–3.0 | 0.8–4.6 | 0 |
| Duodenum | 4.0–6.4 | 0 | 147–168 | 0.20–0.25 | 9.2–11.5 | 0 |
| Jejunum | 4.4–6.4 | 0 | 913.5–1044 | 1.0–2.0 | 1.15–2.3 | 4.0–4.5 |
| Ileum | 6.8–7.4 | 0 | 913.5–1044 | 1.2–1.5 | 1.54–1.9 | 2.4–2.7 |
| Colon | 5.5–7.0 | 0 | 763–872 | 18–36 | 0.064–0.13 | 1.4–1.6 |

[a]Lui et al. J Pharm Sci 1986;75(3):271–4; Youngberg et al. Dig Dis Sci 1987;32(5):472–80; Charman et al. J Pharm Sci 1997;86(3):269–82; Langguth et al. Biopharm Drug Dispos 1994;15(9) :719–46; Kararli TT. Biopharm Drug Dispos 1995;16(5):351–80;
[b]Wagner JG J Pharm Sci 1961;50(5):59–87; Ho NF, Park JY, Ni PF, et al. Crouthamel W, Sarapu AC, editors. Animal Models For Oral Drug Delivery In Man: In Situ And In Vivo Approaches. Washington, D. C. American Pharmaceutical Association, 1983; 2, Advancing quantitative and mechanistic approaches in interfacing gastrointestinal drug absorption studies in animals and humans. p. 27–106;
[c]Ho et al. Crouthamel W, Sarapu AC, editors. Animal Models For Oral Drug Delivery In Man: In Situ And In Vivo Approaches. Washing, D. C. American Pharmaceutical Association, 1983; 2, Advancing quantitative and mechanistic approaches in interfacing gastrointestinal drug absorpiton studies in animals and humans. p. 27–106; Oberle et al. Journal of Pharmacokinetics & Biopharmaceutics 1987;15:529–44: Davis SS. S T P Pharma 1986;22:1015–22; Davis et al. Gut 1986;27:886–92;
[d]Turnberg LA. Digestion (1973)9:357–81.

2. Adjustment Parameters

Differences between in vitro and in vivo conditions, as well as differences between in vivo conditions for one species of mammal and a second hamper accurate prediction of absorption using a simulation approach. For example, in vitro dissolution rate may or may not be comparable to dissolution rates existing in vivo, or, the permeability in rabbits may or may not be comparable to the permeability in humans.

To compensate for such differences, a set of selectively optimized adjustment parameters were developed. These parameters were designed to be utilized as constants that modify the underlying equations of specific compartments of the GI model to permit automatic correlation of input data to output data as well as facilitate accurate prediction of oral absorption for a diverse set of compounds. Listed below (Table 18) are examples of parameters that can be used to adjust parameters and equations as well as those which can be added or removed to a given model if necessary.

TABLE 18

Adjustment Parameters

| Compartment | Segment |
|---|---|
| Regional fluid absorption | stomach |
| | duodenum |
| | jejunum |
| | ileum |
| | colon |
| Flux/Permeability | duodenum |
| | jejunum |
| | ileum |
| | colon |
| Active/Carrier mediated Transport (absorption) | duodenum |
| | jejunum |
| | ileum |

TABLE 18-continued

Adjustment Parameters

| Compartment | Segment |
|---|---|
| | colon |
| Compound Efflux (secretion) | duodenum |
| | jejunum |
| | ileum |
| | colon |
| Transfer rates | stomach to duodenum |
| | duodenum to jejunum |
| | jejunum to ileum |
| | ileum to colon |
| | colon to waste |
| Surface Area | duodenum |
| | jejunum |
| | ileum |
| | colon |

The adjustment parameters were developed and optimized using a stepwise selective optimization process. Initial adjustment parameters were developed for correlation between humans and rabbit as follows. Two primary sets of data were used: 1) FDp and best fit plasma profiles from in vivo clinical pharmacokinetic (PK) data, and 2) simulated FDp and plasma profiles generated from the GI model. The FDp and best fit plasma profiles from in vivo PK data was obtained by analyzing and processing IV and PO data from humans for the test set of compounds described in Example 2 using a regression-based curve fitting algorithm to determine the best fit curve that matched the actual clinical plasma profiles. The second set of data was generated using a developmental GI model.

In vitro data (permeability, solubility, dissolution rate, and dose) were used as inputs into the GI model with the adjustment parameters set to some initial value previously determined to provide reasonably predictable values for FDp. The GI model was used to provide FDp data for each test compound. The FDp data generated from the GI model also was used as input data into an IV/PO PK model, such as the one shown in FIG. 19, to determine plasma profiles.

Figure 19:
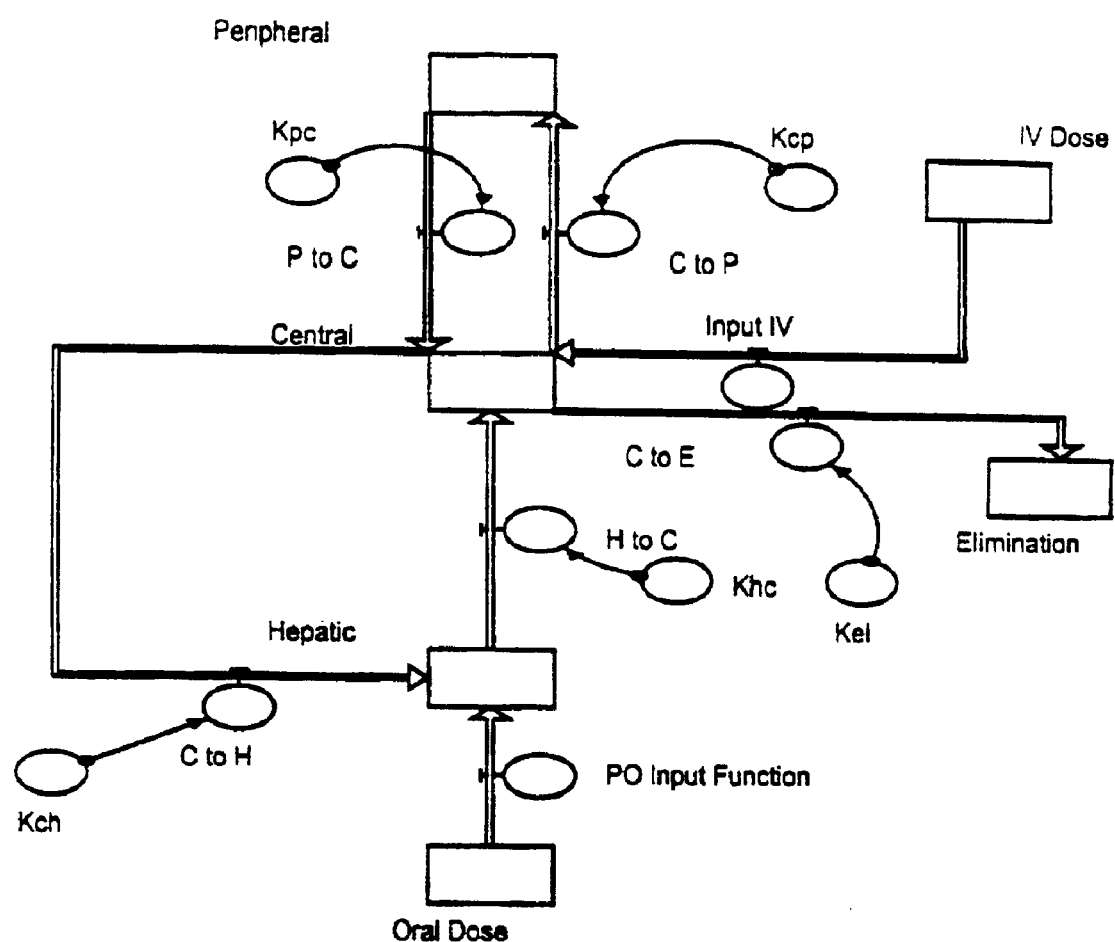
FIG. 19 shows graphical compartment-flow diagram illustrating the in vivo data analysis-processing IV/PO PK model (intravenous/oral administration) of the invention.
Figure 20:
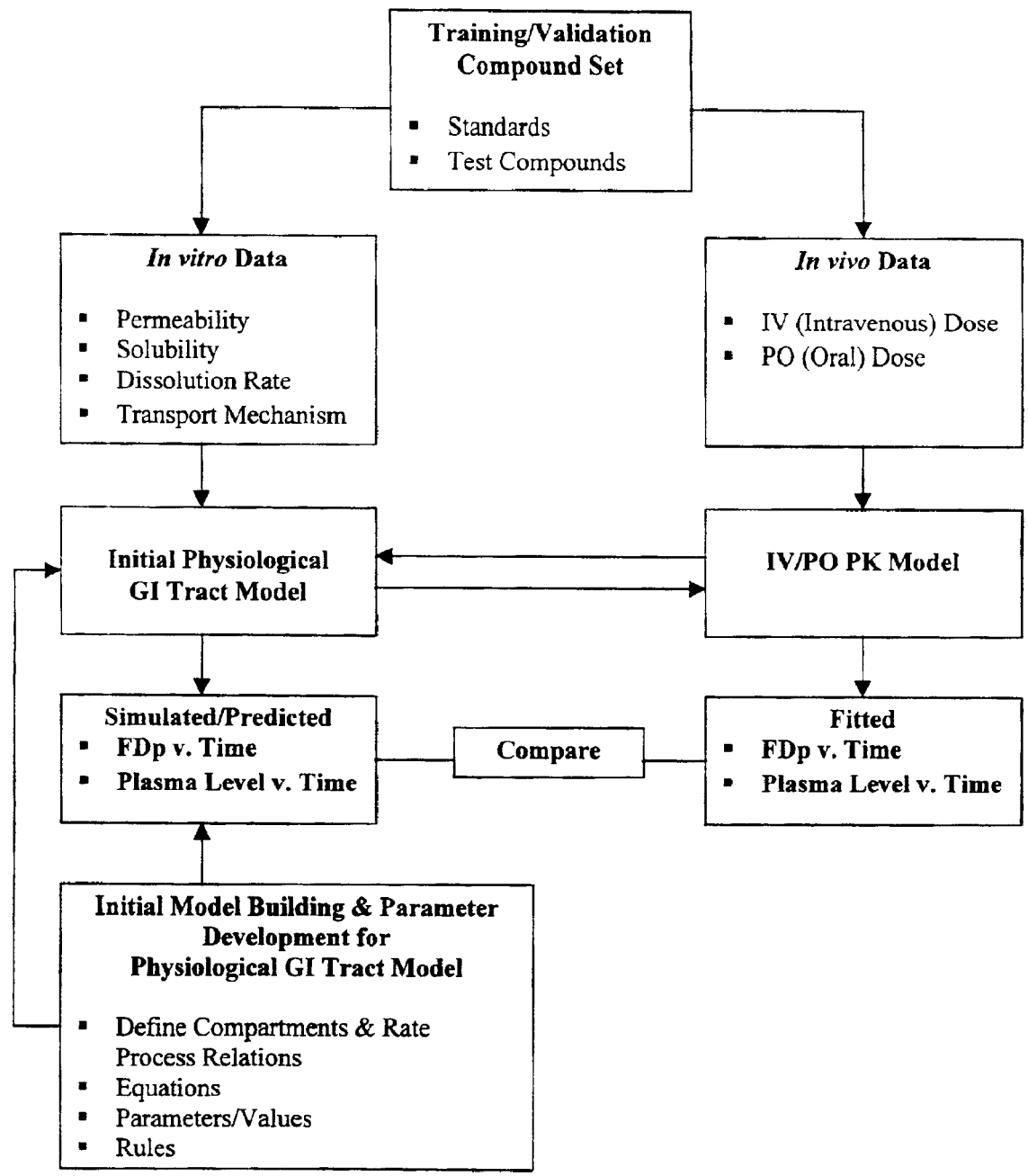
FIG. 20 shows schematic of method for development of initial integrated physiologic-based GI track simulation model of PK tool and method of the invention.

The PO input to the IV/PO PK model of FIG. 19 used for fitting clinical data is an error function and shown in Equation 17.

$$F = \frac{D \cdot FDp}{2} \left| 1 - erf \frac{1 - \frac{t}{t_{50}}}{\frac{2}{\frac{1}{P_e} \cdot \sqrt{\frac{t}{t_{50}}}}} \right| \quad (\text{Eq. 17})$$

Where D is the dose of drug delivered to the intestine, t is time in minutes, t50 is the time for 50% of the drug to be absorbed, and Pe is a parameter (Peclet number) related to the slope of the linear portion of the absorption curve.

When fitting the data, all available in vivo PK data (multiple intravenous (IV) dosing and multiple oral (PO) dosing) was analyzed simultaneously using the IV/PO PK model of FIG. 19. The data were weighted by 1/Standard Error of the Mean (SEM) or by 1/Concentration$^2$.

The initial adjustment parameter values were determined empirically. Using a limited set of compounds and corresponding in vitro data from rabbit tissue, the adjustment parameters were manually varied to obtain FDp values that were reasonably consistent with the actual PK data. After the initial values were determined, the GI model developed using STELLA® was converted to a program file readable by a program having fitting algorithm, such as KINETICA®. The initial adjustment parameters were then simultaneously fit using non-linear regression analysis in a stepwise manner to determine optimized values for the adjustment parameters. Within each step, a few parameters were selected for optimization by simultaneous fitting. The fitting was approached using an iterative process, where selected adjustment parameters were varied systematically such that the deviation of the GI model determined absorption from the actual PK determined absorption was minimized. Once the deviation was reduced to a satisfactory level, few more parameters were then selected and optimized. The process was continued until all parameters were successfully optimized. The new parameters were then placed into the GI model and the FDp determined for each compound which is compared to the PK FDp to establish the goodness of fit. This process was repeated until an acceptable goodness of fit was established. Using this approach, adjustment parameters were developed to correlate, for example, in vitro solubility, dissolution, dose and permeability in rabbits to in vivo human absorption. Although FDp was employed as the reference for deviation, the actual measurement of absorption can be evaluated using any number of parameters, such as plasma levels, absorption constants, or others. Moreover, it will be appreciated that many sets of adjustment parameters may be developed and established. For instance, others sets of adjustment parameters may be established to correlate dog, rat, monkey or other species permeability data to human, dog, rat, rabbit, monkey, or other animal in vivo absorption.

3. Regional Permeability Correlation Parameters

Since Pe in all intestinal regions may not be available, for instance when cell monolayer data is employed to determine Pe in colon, a correlation was developed that provides a reasonable prediction of unknown Pe values in the other intestinal regions.

An objective was to establish a correlation between regional permeabilities that allowed prediction of permeability in the duodenum, jejunum or ileum using known permeabilities in one or two of the other regions.

Correlation development involved obtention of regional permeability values in intestinal tissue from the literature and experimentally using methods consistent with the experimental protocols as described in Examples 4–5.

The regional correlation parameters are estimated using a polynomial equation developed for this purpose (Equation 17). Any regional permeability, $P_m$, can be calculated using any number of other provided permeabilities.

The regional correlation parameter function was incorporated into the GI model using a logic function module. A control statement was utilized to regulate activation of the regional correlation parameter estimation function when a user provides less than the total number of permeability values for the segments of the GI tract.

The following (Table 19) shows correlations that were established along with the corresponding correlation coefficient. Correlations were accomplished by data transformation and fitting to a non-linear function.

TABLE 19

Results of Regional Correlation

| Variable | | |
|---|---|---|
| Dependent | Independent | Correlation Coefficient |
| Duodenum | Jejunum | 0.870 |
| Duodenum | Ileum | 0.906 |
| Jejunum | Duodenum | 0.858 |
| Jejunum | Ileum | 0.914 |
| Ileum | Duodenum | 0.855 |
| Ileum | Jejunum | 0.894 |

As an example of the capability of the correlation, two of the above correlations were evaluated by estimating the permeability in the duodenum and jejunum using ileum Pe values. The compounds chosen were those for which complete Pe values were available.

The error and % error for the permeability calculations were determined by comparing predicted values to the known permeabilities (Table 20).

TABLE 20

Evaluation of Regional Correlations

| | Intestinal Region | | | |
|---|---|---|---|---|
| | Duodenum | | Jejunum | |
| Compound | Error | % Error | Error | % Error |
| Compound α1 | −4.64E-07 | −46.36 | 2.42E-07 | 35.03 |
| Compound α2 | 6.37E-08 | 5.79 | −1.11E-07 | −5.14 |
| Compound α3 | 3.10E-07 | 114.91 | −8.38E-07 | −45.28 |
| Compound α4 | 1.18E-05 | 196.00 | −5.40E-06 | −16.38 |

The above results demonstrate that the regional correlation parameter function of the GI model was able to accurately predict Pe values for compounds within the initial data set (i.e., high $r^2$).

Example 13

Validation and Testing of GI Model

To demonstrate that the physiological parameters of the model were operating in a logical manner consistent with expected behavior in vivo, the parameter were varied and the effect on output monitored. For example, a decrease in the surface area available for absorption should result in a decrease in the amount of compound absorbed. Thus, the physiological parameters of the model were varied by increasing and/or decreasing their values. The effect of these variations on the rate, as measured by T50 (time for 50% absorption), and extent, as measured by FDp, were simulated. Table 21 shows the physiological parameters that were varied and the expected effect on FDp and T50.

TABLE 21

Physiological Parameter Variations*

| Parameter | Range evaluated | Expected effect | |
|---|---|---|---|
| Surface Area or Permeability | 0.05 to 10 × Normal* $1 \times 10^{-7}$ to $1 \text{s} 10^{-5}$ cm/s | Increase in: Surface Area or Permeability | Increase FDp Decrease T50 |
| GI Transit | 0.05 to 10 × Normal* | Increase in: | Increase FDp |

TABLE 21-continued

Physiological Parameter Variations*

| Parameter | Range evaluated | Expected effect | |
|---|---|---|---|
| Time | | GI Transit Time | Increase T50 |
| Dissolution Rate | 0.05 to 10 × Normal* | Increase in: Dissolution Rate | Increase FDp Decreased T50 |
| Solubility | 1 to 100 mg/ml | Increase in: Solubility | Increase FDp Decrease T50 |

*Normal values used in the model are listed in Example 12. In each case, only the parameter chosen was varied, all other parameters were held constant.

All effects on FDp and T50 were as expected with the changes in the physiological parameters. While not all of the ranges were in the physiological range, the lower part of the range was included to assure that the model would limit to zero FDp as the various parameters approached zero.

To assess the basic power of the GI model for predicting oral drug absorption, the model was tested by simulating FDp as a function of time so as to separate absorption across intestinal tissue from first pass metabolism and drug concentration in systemic circulation. Accordingly, methods were developed and used to determine FDp from clinical plasma data so that transport across the intestinal tissue could be determined. This was accomplished by simultaneously fitting clinical pharmacokinetic data (PO and IV) to the two compartment open IV/PO PK model illustrated as a compartment-flow model in FIG. 19. Elimination was from the central compartment. Input from oral doses was into a pre-systemic compartment (for metabolism) which was in equilibrium with the central compartment. FDp was determined simultaneously for each oral dose. Clinical pharmacokinetic data fitted to the IV/PO PK model demonstrated the ability of the model to accurately determine blood levels in the central compartment.

The fitted clinical FDp data for a test set of compounds was then compared to FDp predicted by the GI model using both experimental in vitro values for permeability as input as well as estimated values calculated by the model using the regional permeability correlation function. The permeability source of the test compounds are shown in Table 22 below.

TABLE 22

Permeability Source of Test Compounds

| Compound | Permeability source* |
|---|---|
| α1 | Experimental |
| α2 | Experimental |
| α3 | Experimental |
| α4 | Experimental |
| α5 | Estimation |
| α6 | Experimental |
| α10 | Estimation |
| β1 | Estimation |
| β2 | Estimation |
| β3 | Estimation |
| β5 | Estimation |
| β6 | Estimation |

*Experimental - permeability values for all intestinal segments were submitted. Estimation permeability values were calculated using regional permeability correlation parameters.

FIGS. 49–53 are illustrative of the results of these tests. The physiological model was found to accurately predict FDp for the test set of compounds. The accuracy of the prediction is based on both rate and extent of absorption. Correlation of FDp extent between the clinical data and as predicted by the model for the test set of compounds yielded a collective regression coefficient ($r^2$) of greater than 0.92.

APPENDICIES

Appendix 1: Abbreviation Key for Mass-Volume Model

Abbreviation

Kf sd = associated rate constant for stomach and duodenum
Ka dj = associated rate constant for duodenum and jejunum
Ka ji = associated rate constant for jejunum and ileum
Ka ie = associated rate constant for ileum and colon
Ka co = associated rate constant for colon and excretion
SD trans = transfer rate between stomach and duodenum
DJ trans = transfer rate between duodenum and jejunum
JL trans = transfer rate between jejunum and ileum
IC trans = transfer rate between ileum and colon
Waste = transfer rate between colon and excretion
pH s = pH stomach
pH s2 = pH duodenum
pH s3 = pH jejunum
pH s4 = pH ileum
pH s5 = pH colon
sol profile = solubility profile for stomach
sol profile 2 = solubility profile for duodenum
sol profile 3 = solubility profile for jejunum
sol profile 4 = solubility profile for ileum APPENDICIES-continued Appendix 1: Abbreviation Key for Mass-Volume Model Abbreviation sol profile 5 = solubility profile for colon
stom ka = associated rate constant for stomach compartments 1 and 2
duo ka = associated rate constant for duodenum compartments 1 and 2
Jej ka = associated rate constant for jejunum compartments 1 and 2
Il ka = associated rate constant for ileum compartments 1 and 2
Colon ka = associated rate constant for colon compartments 1 and 2
SA stom = surface area of stomach
SA duo = surface area of duodenum
SA jej = surface area of jejunum
SA il = surface area of ileum
SA colon = surface area of colon
Perm stom = permeability of stomach
Perm duo = permeability of duodenum
Perm jej = permeability of jejunum
Perm il = permeability of ileum
Perm colon = permeability of colon
Ka sd = associated rate construct for stomach fluid absorption
Ka du = associated rate construct for duodeunm fluid absorption
Ka je = associated rate construct for jejunm fluid absorption
Ka il = associated rate construct for ileunm fluid absorption
Ka co = associated rate construct for colon fluid absorption Note:
other abbreviations adhere to above descriptors and are self explanatory Appendix 2: Equations, Parameters and Values For Mass-Volume Model amt_plasma(t) = amt_plasma(t −dt) + (trans_21 + ka −elimination −trans_12) * dt
INIT amt_plasma = 0
INFLOWS:
trans_21 = k21*comp_2
ka = tot_abs_rate
OUTFLOWS:
elimination = amt_plasma*k_elim
trans_12 = k12*amt_plasma
blood_side col(t) = blood_side col(t −dt) + (colon_ka_5) * dt
INIT blood_side_col = 0
INFLOWS:
colon_ka_5 IF Vol_colon*sol_profile_5 >=Colon THEN Colon*SA_colon*perm_colon*3600 ELSE Vol_colon*sol_profile_5*SA_colon*perm_colon*3600
blood_side dou(t) = blood_side_dou(t −dt) + (duo_ka) * dt
INIT blood_side_dou = 0
INFLOWS:
duo_ka = IF Vol_duod*sol_profile_2 >= duodenum THEN duodenum*SA_duo*perm_duo*3600 ELSE Vol_duod*sol_profile_2*SA_duo*perm_duo*3600
blood_side il(t) = blood_side il(t −dt) + (Il_ka) * dt
INIT blood_side_il = 0
INFLOWS:
Il_ka = IF Vol_ileum*sol_profile_4 >=Ileum THEN Ileum*SA_Il*perm_Il*3600 ELSE Vol_ileum*sol_profile_4*SA_Il*perm_Il*3600
blood_side_jej(t) = blood_side_jej(t −dt) + (Jej_ka) * dt
INIT blood_side_jej = 0
iNFLOWS:
Jej_ka = IF Vol_jej*sol_profile_3 >=Jejunum THEN Jejunum*SA_jej*perm_jej *3600 ELSE Vol_jej*sol_profile_3*SA_jej*perm_jej*3600

-continued

Appendix 2: Equations, Parameters and Values For Mass-Volume Model blood_side sto(t) = blood_side_sto(t −dt) + (stom_ka) * dt
INIT blood_side_sto = 0
INFLOWS:
stom_ka = IF Vol_stom*sol_profile >= Stomach THEN Stomach*SA_stom*perm_stom*3600
ELSE Vol_stom*sol_profile*SA_stom*perm_stom*3600
Colon(t) = Colon(t −di) + (IC_trans −Waste −colon_ka_5) * dt
INIT Colon = 0
INFLOWS:
IC_trans= ka_ic*Ileum
OUTFLOWS:
Waste = ka_col*Colon
colon_ka_5 = IF Vol_colon*sol_profile_5 >=Colon THEN Colon*SA_colon*perm_colon*3600
ELSE Vol_colon*sol_profile_5*SA_colon*perm_colon* 3600
comp_2(t) = comp_2(t −dt) + (trans_12 −trans_21) * dt
INITcomp_2:= 0
INFLOWS:
trans_12 = k12*amt_plasma
OUTFLOWS:
trans_21 = k21*comp_2
duodenum(t) = duodenum(t −dt) + (SD_trans −duo_ka−DJ_trans) * dt
INIT duodenum = 0
INFLOWS:
SD_trans = if Stomach >0 then kf_sd*Stomach else 0
OUTFLOWS:
duo_ka   =   IF   Vol_duod*sol_profile_2   >=   duodenum   THEN
duodenum*SA_duo*perm_duo*3600 ELSE Vol_duod*sol_profile_2*SA_duo*perm_duo*3600
DJ_trans = ka_dj*duodenum
excretion(t) = excretion(t −dt) + (vol_cw) * dt
INIT excretion = 0
INFLOWS:
vol_cw = Vol_colon*ka_col
excretion_2(t) = excretion_2(t −dt) + (Waste) * dt
INIT excretion_2 = 0
INFLOWS:
Waste =ka_col*Colon
Ileum(t) = Ileum(t −dt) + (JL_trans −IC_trans −Il_ka) * dt
INIT Ileum = 0
INFLOWS:
JL_trans = ka_ji*Jejunum
OUTFLOWS:
IC_trans = ka_ic*Ileum
Il_ka = IF Vol_ileum*sol_profile_4 >=Ileum THEN Ileum*SA_Il*perm_Il*3600   ELSE
Vol_ileum*sol_profile_4*SA_Il*perm_Il*3600
Jejunum(t) = Jejunum(t −dt) + (DJ_trans −JL_trans −Jej_ka) * dt
INIT Jejunum = 0
INFLOWS:
DJ_trans = ka_dj*duodenum
OUTFLOWS:
JL_trans = ka_ji*Jejunum
Jej_ka = IF Vol_jej*sol_profile_3 >=Jejunum THEN Jejunum*SA_jej*perm_jej *3600 ELSE
Vol_jej*sol_profile_3*SA_jej*perm_jej*3600
serosal_col(t) = serosal_col(t −dt) + (Adsorp_col −col_secretion) * dt
INIT serosal_col = 0
INFLOWS:
Adsorpcol_col = PULSE(1.67,0,.1)+0*Vol_colon*ka_co
OUTFLOWS:
col_secretion = 0
serosal_dou(t) = serosal_dou(t −dt) + (Adsorp_Duo −duo_secretion) * dt
INIT serosal_dou = 0
INFLOWS:
Adsorp_Duo = PULSE(10.82,0,.1)+0*Vol_duod*ka_du
OUTFLOWS:
duo_secretion = PULSE(10.82,0,.1)
serosal_ill(t) = serosal_ill(t −dt) + (Adsorpt_ill −ile_secretion) * dt
INIT serosal_ill = 0
INFLOWS:
Adsorpt_ill = PULSE(8.83,0,.10)+0*Vol_ileum*ka_il
OUTFLOWS:
ile_secretion = PULSE(1.50,0,.1)
serosal_jej(t) = serosal_jej(t −dt) + (Adsorp_jej −jej_secretion) * dt
INIT serosal_jej = 0
INFLOWS:
Adsorp_jej = PULSE(15.76,0,.1)+0*Vol_jej*ka_je
OUTFLOWS:
jej_secretion = PULSE(2.67,0,.1)
serosal_sto(t) = serosal_sto(t −dt) + (Adsorp_Stom −Stom_Secretion) * dt
INIT serosal_sto = 0

Appendix 2: Equations, Parameters and Values For Mass-Volume Model

INFLOWS:
Adsorp_Stom = 0*Vol_stom*ka_sd
OUTFLOWS:
Stom_Secretion = PULSE(16.67,0,.1)
Stomach(t) = Stomach(t −dt) + (−SD_trans −stom_ka) * dt
INIT Stomach = 1000
OUTFLOWS:
SD_trans if Stomach >0 then kf_sd*Stomach else 0
stom_ka = IF Vol_stom*sol_profile >= Stomach THEN Stomach*SA_stom*perm_stom*3600
ELSE Vol_stom*sol_profile*SA_stom*perm_stom*3600
total_drug_absorbed(t) = total_drug_absorbed(t −dt) + (tot_abs_rate) * dt
INIT total_drug_absorbed = 0
INFLOWS:
tot_abs_rate = stom_ka+duo_ka+Jej_ka+Il_ka+colon_ka_5
Total_Elimination(t) = Total Elimination(t −dt) + (elimination) * dt
INIT Total_Elimination = 0
INFLOWS:
elimination = amt_plasma*k_elim
Vol_colon(t) = Vol_colon(t −dt) + (vol_ij + col_secretion −vol_cw −Adsorp_col) * dt
INIT Vol_colon = 0
INFLOWS:
vol_ij = Vol_ileum*ka_ic
col_secretion = 0
OUTFLOWS:
vol_cw = Vol_colon*ka_col
Adsorpcol_col = PULSE(1.67,0,.1)+0*Vol_colon*ka_co
Vol_duod(t) = Vol_duod(t −dt) + (vol_sd + duo_secretion −voil_dj −Adsorp_Duo) * dt
INIT Vol_duod = 0
INFLOWS:
vol_sd = kf_sd*Vol_stom
duo_secretion = PULSE(10.82,0,.1)
OUTFLOWS:
voil_dj = Vol_duod*ka_dj
Adsorp_Duo = PULSE(10.82,0,.1)+0*Vol_duod*ka_du
Vol_ileum(t) = Vol_ileum(t −dt) + (vol_ji + ile_secretion −Adsorpt_ill −vol_ij) * dt
INIT Vol_ileum = 0
INFLOWS:
vol_ji = Vol_jej*ka_ji
ile_secretion = PULSE(1.50,0,.1)
OUTFLOWS:
Adsorpt_ill = PULSE(8.83,0,.10)+0*Vol_ileum*ka_il
vol_ij = Vol_ileum*ka_ic
Vol_jej(t) = Vol_jej(t −dt) + (voil_dj + jej_secretion −vol_ji −Adsorp_jej) * dt
INIT Vol_jej = 0
rNFLOWS:
voil_dj = Vol_duod*ka_dj
jej_secretion = PULSE(2.67,0,.1)
OUTFLOWS:
vol_ji = Vol_jej*ka_ji
Adsorp_jej = PULSE(15.76,0,.1)+0* Vol_jej *ka_je
Vol_stom(t) = Vol_stom(t −dt) + (Stom_Secretion −vol_sd −Adsorp_Stom) * dt
INIT Vol_stom = PULSE(8.33,0,.1)
INFLOWS:
Stom_Secretion = PULSE(16.67,0,.1)
OUTFLOWS:
vol_sd = kf_sd*Vol_stom
Adsorp_Stom = 0* Vol_stom*ka_sd
conc_plasma = (amt_plasma/volume)*mg_to_ug
k12 = .839
k21 = .67
ka_co = 1
ka_col = 3
ka_dj = 3
ka_du = 1
ka_ic = 3
ka_il = 8.83
ka_je = 1
ka_ji = 3
ka_sd = 1
kf_sd = 2.8
k_elim = .161
mg_to_ug = 1000
perm _colon = 3.80e-6
perm_duo = 1.10e-6
perm_Il = 4.06e-6
perm_jej = 2.17e-6
perm_stom = 1.10e-6

-continued

| Appendix 2: Equations, Parameters and Values For Mass-Volume Model |
|---| ph_s = 1.5
ph_s_2 = 6.6
ph_s_3 = 6.6
ph_s_4 = 7.5
ph_s_5 = 6.6
SA_colon = 138
SA_duo = 125
SA_Il = 102
SA_jej = 182
SA_stom = 50
volume = 4*19200
sol_profile = GRAPH(ph_s)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_2 = GRAPH(ph_s_2)
(1.00, 63.0), (1.50, 25.0), (2.00, 10.0), (2.50, 5.00), (3.00. 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_3 = GRAPH(ph_s_3)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_4 = GRAPH(ph_s_4)
(1.00, 63.0), (1.50, 25.0), (2.00, 10.0), (2.50, 5.00), (3.00, 4.00), (3.50, 3.80), (4.00, 3.65), (4.50. 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_5 = GRAPH(ph_s_5)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)

APPENDICIES

Appendix 1: Abbreviation Key for Mass-Volume Model

| Abbreviation |
|---|
| Kf sd = associated rate constant for stomach and duodenum |
| Ka dj = associated rate constant for duodenum and jejunum |
| Ka ji = associated rate constant for jejunum and ileum |
| Ka ie = associated rate constant for ileum and colon |
| Ka co = associated rate constant for colon and excretion |
| SD trans = transfer rate between stomach and duodenum |
| DJ trans = transfer rate between duodenum and jejunum |
| JL trans = transfer rate between jejunum and ileum |
| IC trans = transfer rate between ileum and colon |
| Waste = transfer rate between colon and excretion |
| pH s = pH stomach |
| pH s2 = pH duodenum |
| pH s3 = pH jejunum |
| pH s4 = pH ileum |
| pH s5 = pH colon |
| sol profile = solubility profile for stomach |

| |
|---|
| sol profile 2 = solubility profile for duodenum |
| sol profile 3 = solubility profile for jejunum |
| sol profile 4 = solubility profile for ileum |
| sol profile 5 = solubility profile for colon |
| stom ka = associated rate constant for stomach compartments 1 and 2 |
| duo ka = associated rate constant for duodenum compartments 1 and 2 |
| Jej ka = associated rate constant for jejunum compartments 1 and 2 |
| Il ka = associated rate constant for ileum compartments 1 and 2 |
| Colon ka = associated rate constant for colon compartments 1 and 2 |
| SA stom = surface area of stomach |
| SA duo = surface area of duodenum |
| SA jej = surface area of jejunum |
| SA il = surface area of ileum |
| SA colon = surface area of colon |
| Perm stom = permeability of stomach |
| Perm duo = permeability of duodenum |
| Perm jej = permeability of jejunum |
| Perm il = permeability of ileum |
| Perm colon = permeability of colon |

| |
|---|
| Ka sd = associated rate construct for stomach fluid absorption |
| Ka du = associated rate construct for duodeunm fluid absorption |
| Ka je = associated rate construct for jejunm fluid absorption |
| Ka il = associated rate construct for ileunm fluid absorption |
| Ka co = associated rate construct for colon fluid absorption |
| Note: other abbreviations adhere to above descriptors and are self explanatory |

Appendix 2: Equations, Parameters and Values For Mass-Volume Model amt_plasma(t) = amt_plasma(t - dt) + (trans_21 + ka - elimination - trans_12) * dt
INIT amt_plasma = 0

INFLOWS:
trans_21 = k21*comp_2
ka = tot_abs_rate

OUTFLOWS:
elimination = amt_plasma*k_elim
trans_12 = k12*amt_plasma
blood_side_col(t) = blood_side_col(t - dt) + (colon_ka_5) * dt
INIT blood_side_col = 0

INFLOWS:
colon_ka_5 = IF Vol_colon*sol_profile_5 >=Colon THEN Colon*SA_colon*perm_colon*3600
ELSE Vol_colon*sol_profile_5*SA_colon*perm_colon*3600
blood_side_dou(t) = blood_side_dou(t - dt) + (duo_ka) * dt
INIT blood_side_dou = 0

INFLOWS:
duo_ka = IF Vol_duod*sol_profile_2 >= duodenum THEN duodenum*SA_duo*perm_duo*3600 ELSE Vol_duod*sol_profile_2*SA_duo*perm_duo*3600
blood_side_il(t) = blood_side_il(t - dt) + (Il_ka) * dt
INIT blood_side_il = 0

INFLOWS:
Il_ka = IF Vol_ileum*sol_profile_4 >=Ileum THEN Ileum*SA_Il*perm_Il*3600 ELSE Vol_ileum*sol_profile_4*SA_Il*perm_Il*3600
blood_side_jej(t) = blood_side_jej(t - dt) + (Jej_ka) * dt
INIT blood_side_jej = 0

INFLOWS:
Jej_ka = IF Vol_jej*sol_profile_3 >=Jejunum THEN Jejunum*SA_jej*perm_jej *3600 ELSE Vol_jej*sol_profile_3*SA_jej*perm_jej*3600
blood_side_sto(t) = blood_side_sto(t - dt) + (stom_ka) * dt
INIT blood_side_sto = 0

INFLOWS:
stom_ka = IF Vol_stom*sol_profile >= Stomach THEN Stomach*SA_stom*perm_stom*3600
ELSE Vol_stom*sol_profile*SA_stom*perm_stom*3600
Colon(t) = Colon(t - dt) + (IC_trans - Waste - colon_ka_5) * dt
INIT Colon = 0

100.

INFLOWS:
IC_trans = ka_ic*Ileum

OUTFLOWS:
Waste = ka_col*Colon
colon_ka_5 = IF Vol_colon*sol_profile_5 >=Colon THEN Colon*SA_colon*perm_colon*3600 ELSE Vol_colon*sol_profile_5*SA_colon*perm_colon*3600
comp_2(t) = comp_2(t - dt) + (trans_12 - trans_21) * dt
INIT comp_2 = 0

INFLOWS:
trans_12 = k12*amt_plasma

OUTFLOWS:
trans_21 = k21*comp_2
duodenum(t) = duodenum(t - dt) + (SD_trans - duo_ka - DJ_trans) * dt
INIT duodenum = 0

INFLOWS:
SD_trans = if Stomach >0 then kf_sd*Stomach else 0

OUTFLOWS:
duo_ka = IF Vol_duod*sol_profile_2 >= duodenum THEN duodenum*SA_duo*perm_duo*3600 ELSE Vol_duod*sol_profile_2*SA_duo*perm_duo*3600
DJ_trans = ka_dj*duodenum
excretion(t) = excretion(t - dt) + (vol_cw) * dt
INIT excretion = 0

INFLOWS:
vol_cw = Vol_colon*ka_col
excretion_2(t) = excretion_2(t - dt) + (Waste) * dt
INIT excretion_2 = 0

INFLOWS:
Waste = ka_col*Colon
Ileum(t) = Ileum(t - dt) + (JL_trans - IC_trans - Il_ka) * dt
INIT Ileum = 0

INFLOWS:
JL_trans = ka_ji*Jejunum

OUTFLOWS:
IC_trans = ka_ic*Ileum
Il_ka = IF Vol_ileum*sol_profile_4 >=Ileum THEN Ileum*SA_Il*perm_Il*3600 ELSE Vol_ileum*sol_profile_4*SA_Il*perm_Il*3600
Jejunum(t) = Jejunum(t - dt) + (DJ_trans - JL_trans - Jej_ka) * dt

101.

INIT Jejunum = 0

INFLOWS:
DJ_trans = ka_dj*duodenum

OUTFLOWS:
JL_trans = ka_ji*Jejunum
Jej_ka = IF Vol_jej*sol_profile_3 >=Jejunum THEN Jejunum*SA_jej*perm_jej *3600 ELSE Vol_jej*sol_profile_3*SA_jej*perm_jej*3600
serosal_col(t) = serosal_col(t - dt) + (Adsorp_col - col_secretion) * dt
INIT serosal_col = 0

INFLOWS:
Adsorp_col = PULSE(1.67,0,.1)+0*Vol_colon*ka_co

OUTFLOWS:
col_secretion = 0
serosal_dou(t) = serosal_dou(t - dt) + (Adsorp_Duo - duo_secretion) * dt
INIT serosal_dou = 0

INFLOWS:
Adsorp_Duo = PULSE(10.82,0,.1)+0*Vol_duod*ka_du

OUTFLOWS:
duo_secretion = PULSE(10.82,0,.1)
serosal_ill(t) = serosal_ill(t - dt) + (Adsorpt_ill - ile_secretion) * dt
INIT serosal_ill = 0

INFLOWS:
Adsorpt_ill = PULSE(8.83,0,.10)+0*Vol_ileum*ka_il

OUTFLOWS:
ile_secretion = PULSE(1.50,0,.1)
serosal_jej(t) = serosal_jej(t - dt) + (Adsorp_jej - jej_secretion) * dt
INIT serosal_jej = 0

INFLOWS:
Adsorp_jej = PULSE(15.76,0,.1)+0*Vol_jej*ka_je

OUTFLOWS:
jej_secretion = PULSE(2.67,0,.1)
serosal_sto(t) = serosal_sto(t - dt) + (Adsorp_Stom - Stom_Secretion) * dt
INIT serosal_sto = 0

INFLOWS:
Adsorp_Stom = 0*Vol_stom*ka_sd

102.

OUTFLOWS:
Stom_Secretion = PULSE(16.67,0,.1)
Stomach(t) = Stomach(t - dt) + (- SD_trans - stom_ka) * dt
INIT Stomach = 1000

OUTFLOWS:
SD_trans = if Stomach >0 then kf_sd*Stomach else 0
stom_ka = IF Vol_stom*sol_profile >= Stomach THEN Stomach*SA_stom*perm_stom*3600
ELSE Vol_stom*sol_profile*SA_stom*perm_stom*3600
total_drug_absorbed(t) = total_drug_absorbed(t - dt) + (tot_abs_rate) * dt
INIT total_drug_absorbed = 0

INFLOWS:
tot_abs_rate = stom_ka+duo_ka+Jej_ka+Il_ka+colon_ka_5
Total_Elimination(t) = Total_Elimination(t - dt) + (elimination) * dt
INIT Total_Elimination = 0

INFLOWS:
elimination = amt_plasma*k_elim
Vol_colon(t) = Vol_colon(t - dt) + (vol_ij + col_secretion - vol_cw - Adsorp_col) * dt
INIT Vol_colon = 0

INFLOWS:
vol_ij = Vol_ileum*ka_ic
col_secretion = 0

OUTFLOWS:
vol_cw = Vol_colon*ka_col
Adsorp_col = PULSE(1.67,0,.1)+0*Vol_colon*ka_co
Vol_duod(t) = Vol_duod(t - dt) + (vol_sd + duo_secretion - voil_dj - Adsorp_Duo) * dt
INIT Vol_duod = 0

INFLOWS:
vol_sd = kf_sd*Vol_stom
duo_secretion = PULSE(10.82,0,.1)

OUTFLOWS:
voil_dj = Vol_duod*ka_dj
Adsorp_Duo = PULSE(10.82,0,.1)+0*Vol_duod*ka_du
Vol_ileum(t) = Vol_ileum(t - dt) + (vol_ji + ile_secretion - Adsorpt_ill - vol_ij) * dt
INIT Vol_ileum = 0

INFLOWS:
vol_ji = Vol_jej*ka_ji
ile_secretion = PULSE(1.50,0,.1)

OUTFLOWS:
Adsorpt_ill = PULSE(8.83,0,.10)+0*Vol_ileum*ka_il
vol_ij = Vol_ileum*ka_ic
Vol_jej(t) = Vol_jej(t - dt) + (voil_dj + jej_secretion - vol_ji - Adsorp_jej) * dt
INIT Vol_jej = 0

INFLOWS:
voil_dj = Vol_duod*ka_dj
jej_secretion = PULSE(2.67,0,.1)

OUTFLOWS:
vol_ji = Vol_jej*ka_ji
Adsorp_jej = PULSE(15.76,0,.1)+0*Vol_jej*ka_je
Vol_stom(t) = Vol_stom(t - dt) + (Stom_Secretion - vol_sd - Adsorp_Stom) * dt
INIT Vol_stom = PULSE(8.33,0,.1)

INFLOWS:
Stom_Secretion = PULSE(16.67,0,.1)

OUTFLOWS:
vol_sd = kf_sd*Vol_stom
Adsorp_Stom = 0*Vol_stom*ka_sd
conc_plasma = (amt_plasma/volume)*mg_to_ug
k12 = .839
k21 = .67
ka_co = 1
ka_col = 3
ka_dj = 3
ka_du = 1
ka_ic = 3
ka_il = 8.83
ka_je = 1
ka_ji = 3
ka_sd = 1
kf_sd = 2.8
k_elim = .161
mg_to_ug = 1000
perm_colon = 3.80e-6
perm_duo = 1.10e-6
perm_Il = 4.06e-6
perm_jej = 2.17e-6
perm_stom = 1.10e-6
ph_s = 1.5
ph_s_2 = 6.6
ph_s_3 = 6.6 ph_s_4 = 7.5
ph_s_5 = 6.6
SA_colon = 138
SA_duo = 125
SA_Il = 102
SA_jej = 182
SA_stom = 50
volume = 4*19200
sol_profile = GRAPH(ph_s)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_2 = GRAPH(ph_s_2)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_3 = GRAPH(ph_s_3)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_4 = GRAPH(ph_s_4)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)
sol_profile_5 = GRAPH(ph_s_5)
(1.00, 63.0), (1.50, 25.0), (2.00, 10.0), (2.50, 5.00), (3.00, 4.00), (3.50, 3.80), (4.00, 3.65), (4.50, 3.50), (5.00, 3.65), (5.50, 3.65), (6.00, 3.65), (6.50, 3.65), (7.00, 3.65), (7.50, 3.65), (8.00, 3.65), (8.50, 4.00), (9.00, 5.00), (9.50, 12.0), (10.0, 23.5)

105.

Appendix 3: Abbreviation Key For GI Model

The legend/key has been divided into sub-sections corresponding to the sub-sections of the model diagram.

Numbered suffixes (1, 2, 3, 4, 5, 6) have been assigned to distinguish between intestinal regions (stomach, duodenum, jejunum, ileum, colon, and waste, respectively).

1 – stomach
2 – duodenum
3 – jejunum
4 – ileum
5 – colon
6 – waste

For example, VOL 1 is the volume in the stomach, MASS 3 is the insoluble mass in the jejunum. In the equations, COMP 1 indicates the stomach, COMP 2 the duodenum, COMP 3, the jejunum, etc.

Ghosts are listed under the sub-section containing the original reservoir, flow regulator, or converter.

Abbreviations listed in italics are regionally dependent and set up as arrays to allow independent values for each intestinal region.

In general, ADJ as a prefix indicates a calculated parameter value (ADJ = adjusted), while ADJ as a suffix indicates an adjustment parameter (ADJ = adjustment).

Intestinal model

Reservoirs/Compartments

| | |
|---|---|
| VOL ABS | Fluid volume absorbed |
| VOL | Fluid volume |
| C REL | Mass of drug contained with a formulation or controlled release device |
| MASS | Insoluble mass of drug (not contained within the formulation or controlled release device) |
| SOL | Soluble mass of drug |
| ABSORPTION | Mass of drug absorbed |

Flow regulators

| | |
|---|---|
| REABS | Rate of water absorption |
| VOL OUT | Fluid volume transit rate |
| CR OUT | Formulation or controlled release device transit rate |
| CR INPUT | Drug release rate from formulation or controlled release device |
| MASS OUT | Insoluble drug mass transit rate |
| DISS PRECIP | Dissolution rate |
| SOL OUT | Soluble drug mass transit rate |
| FLUX | Absorption rate |

ADJ PARMS (Adjustment Parameters)

| | |
|---|---|
| VOL ADJ | Fluid volume absorption adjustment parameter |
| DISS ADJ | Dissolution rate adjustment parameter |
| TRANSIT ADJ | Transit time adjustment parameter |
| SA ADJ | Surface area adjustment parameter |
| FLUX ADJ | Passive Absorption adjustment parameter |
| EFFLUX ADJ | Efflux or secretion adjustment parameter |
| CARRIER ADJ | Active absorption adjustment parameter |

PARMS (Parameters)

| | |
|---|---|
| VOL PARM | Fluid volume absorption rate constant |
| SURFACE AREA | Surface area available for absorption |
| DOSE | The administered dose of drug |
| INIT VOLUME | The administered volume of water or fluid |
| TIME IN HOURS | A clock |
| pH | The physiological pH value |
| PARACELLULAR | A user controlled switch used to adjust absorption based on absorption mechanism |

TRANSIT TIME

| | |
|---|---|
| TRANSFERS | GI transit rate constant |
| CUMU TT | Cumulative transit time |
| ADJ TRANSIT TIME | Adjusted GI transit time incorporating adjustment parameter and user input |
| USER TT INPUT | User controlled adjustments to the GI transit time |

OUTPUT CALCULATIONS

| | |
|---|---|
| ABSORBED TOTAL | Total mass of drug absorbed (sum of ABSORPTION 1...5) |

107.

| | |
|---|---|
| FDp% | Fraction or the dose absorbed into portal vein x 100 |
| FLUX TOTAL | Total absorption rate (sum of FLUX 1...5) |
| CUM DISS | Cumulative drug mass dissolved |
| CR Release | Cumulative drug mass released from formulation |
| CUM DISS RATE | Sum of DISS PRECIP 1...5 |
| CR cumrate | Summ of CR INPUT 1...5 |

PERMEABILITY CALCULATION

| | |
|---|---|
| ADJ PERM | Adjusted permeability ncorporating all transport mechanisms and relevant adjustment parameters |
| ACT PE | Active or carrier-mediated absorptive permeability |
| Km | Constant from the Michaelis-Mentin type permeability equation for active transport |
| REGIONAL | Passive permeability after regional correlation calculation (same as PASS PE if regional correlation is not used) |
| PASS PE | Passive permeability entered by user |
| RC | A logical function used in determining the regional correlation |
| RCSUM | A logical function used in determining the regional correlation |

SOLUBILITY CALCULATION

| | |
|---|---|
| USER pH | User supplied pH value for which a solubility value is available |
| USER SOLUB | User supplied solubility value corresponding to the USER pH value |
| ADJ SOLUB | Solubility calculated (if necessary) at the appropriate pH value using the entered USER pH and USER SOLUB values |

CONTROLLED RELEASE CALCULATION

| | |
|---|---|
| CR RATE | The instantaneous release rate from the formulation |
| CR DOSE | The total dose contained with the formulation |
| CR AT TIME | The cumulative drug mass release profile |
| CR AT LAST | The cumulative drug mass release profile |

Note: CR AT TIME holds the value at the current time value (t), CR AT LAST holds the value at the immediately preceeding time value (t-1)

CONC CALCULATION

| | |
|---|---|
| CONCENTRATIONS | The dissolved drug concentration |

DISSOLUTION CALCULATION

PRECIP				Precipitation rate constant
DISSOL				Dissolution rate constant
ADJ DISS PRECIP			Adjusted rate constant incorporating PRECIP, DISSOL and calculated concentration

Appendix 4: Equations, Parameters and Values For GI Model

- ADJ PARMS
  - CARRIER_ADJ[COMPS] = 0
  - DISS_ADJ[COMP_1] = 1
  - DISS_ADJ[COMP_2] = 1
  - DISS_ADJ[COMP_3] = 1
  - DISS_ADJ[COMP_4] = 1
  - DISS_ADJ[COMP_5] = 1
  - EFFLUX_ADJ[COMPS] = 1
  - FLUX_ADJ[COMP_1] = 1
  - FLUX_ADJ[COMP_2] = 10
  - FLUX_ADJ[COMP_3] = 8
  - FLUX_ADJ[COMP_4] = 2
  - FLUX_ADJ[COMP_5] = 1
  - SA_ADJ[COMP_1] = 1
  - SA_ADJ[COMP_2] = 1
  - SA_ADJ[COMP_3] = 1
  - SA_ADJ[COMP_4] = 1
  - SA_ADJ[COMP_5] = 1
  - TRANSIT_ADJ[COMP_1] = 1
  - TRANSIT_ADJ[COMP_2] = 1
  - TRANSIT_ADJ[COMP_3] = 1
  - TRANSIT_ADJ[COMP_4] = 1
  - TRANSIT_ADJ[COMP_5] = 1
  - VOL_ADJ[COMP_1] = 1
  - VOL_ADJ[COMP_2] = 1
  - VOL_ADJ[COMP_3] = 1
  - VOL_ADJ[COMP_4] = 1
  - VOL_ADJ[COMP_5] = 1
- CONC CALCULATION
  - CONCENTRATIONS[COMP_1] = if VOL_1=0.0 then 0 else if ADJ_SOLUB[COMP_1]<SOL_1/VOL_1 then ADJ_SOLUB[COMP_1] else SOL_1/VOL_1 + 0*(SOL_2+SOL_5+SOL_3+SOL_4+VOL_3+VOL_2+VOL_4+VOL_5)
  - CONCENTRATIONS[COMP_2] = if VOL_2 = 0.0 then 0 else if (VOL_2<1e-6 AND SOL_2<1e-7) then 0 else if ADJ_SOLUB[COMP_2]<SOL_2/VOL_2 then ADJ_SOLUB[COMP_2] else SOL_2/VOL_2
    +0*(SOL_1+SOL_5+SOL_3+SOL_4+VOL_3+VOL_1+VOL_5+VOL_4)
  - CONCENTRATIONS[COMP_3] = if VOL_3 = 0.0 then 0 else if (VOL_3<1e-6 AND SOL_3<1e-7) then 0 else if ADJ_SOLUB[COMP_3]<SOL_3/VOL_3 then ADJ_SOLUB[COMP_3] else SOL_3/VOL_3
    +0*(SOL_1+SOL_2+SOL_4+SOL_5+VOL_5+VOL_4+VOL_1+VOL_2)
  - CONCENTRATIONS[COMP_4] = if VOL_4 = 0.0 then 0 else if (VOL_4<1e-6 AND SOL_4<1e-7) then 0 else if ADJ_SOLUB[COMP_4]<SOL_4/VOL_4 then ADJ_SOLUB[COMP_4] else SOL_4/VOL_4
    +0*(SOL_1+SOL_2+SOL_3+SOL_5+VOL_1+VOL_2+VOL_3+VOL_5)

○ CONCENTRATIONS[COMP_5] = if VOL_5 = 0.0 then 0 else if (VOL_5<1e-6 AND SOL_5<1e-7) then 0 else if ADJ_SOLUB[COMP_5]<SOL_5/VOL_5 then ADJ_SOLUB[COMP_5] else SOL_5/VOL_5
+0*(SOL_1+SOL_4+SOL_3+SOL_2+VOL_3+VOL_1+VOL_2+VOL_4)

CONTROL RELEASE CALCULATION
○ CR_DOSE = 0
○ CR_RATE = (CR_AT_TIME-CR_AT_LAST)*20*(CR_DOSE/100)
○ CR_AT_LAST = GRAPH(TIME-DT)
(0.00, 0.00), (0.25, 17.7), (0.5, 31.5), (0.75, 42.2), (1.00, 50.6), (1.25, 57.1), (1.50, 62.1), (1.75, 66.1), (2.00, 69.2), (2.25, 71.6), (2.50, 73.4), (2.75, 74.9), (3.00, 76.0), (3.25, 76.9), (3.50, 77.6), (3.75, 78.1), (4.00, 78.5), (4.25, 78.9), (4.50, 79.1), (4.75, 79.3), (5.00, 79.5), (5.25, 79.6), (5.50, 79.7), (5.75, 79.7), (6.00, 79.8), (6.25, 79.8), (6.50, 79.9), (6.75, 79.9), (7.00, 79.9), (7.25, 79.9), (7.50, 80.0), (7.75, 80.0), (8.00, 80.0), (8.25, 80.0), (8.50, 80.0), (8.75, 80.0), (9.00, 80.0), (9.25, 80.0), (9.50, 80.0), (9.75, 80.0), (10.0, 80.0), (10.3, 80.0), (10.5, 80.0), (10.8, 80.0), (11.0, 80.0), (11.3, 80.0), (11.5, 80.0), (11.8, 80.0), (12.0, 80.0), (12.3, 80.0), (12.5, 80.0), (12.8, 80.0), (13.0, 80.0)...

○ CR_AT_TIME = GRAPH(TIME)
(0.00, 0.00), (0.25, 17.7), (0.5, 31.5), (0.75, 42.2), (1.00, 50.6), (1.25, 57.1), (1.50, 62.1), (1.75, 66.1), (2.00, 69.2), (2.25, 71.6), (2.50, 73.4), (2.75, 74.9), (3.00, 76.0), (3.25, 76.9), (3.50, 77.6), (3.75, 78.1), (4.00, 78.5), (4.25, 78.9), (4.50, 79.1), (4.75, 79.3), (5.00, 79.5), (5.25, 79.6), (5.50, 79.7), (5.75, 79.7), (6.00, 79.8), (6.25, 79.8), (6.50, 79.9), (6.75, 79.9), (7.00, 79.9), (7.25, 79.9), (7.50, 80.0), (7.75, 80.0), (8.00, 80.0), (8.25, 80.0), (8.50, 80.0), (8.75, 80.0), (9.00, 80.0), (9.25, 80.0), (9.50, 80.0), (9.75, 80.0), (10.0, 80.0), (10.3, 80.0), (10.5, 80.0), (10.8, 80.0), (11.0, 80.0), (11.3, 80.0), (11.5, 80.0), (11.8, 80.0), (12.0, 80.0), (12.3, 80.0), (12.5, 80.0), (12.8, 80.0), (13.0, 80.0)...

DISSOLUTION CALCULATION
○ ADJ_DISS_PRECIP[COMP_1] = if VOL_1=0 then 0 else if
(SOL_1/VOL_1<ADJ_SOLUB[COMP_1]) then
(DISSOL[COMP_1]*DISS_ADJ[COMP_1]*MASS_1*(ADJ_SOLUB[COMP_1]-SOL_1/VOL_1)) else
((SOL_1/VOL_1)-ADJ_SOLUB[COMP_1])*PRECIP[COMP_1]+
0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)

○ ADJ_DISS_PRECIP[COMP_2] = if VOL_2=0 then 0 else if
(SOL_2/VOL_2<ADJ_SOLUB[COMP_2]) then
(DISSOL[COMP_2]*DISS_ADJ[COMP_2]*MASS_2*(ADJ_SOLUB[COMP_2]-SOL_2/VOL_2)) else
((SOL_2/VOL_2)-ADJ_SOLUB[COMP_2])*PRECIP[COMP_2]
+0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)

○ ADJ_DISS_PRECIP[COMP_3] = if VOL_3=0 then 0 else if
(SOL_3/VOL_3<ADJ_SOLUB[COMP_3]) then
(DISSOL[COMP_3]*DISS_ADJ[COMP_3]*MASS_3*(ADJ_SOLUB[COMP_3]-SOL_3/VOL_3)) else
((SOL_3/VOL_3)-ADJ_SOLUB[COMP_3])*PRECIP[COMP_3]
+0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)

○ ADJ_DISS_PRECIP[COMP_4] = if VOL_4=0 then 0 else if
(SOL_4/VOL_4<ADJ_SOLUB[COMP_4]) then
(DISSOL[COMP_4]*DISS_ADJ[COMP_4]*MASS_4*(ADJ_SOLUB[COMP_4]-SOL_4/VOL_4)) else
((SOL_4/VOL_4)-ADJ_SOLUB[COMP_4])*PRECIP[COMP_4]
+0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)

○ ADJ_DISS_PRECIP[COMP_5] = if VOL_5=0 then 0 else if
(SOL_5/VOL_5<ADJ_SOLUB[COMP_5]) then
(DISSOL[COMP_5]*DISS_ADJ[COMP_5]*MASS_5*(ADJ_SOLUB[COMP_5]-SOL_5/VOL_5)) else
((SOL_5/VOL_5)-ADJ_SOLUB[COMP_5])*PRECIP[COMP_5]
+0*(MASS_1+MASS_2+MASS_3+MASS_4+MASS_5+SOL_1+SOL_2+SOL_3+SOL_4+SOL_5+VOL_1+VOL_2+VOL_3+VOL_4+VOL_5)

○ DISSOL[COMP_1] = 1
○ DISSOL[COMP_2] = 1
○ DISSOL[COMP_3] = 1
○ DISSOL[COMP_4] = 1
○ DISSOL[COMP_5] = 1
○ PRECIP[COMP_1] = 10
○ PRECIP[COMP_2] = 10
○ PRECIP[COMP_3] = 10
○ PRECIP[COMP_4] = 10
○ PRECIP[COMP_5] = 10

INPUTS
INTESTINAL MODEL

☐ ABSORPTION_1(t) = ABSORPTION_1(t - dt) + (FLUX_1) * dt
INIT ABSORPTION_1 = 0
INFLOWS:
⚡ FLUX_1 =
CONCENTRATIONS[COMP_1]*ADJ_PERM[COMP_1]*SURFACE_AREA[COMP_1]

☐ ABSORPTION_2(t) = ABSORPTION_2(t - dt) + (FLUX_2) * dt
INIT ABSORPTION_2 = 0
INFLOWS:
⚡ FLUX_2 =
CONCENTRATIONS[COMP_2]*ADJ_PERM[COMP_2]*SURFACE_AREA[COMP_2]

☐ ABSORPTION_3(t) = ABSORPTION_3(t - dt) + (FLUX_3) * dt
INIT ABSORPTION_3 = 0
INFLOWS:
⚡ FLUX_3 =
CONCENTRATIONS[COMP_3]*ADJ_PERM[COMP_3]*SURFACE_AREA[COMP_3]

☐ ABSORPTION_4(t) = ABSORPTION_4(t - dt) + (FLUX_4) * dt
INIT ABSORPTION_4 = 0
INFLOWS:

- FLUX_4 = CONCENTRATIONS[COMP_4]*ADJ_PERM[COMP_4]*SURFACE_AREA[COMP_4]

☐ ABSORPTION_5(t) = ABSORPTION_5(t - dt) + (FLUX_5) * dt
INIT ABSORPTION_5 = 0
INFLOWS:
- FLUX_5 = if time<32 then CONCENTRATIONS[COMP_5]*ADJ_PERM[COMP_5]*SURFACE_AREA[COMP_5]*(32-time)/48*(VOL_5/17.2) else 0

☐ C_REL_1(t) = C_REL_1(t - dt) + (- CR_OUT_1 - CR_INPUT_1) * dt
INIT C_REL_1 = CR_DOSE
OUTFLOWS:
- CR_OUT_1 = IF TIME >= CUMU_TT[COMP_1] THEN C_REL_1*10000 ELSE 0
- CR_INPUT_1 = if TIME>CUMU_TT[COMP_1] then 0 else CR_RATE ☐ C_REL_2(t) = C_REL_2(t - dt) + (CR_OUT_1 - CR_OUT_2 - CR_INPUT_2) * dt
INIT C_REL_2 = 0
INFLOWS:
- CR_OUT_1 = IF TIME >= CUMU_TT[COMP_1] THEN C_REL_1*10000 ELSE 0
OUTFLOWS:
- CR_OUT_2 = IF TIME >= CUMU_TT[COMP_2] THEN C_REL_2*10000 ELSE 0
- CR_INPUT_2 = if TIME>CUMU_TT[COMP_2] then 0 else CR_RATE ☐ C_REL_3(t) = C_REL_3(t - dt) + (CR_OUT_2 - CR_OUT_3 - CR_INPUT_3) * dt
INIT C_REL_3 = 0
INFLOWS:
- CR_OUT_2 = IF TIME >= CUMU_TT[COMP_2] THEN C_REL_2*10000 ELSE 0
OUTFLOWS:
- CR_OUT_3 = IF TIME >= CUMU_TT[COMP_3] THEN C_REL_3*10000 ELSE 0
- CR_INPUT_3 = if TIME > CUMU_TT[COMP_3] then 0 else CR_RATE ☐ C_REL_4(t) = C_REL_4(t - dt) + (CR_OUT_3 - CR_OUT_4 - CR_INPUT_4) * dt
INIT C_REL_4 = 0
INFLOWS:
- CR_OUT_3 = IF TIME >= CUMU_TT[COMP_3] THEN C_REL_3*10000 ELSE 0
OUTFLOWS:
- CR_OUT_4 = IF TIME >= CUMU_TT[COMP_4] THEN C_REL_4*10000 ELSE 0
- CR_INPUT_4 = if TIME>CUMU_TT[COMP_4] then 0 else CR_RATE ☐ C_REL_5(t) = C_REL_5(t - dt) + (CR_OUT_4 - CR_OUT_5 - CR_INPUT_5) * dt
INIT C_REL_5 = 0
INFLOWS:
- CR_OUT_4 = IF TIME >= CUMU_TT[COMP_4] THEN C_REL_4*10000 ELSE 0
OUTFLOWS:
- CR_OUT_5 = IF TIME >= CUMU_TT[COMP_5] THEN C_REL_5*10000 ELSE 0
- CR_INPUT_5 = if TIME>CUMU_TT[COMP_5] then 0 else CR_RATE ☐ C_REL_6(t) = C_REL_6(t - dt) + (CR_OUT_5) * dt
INIT C_REL_6 = 0
INFLOWS:
- CR_OUT_5 = IF TIME >= CUMU_TT[COMP_5] THEN C_REL_5*10000 ELSE 0

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of screening a compound library or portion thereof by absorption, the method comprising:
   providing a computer-implemented pharmacokinetic tool comprising an input/output system and a physiological model of a mammalian system of interest; the model comprises a selected adjustment parameter and the selected adjustment parameter comprises a value obtained by:
   (i) assigning an initial value to the selected adjustment parameter;
   (ii) inputting first data for a plurality of compounds into the model and running the model to generate output data;
   (iii) comparing the output data with second data for the plurality of compounds;
   (iv) selecting a new value for the selected adjustment parameter such that deviation of the comparison in step (iii) is reduced; and
   (v) replacing the value of the selected adjustment parameter in the model with the new value selected in step (iv);
   providing in vitro permeability and solubility data for a plurality of test samples from the compound library or portion thereof to the computer-implemented pharmacokinetic tool;
   providing initial dose data to the computer-implemented pharmacokinetic tool;
   generating a predicted in viva absorption profile for each of the plurality of test samples with the computer-implemented pharmacokinetic tool; and
   based on the generated absorption profiles, producing a secondary compound library comprising compounds having a desired absorption profile, whereby the compound library or portion thereof is screened by absorption.

2. The method of claim 1, wherein said physiological model is a mathematical model of said mammalian system comprising as operably linked components: equations for calculating solubility and absorption of a test sample for one or more physiological segments of the mammal system of interest; and initial parameter values for the equations corresponding to physiological parameters and one or more selectively optimized adjustment parameters for one or more physiological segments of said mammal system of interest.

3. The method of claim 1, wherein said permeability data is derived from a cell-based assay.

4. The method of claim 3, wherein said solubility and said dissolution rate data is derived from a chemical-based assay.

5. The method of claim 1, wherein said mammalian system of interest is selected from the group consisting of the gastrointestinal tract, the eye, the nose, the lung, the skin, and the brain.

6. The method of claim 1, wherein said compound library is selected from the group consisting of a natural library, a synthetic library, and a combinatorial library.

7. The method of claim 1, wherein said physiological model is for a mammalian system selected from the group consisting of gastrointestinal tract, eye, nose, lung, skin, and blood brain barrier.

8. The method of claim 1, which further comprises:
   generating one or more predicted in vivo pharmacokinetic properties in addition to the absorption profile for the plurality of test samples;
   selecting compounds by one or more of said properties; and
   producing one or more compound libraries characterized by absorption, and one or more of said properties.

9. The method of claim 8, wherein said one or more properties in addition to absorption is selected from the group consisting of metabolism, toxicity and activity.

* * * * *

UNITED STATES PATENT AND TRADEMARK OFFICE
CERTIFICATE OF CORRECTION

PATENT NO. : 6,996,473 B2
APPLICATION NO. : 09/989533
DATED : February 7, 2006
INVENTOR(S) : George M. Grass et al.

Page 1 of 1

It is certified that error appears in the above-identified patent and that said Letters Patent is hereby corrected as shown below:

Col. 105, line 40, change "viva" to "vivo"

Signed and Sealed this

Fifteenth Day of August, 2006

JON W. DUDAS
*Director of the United States Patent and Trademark Office*